(12) United States Patent
Wakita et al.

(10) Patent No.: US 8,383,371 B2
(45) Date of Patent: *Feb. 26, 2013

(54) NUCLEIC ACID CONSTRUCT CONTAINING A NUCLEIC ACID DERIVED FROM THE GENOME OF HEPATITIS C VIRUS (HCV) OF GENOTYPE 2A, AND A CELL HAVING SUCH NUCLEIC ACID CONSTRUCT INTRODUCED THEREIN

(75) Inventors: Takaji Wakita, Tokyo (JP); Takanobu Kato, Nagoya (JP); Tomoko Date, Kawasaki (JP)

(73) Assignees: Toray Industries, Inc., Tokyo (JP); Tokyo Metropolitan Institute of Medical Science, Tokyo (JP); Ralf Bartenschlager, Schriesheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,318

(22) Filed: Dec. 1, 2010

(65) Prior Publication Data

US 2011/0092688 A1    Apr. 21, 2011

Related U.S. Application Data

(62) Division of application No. 10/558,155, filed as application No. PCT/JP03/15038 on Nov. 25, 2003, now Pat. No. 7,935,676.

(30) Foreign Application Priority Data

May 26, 2003  (JP) .................................. 2003-148242
Sep. 19, 2003  (JP) .................................. 2003-329115

(51) Int. Cl.
  *C12P 19/34*  (2006.01)
  *A61K 31/00*  (2006.01)
  *A61K 39/42*  (2006.01)
  *G01N 33/53*  (2006.01)

(52) U.S. Cl. .................. 435/91.33; 514/4.3; 424/149.1; 424/161.1; 436/820

(58) Field of Classification Search .................. None
See application file for complete search history.

(56) References Cited

U.S. PATENT DOCUMENTS 6,630,343 B1    10/2003  Bartenschlager
7,935,676 B2 *   5/2011  Wakita et al. ............... 514/44 R

FOREIGN PATENT DOCUMENTS

| CA | 2303526 A1 | 10/2000 |
| EP | 1043399 A2 | 10/2003 |
| JP | 2001-017187 A | 1/2001 |
| JP | 2002-171978 A | 6/2002 |
| WO | WO-00/76338 A2 | 12/2000 |

OTHER PUBLICATIONS

Wakita, T. et al., "Idenshigata 2a no C-gata Kan'en Virus RNA Replicon no Juritsu", Dai 25 Kai The Molecular Biology Society of Japan Nenkai Program Koen Yoshishu, Nov. 25, 2002, p. 386.
Ikeda, M. et al., J. Virol., (Mar. 2002), vol. 76, No. 6, pp. 2997 to 3006.
Friebe, P. et al., J. Virol., (2001), vol. 75, No. 24, pp. 12047 to 12057.
Lohmann, V. et al., Science, (1999), vol. 285 pp. 110 to 113.
Kato et al.; "Sequence Analysis of Hepatitis C Virus Isolated from a Fulminant Hepatitis Patient"; Jornal of Medical Virology, vol. 64, No. 3, 2001, pp. 334-339; XP 002986251.
Date Tomoko et al.; "Genotype 2a hepatitis C virus subjenomic replion can replicate in HepG2 and IMY-N9 cells"; The Journal of Biological Chemistry, vol. 279, No. 21, May 21, 2004, pp. 22371-22376; XP-002391334.
Kato Takanobu et al.; "Efficient replication of the genotype 2a hepatitis C virus subenomic replicon"; Gastroenterology 2003, vol. 125, No. 6, pp. 1808-1817; XP -002391335.
Kato T. et al, Hepatology, (Oct. 2003) vol. 38, No. 4 Suppl. 1, pp. 469A.
Japanese Office Action issued Oct. 6, 2009 related to JP 2004-572138.

* cited by examiner

*Primary Examiner* — Doug Schultz
(74) *Attorney, Agent, or Firm* — Birch, Stewart, Kolasch & Birch, LLP

(57) ABSTRACT

The present invention relates to a replicon RNA comprising a nucleotide sequence at least containing the 5' untranslated region, the nucleotide sequence encoding NS3 protein, NS4A protein, NS4B protein, NS5A protein and NS5B protein, and the 3' untranslated region on the genomic RNA of hepatitis C virus of genotype 2a.

3 Claims, 25 Drawing Sheets
(11 of 25 Drawing Sheet(s) Filed in Color)

Fig.2A

```
          10         20         30         40         50         60
ACCUGCCCCU AAUAGGGCG ACACUCCGCC AUGAAUCACU CCCCUGUGAG GAACUACUGU 70         80         90        100        110        120
CUUCACGCAG AAAGCGCCUA GCCAUGGCGU UAGUAUGAGU GUCGUACAGC CUCCAGGCCC 130        140        150        160        170        180
CCCCCUCCCG GGAGAGCCAU AGUGGUCUGC GGAACCGGUG AGUACACCGG AAUUGCCGGG 190        200        210        220        230        240
AAGACUGGGU CCUUUCUUGG AUAAACCCAC UCUAUGCCCG GCCAUUUGGG CGUGCCCCCG 250        260        270        280        290        300
CAAGACUGCU AGCCGAGUAG CGUUGGGUUG CGAAAGGCCU UGUGGUACUG CCUGAUAGGG 310        320        330        340        350        360
CGCUUGCGAG UGCCCCGGGA GGUCUCGUAG ACCGUGCACC AUGAGCACAA AUCCUAAACC 370        380        390        400        410        420
UCAAAGAAAA ACCAAAAGAA ACACCAACCG UCGCCCAAUG AUUGAACAAG AUGGAUUGCA 430        440        450        460        470        480
CGCAGGUUCU CGGCCGCUU GGGUGGAGAG GCUAUUCGGC UAUGACUGGG CACAACAGAC 490        500        510        520        530        540
AAUCGGCUGC UCUGAUGCCG CCGUGUUCCG GCUGUCAGCG CAGGGCGCC CGGUUCUUUU 550        560        570        580        590        600
UGUCAAGACC GACCUGUCCG GUGCCCUGAA UGAACUGCAG GACGAGGCAG CGCGGCUAUC 610        620        630        640        650        660
GUGGCUGGCC ACGACGGGCG UUCCUUGCGC AGCUGUGCUC GACGUUGUCA CUGAAGCGGG 670        680        690        700        710        720
AAGGGACUGG CUGCUAUUGG CGAAGUGCC GGGGCAGGAU CUCCUGUCAU CUCACCUUGC 730        740        750        760        770        780
UCCUGCCGAG AAAGUAUCCA UCAUGGCUGA UGCAAUGCGG CGGCUGCAUA CGCUUGAUCC 790        800        810        820        830        840
GGCUACCUGC CCAUUCGACC ACCAAGCGAA ACAUCGCAUC GAGCGAGCAC GUACUCGGAU 850        860        870        880        890        900
GGAAGCCGGU CUUGUCGAUC AGGAUGAUCU GGACGAAGAG CAUCAGGGGC UCGCGCCAGC 910        920        930        940        950        960
CGAACUGUUC GCCAGGCUCA AGGCGCGCAU GCCCGACGGC GAGGAUCUCG UCGUGACCCA 970        980        990       1000       1010       1020
UGGCGAUGCC UGCUUGCCGA AUAUCAUGGU GGAAAAUGGC CGCUUUUCUG GAUUCAUCGA 1030       1040       1050       1060       1070       1080
CUGUGGCCGG CUGGGUGUGG CGGACCGCUA UCAGGACAUA GCGUUGGCUA CCCGUGAUAU 1090       1100       1110       1120       1130       1140
UGCUGAAGAG CUUGGCGGCG AAUGGGCUGA CCGCUUCCUC GUGCUUUACG GUAUCGCCGC 1150       1160       1170       1180       1190       1200
UCCCGAUUCG CAGCGCAUCG CCUUCUAUCG CCUUCUUGAC GAGUUCUUCU GAGUUUAAAC 1210       1220       1230       1240       1250       1260
CCUCUCCCUC CCCCCCCCCU AACGUUACUG GCCGAAGCCG CUUGGAAUAA GGCCGGUGUG 1270       1280       1290       1300       1310       1320
CGUUUGUCUA UAUGUUAUUU UCCACCAUAU UGCCGUCUUU UGGCAAUGUG AGGGCCCGGA 1330       1340       1350       1360       1370       1380
AACCUGGCCC UGUCUUCUUG ACGAGCAUUC CUAGGGGUCU UUCCCCUCUC GCCAAAGGAA
```

Fig.2B

```
            1390       1400       1410       1420       1430       1440
       UGCAAGGUCU GUUGAAUGUC GUGAAGGAAG CAGUUCCUCU GGAAGCUUCU UGAAGACAAA 1450       1460       1470       1480       1490       1500
       CAACGUCUGU AGCGACCCUU UGCAGGCAGC GGAACCCCCC ACCUGGCGAC AGGUGCCUCU 1510       1520       1530       1540       1550       1560
       GCGGCCAAAA GCCACGUGUA UAAGAUACAC CUGCAAAGGC GGCACAACCC CAGUGCCACG 1570       1580       1590       1600       1610       1620
       UUGUGAGUUG GAUAGUUGUG GAAAGAGUCA AAUGGCUCUC CUCAAGCGUA UUCAACAAGG 1630       1640       1650       1660       1670       1680
       GGCUGAAGGA UGCCCAGAAG GUACCCCAUU GUAUGGGAUC UGAUCUGGGG CCUCGGUGCA 1690       1700       1710       1720       1730       1740
       CAUGCUUUAC AUGUGUUUAG UCGAGGUUAA AAAAACGUCU AGGCCCCCCG AACCACGGGG 1750       1760       1770       1780       1790       1800
       ACGUGGUUUU CCUUUGAAAA ACACGAUGAU ACCAUGGCUC CCAUCACUGC UUAUGCCCAG 1810       1820       1830       1840       1850       1860
       CAAACACGAG GCCUCCUGGG CGCCAUAGUG GUGAGUAUGA CGGGGCGUGA CAGGACAGAA 1870       1880       1890       1900       1910       1920
       CAGGCCGGGG AAGUCCAAAU CCUGUCCACA GUCUCUCAGU CCUUCCUCGG AACAACCAUC 1930       1940       1950       1960       1970       1980
       UCGGGGGUUU UGUGGACUGU UUACCACGGA GCUGGCAACA AGACUCUAGC CGGCUUACGG 1990       2000       2010       2020       2030       2040
       GGUCCGGUCA CGCAGAUGUA CUCGAGUGCU GAGGGGACU UGGUAGGCUG GCCCAGCCCC 2050       2060       2070       2080       2090       2100
       CCUGGGACCA AGUCUUUGGA GCCGUGCAAG UGUGGAGCCG UCGACCUAUA UCUGGUCACG 2110       2120       2130       2140       2150       2160
       CGGAACGCUG AUGUCAUCCC GGCUCGAGA CGCGGGGACA AGCGGGGAGC AUUGCUCUCC 2170       2180       2190       2200       2210       2220
       CCGAGACCCA UUUCGACCUU GAAGGGGUCC UCGGGGGGGC CGGUGCUCUG CCCUAGGGGC 2230       2240       2250       2260       2270       2280
       CACGUCGUUG GGCUCUUCCG AGCAGCUGUG UGCUCUCCGG GCGUGGCCAA AUCCAUCGAU 2290       2300       2310       2320       2330       2340
       UUCAUCCCCG UUGAGACACU CGACGUUGUU ACAAGGUCUC CCACUUUCAG UGACAACAGC 2350       2360       2370       2380       2390       2400
       ACGCCACCGG CUGUGCCCCA GACCUAUCAG GUCGGGUACU UGCAUGCUCC AACUGGCAGU 2410       2420       2430       2440       2450       2460
       GGAAAGAGCA CCAAGGUCCC UGUCGCGUAU GCCGCCCAGG GGUACAAAGU ACUAGUGCUU 2470       2480       2490       2500       2510       2520
       AACCCCUCGG UAGCUGCCAC CCUGGGGUUU GGGGCGUACC UAUCCAAGGC ACAUGGCAUC 2530       2540       2550       2560       2570       2580
       AAUCCCAACA UUAGGACUGG AGUCAGGACC GUGAUGACCG GGAGGCCAU CACGUACUCC 2590       2600       2610       2620       2630       2640
       ACAUAUGGCA AAUUCUUCGC CGAUGGGGGC UGCGCUAGCG GCGCCUAUGA CAUCAUCAUA 2650       2660       2670       2680       2690       2700
       UGCGAUGAAU GCCACGCUGU GGAUGCUACC UCCAUUCUCG GCAUCGGAAC GGUCCUUGAU 2710       2720       2730       2740       2750       2760
       CAAGCAGAGA CAGCCGGGGU CAGACUAACU GUGCUGGCUA CGGCCACACC CCCCGGGUCA
```

Fig.2C

```
        2770        2780        2790        2800        2810        2820
GUGACAACCC  CCCAUCCCGA  UAUAGAAGAG  GUAGGCCUCG  GGCGGGAGGG  UGAGAUCCCC 2830        2840        2850        2860        2870        2880
UUCUAUGGGA  GGGCGAUUCC  CCUAUCCUGC  AUCAAGGGAG  GGAGACACCU  GAUUUUCUGC 2890        2900        2910        2920        2930        2940
CACUCAAAGA  AAAAGUGUGA  CGAGCUCGCG  GCGGCCCUUC  GGGCAUGGG   CUUGAAUGCC 2950        2960        2970        2980        2990        3000
GUGGCAUACU  AUAGAGGGUU  GGACGUCUCC  AUAAUACCAG  CUCAGGGAGA  UGUGGUGGUC 3010        3020        3030        3040        3050        3060
GUCGCCACCG  ACGCCCUCAU  GACGGGUAC   ACUGGAGACU  UUGACUCCGU  GAUCGACUGC 3070        3080        3090        3100        3110        3120
AAUGUAGCGG  UCACCCAAGC  UGUCGACUUC  AGCCUGGACC  CCACCUUCAC  UAUAACCACA 3130        3140        3150        3160        3170        3180
CAGACUGUCC  CACAAGACGC  UGUCUACGC   AGUCAGCGCC  GCGGGCGCAC  AGGUAGAGGA 3190        3200        3210        3220        3230        3240
AGACAGGGCA  CUUAUAGGUA  UGUUUCCACU  GGUGAACGAG  CCUCAGGAAU  GUUUGACAGU 3250        3260        3270        3280        3290        3300
GUAGUGCUUU  GUGAGUGCUA  CGACGCAGGG  GCUGCGUGGU  ACGAUCUCAC  ACCAGCGGAG 3310        3320        3330        3340        3350        3360
ACCACCGUCA  GGCUUAGAGC  GUAUUUCAAC  ACGCCCGGCC  UACCCGUGUG  UCAAGACCAU 3370        3380        3390        3400        3410        3420
CUUGAAUUUU  GGGAGGCAGU  UUUCACCGGC  CUCACACACA  UAGACGCCCA  CUUCCUCUCC 3430        3440        3450        3460        3470        3480
CAAACAAAGC  AAGCGGGGA   GAACUUCGCG  UACCUAGUAG  CCUACCAAGC  UACGGUGUGC 3490        3500        3510        3520        3530        3540
GCCAGAGCCA  AGGCCCCUCC  CCCGUCCUGG  GACGCCAUGU  GGAAGUGCCU  GGCCCGACUC 3550        3560        3570        3580        3590        3600
AAGCCUACGC  UUGCGGGCCC  CACACCUCUC  CUGUACCGUU  UGGGCCCUAU  UACCAAUGAG 3610        3620        3630        3640        3650        3660
GUCACCCUCA  CACACCCUGG  GACGAAGUAC  AUCGCCACAU  GCAUGCAAGC  UGACCUUGAG 3670        3680        3690        3700        3710        3720
GUCAUGACCA  GCACGUGGGU  CCUAGCUGGA  GGAGUCCUGG  CAGCCGUCGC  CGCAUAUUGC 3730        3740        3750        3760        3770        3780
CUGGCGACUG  GAUGCGUUUC  CAUCAUCGGC  CGCUUGCACG  UCAACCAGCG  AGUCGUCGUU 3790        3800        3810        3820        3830        3840
GCGCCGGAUA  AGGAGGUCCU  GUAUGAGGCU  UUUGAUGAGA  UGGAGGAAUG  CGCCUCUAGG 3850        3860        3870        3880        3890        3900
GCGGCUCUCA  UCGAAGAGGG  GCAGCGGAUA  GCCGAGAUGU  UGAAGUCCAA  GAUCCAAGGC 3910        3920        3930        3940        3950        3960
UUGCUGCAGC  AGGCCUCUAA  GCAGGCCCAG  GACAUACAAC  CCGCUAUGCA  GGCUUCAUGG 3970        3980        3990        4000        4010        4020
CCCAAAGUGG  AACAAUUUUG  GGCCAGACAC  AUGUGGAACU  UCAUUAGCGG  CAUCCAAUAC 4030        4040        4050        4060        4070        4080
CUCGCAGGAU  UGUCAACACU  GCCAGGGAAC  CCCGCGGUGG  CUUCCAUGAU  GGCAUUCAGU 4090        4100        4110        4120        4130        4140
GCCGCCCUCA  CCAGUCCGUU  GUCGACCAGU  ACCACCAUCC  UUCUCAACAU  CAUGGGAGGC
```

Fig.2D

```
           4150       4160       4170       4180       4190       4200
     UGGUUAGCGU CCCAGAUCGC ACCACCCGCG GGGGCCACCG GCUUUGUCGU CAGUGGCCUG
           4210       4220       4230       4240       4250       4260
     GUGGGGGCUG CCGUGGGCAG CAUAGGCCUG GGUAAGGUGC UGGUGGACAU CCUGGCAGGA
           4270       4280       4290       4300       4310       4320
     UAUGGUGCGG GCAUUCGGG GGCCCUCGUC GCAUUCAAGA UCAUGUCUGG CGAGAAGCCC
           4330       4340       4350       4360       4370       4380
     UCUAUGGAAG AUGUCAUCAA UCUACUGCCU GGGAUCCUGU CUCCGGGAGC CCUGGUGGUG
           4390       4400       4410       4420       4430       4440
     GGGGUCAUCU GCGCGGCCAU UCUGCGCCGC CACGUGGGAC CGGGGAGGG CGCGGUCCAA
           4450       4460       4470       4480       4490       4500
     UGGAUGAACA GGCUUAUUGC CUUUGCUUCC AGAGGAAACC ACGUCGCCCC UACUCACUAC
           4510       4520       4530       4540       4550       4560
     GUGACGGAGU CGGAUGCGUC GCAGCGUGUG ACCCAACUAC UUGGCUCUCU UACUAUAACC
           4570       4580       4590       4600       4610       4620
     AGCCUACUCA GAAGACUCCA CAAUUGGAUA ACUGAGGACU GCCCCAUCCC AUGCUCCGGA
           4630       4640       4650       4660       4670       4680
     UCCUGGCUCC GCGACGUGUG GGACUGGGUU UGCACCAUCU UGACAGACUU CAAAAAUUGG
           4690       4700       4710       4720       4730       4740
     CUGACCUCUA AAUUGUUCCC CAAGCUGCCC GGCCUCCCCU UCAUCUCUUG UCAAAGGGG
           4750       4760       4770       4780       4790       4800
     UACAAGGGUG UGUGGGCCGG CACUGGCAUC AUGACCACGC GCUGCCCUUG CGGCGCCAAC
           4810       4820       4830       4840       4850       4860
     AUCUCUGGCA AUGUCCGCCU GGGCUCUAUG AGGAUCACAG GGCCUAAAAC CUGCAUGAAC
           4870       4880       4890       4900       4910       4920
     ACCUGGCAGG GGACCUUUCC UAUCAAUUGC UACACGGAGG GCCAGUGCGC GCCGAAACCC
           4930       4940       4950       4960       4970       4980
     CCCACGAACU ACAAGACCGC CAUCUGGAGG GUGGCGGCCU CGGAGUACGC GGAGGUGACG
           4990       5000       5010       5020       5030       5040
     CAGCAUGGGU CGUACUCCUA UGUAACAGGA CUGACCACUG ACAAUCUGAA AAUUCCUUGC
           5050       5060       5070       5080       5090       5100
     CAACUACCUU CUCCAGAGUU UUUCUCCUGG GUGGACGGUG UGCAGAUCCA UAGGUUUGCA
           5110       5120       5130       5140       5150       5160
     CCCACACCAA AGCCGUUUUU CCGGGAUGAG GUCUCGUUCU GCGUUGGGCU UAAUUCCUAU
           5170       5180       5190       5200       5210       5220
     GCUGUCGGGU CCCAGCUUCC CUGUGAACCU GAGCCCGACG CAGACGUAUU GAGGUCCAUG
           5230       5240       5250       5260       5270       5280
     CUAACAGAUC CGCCCCACAU CACGGCGGAG ACUGCGGCGC GGCGCUUGGC ACGGGAUCA
           5290       5300       5310       5320       5330       5340
     CCUCCAUCUG AGGCGAGCUC CUCAGUGAGC CAGCUAUCAG CACCGUCGCU GCGGGCCACC
           5350       5360       5370       5380       5390       5400
     UGCACCACCC ACAGCAACAC CUAUGACGUG GACAUGGUCG AUGCCAACCU GCUCAUGGAG
           5410       5420       5430       5440       5450       5460
     GGCCGGUGUGG CUCAGACAGA GCCUGAGUCC AGGGUGCCCG UUCUGGACUU UCUCGAGCCA
           5470       5480       5490       5500       5510       5520
     AUGGCCGAGG AAGAGAGCGA CCUUGAGCCC UCAAUACCAU CGGAGUGCAU GCUCCCCAGG
```

Fig.2E

```
         5530       5540       5550       5560       5570       5580
    AGCGGGUUUC CACGGGCCUU ACCGGCUUGG GCACGGCCUG ACUACAACCC GCCGCUCGUG 5590       5600       5610       5620       5630       5640
    GAAUCGUGGA GGAGGCCAGA UUACCAACCG CCCACCGUUG CUGGUUGUGC UCUCCCCCCC 5650       5660       5670       5680       5690       5700
    CCCAAGAAGG CCCCGACGCC UCCCCCAAGG AGACGCCGGA CAGUGGUCU GAGCGAGAGC 5710       5720       5730       5740       5750       5760
    ACCAUAUCAG AAGCCCUCCA GCAACUGGCC AUCAAGACCU UGGCCAGCC CCCCUCGAGC 5770       5780       5790       5800       5810       5820
    GGUGAUGCAG GCUCGUCCAC GGGGCGGGC GCCGCCGAAU CCGGCGGUCC GACGUCCCCU 5830       5840       5850       5860       5870       5880
    GGUGAGCCGG CCCCCUCAGA GACAGGUUCC GCCUCCUCUA UGCCCCCCCU CGAGGGGGAG 5890       5900       5910       5920       5930       5940
    CCUGGAGAUC CGGACCUGGA GUCUGAUCAG GUAGAGCUUC AACCUCCCCC CCAGGGGGGG 5950       5960       5970       5980       5990       6000
    GGGGUAGCUC CCGGUUCGGG CUCGGGUCU UGGUCUACUU GCUCCGAGGA GGACGAUACC 6010       6020       6030       6040       6050       6060
    ACCGUGUGCU GCUCCAUGUC AUACUCCUGG ACCGGGGCUC UAAUAACUCC CUGUAGCCCC 6070       6080       6090       6100       6110       6120
    GAAGAGGAAA AGUUGCCAAU CAACCCUUUG AGUAACUCGC UGUUGCGAUA CCAUAACAAG 6130       6140       6150       6160       6170       6180
    GUGUACUGUA CAACAUCAAA GAGCGCCUCA CAGAGCGCUA AAAAGGUAAC UUUUGACAGG 6190       6200       6210       6220       6230       6240
    ACGCAAGUGC UCGACGCCCA UUAUGACUCA GUCUUAAAGG ACAUCAAGCU AGCGGCUUCC 6250       6260       6270       6280       6290       6300
    AAGGUCAGCG CAAGGCUCCU CACCUUGGAG GAGGCGUGCC AGUUGACUCC ACCCCAUUCU 6310       6320       6330       6340       6350       6360
    GCAAGAUCCA AGUAUGGAUU CGGGGCCAAG GAGGUCCGCA GCUUGUCCGG GAGGGCCGUU 6370       6380       6390       6400       6410       6420
    AACCACAUCA AGUCCGUGUG GAAGGACCUC CUGGAAGACC CACAAACACC AAUUCCCACA 6430       6440       6450       6460       6470       6480
    ACCAUCAUGG CCAAAAAUGA GGUGUUCUGC GUGGACCCCG CCAAGGGGGG UAAGAAACCA 6490       6500       6510       6520       6530       6540
    GCUCGCCUCA UCGUUUACCC UGACCUCGGC GUCCGGGUCU GCGAGAAAAU GGCCCUCUAU 6550       6560       6570       6580       6590       6600
    GACAUUACAC AAAAGCUUCC UCAGGCGGUA AUGGGAGCUU CCUAUGGCUU CCAGUACUCC 6610       6620       6630       6640       6650       6660
    CCUGCCCAAC GGGUGGAGUA UCUCUUGAAA GCAUGGGCGG AAAAGAAGGA CCCCAUGGGU 6670       6680       6690       6700       6710       6720
    UUUUCGUAUG AUACCCGAUG CUUCGACUCA ACCGUCACUG AGAGAGACAU CAGGACCGAG 6730       6740       6750       6760       6770       6780
    GAGUCCAUAU ACCAGGCCUG CUCCCUGCCC GAGGAGGCCC GCACUGCCAU ACACUCGCUG 6790       6800       6810       6820       6830       6840
    ACUGAGAGAC UUUACGUAGG AGGGCCCAUG UUCAACAGCA AGGGUCAAAC CUGCGGUUAC 6850       6860       6870       6880       6890       6900
    AGACGUUGCC GCGCCAGCGG GGUGCUAACC ACUAGCAUGG GUAACACCAU CACAUGCUAU
```

Fig.2F

```
           6910       6920       6930       6940       6950       6960
      GUGAAAGCCC UAGCGGCCUG CAAGGCUGCG GGGAUAGUUG CGCCCACAAU GCUGGUAUGC 6970       6980       6990       7000       7010       7020
      GGCGAUGACC UAGUAGUCAU CUCAGAAAGC CAGGGGACUG AGGAGGACGA GCGGAACCUG 7030       7040       7050       7060       7070       7080
      AGAGCCUUCA CGGAGGCCAU GACCAGGUAC UCUGCCCCUC CUGGUGAUCC CCCCAGACCG 7090       7100       7110       7120       7130       7140
      GAAUAUGACC UGGAGCUAAU AACAUCCUGU UCCUCAAAUG UGUCUGUGGC GUUGGGCCCG 7150       7160       7170       7180       7190       7200
      CGGGGCCGCC GCAGUAACUA CCUGACCAGA GACCCAACCA CUCCACUCGC CCGGGCUGCC 7210       7220       7230       7240       7250       7260
      UGGGAAACAG UUAGACACUC CCCUAUCAAU UCAUGGCUGG GAAACAUCAU CCAGUAUGCU 7270       7280       7290       7300       7310       7320
      CCAACCAUAU GGGUUCGCAU GGUCCUAAUG ACACACUUCU UCUCCAUUCU CAUGGUCCAA 7330       7340       7350       7360       7370       7380
      GACACCCUGG ACCAGAACCU CAACUUUGAG AUGUAUGGAU CAGUAUACUC CGUGAAUCCU 7390       7400       7410       7420       7430       7440
      UUGGACCUUC CAGCCAUAAU UGAGAGGUUA CACGGGCUUG ACGCCUUUUC UAUGCACACA 7450       7460       7470       7480       7490       7500
      UACUCUCACC ACGAACUGAC GCGGGUGGCU UCAGCCCUCA GAAAACUUGG GGCGCCACCC 7510       7520       7530       7540       7550       7560
      CUCAGGGUGU GGAAGAGUCG GGCUCGCGCA GUCAGGGCGU CCCUCAUCUC CCGUGUAGGG 7570       7580       7590       7600       7610       7620
      AAAGCGGCCG UUUGCGGCCG AUAUCUCUUC AAUUGGGCGG UGAAGACCAA GCUCAAACUC 7630       7640       7650       7660       7670       7680
      ACUCCAUUGC CGGAGGCGCG CCUACUGGAC UUAUCCAGUU GGUUCACCGU CGGCGCCGGC 7690       7700       7710       7720       7730       7740
      GGGGGCGACA UUUUUCACAG CGUGUCGCGC GCCCGACCCC GCUCAUUACU CUUCGGCCUA 7750       7760       7770       7780       7790       7800
      CUCCUACUUU UCGUAGGGGU AGGCCUCUUC CUACUCCCCG CUCGGUAGAG CGGCACACAC 7810       7820       7830       7840       7850       7860
      UAGGUACACU CCAUAGCUAA CUGUUCCUUU UUUUUUUUUU UUUUUUUUUU UUUUUUUUUU 7870       7880       7890       7900       7910       7920
      UUUUUUUUUU CUUUUUUUUU UUUUUCCCUC UUUCUUCCCU UCUCAUCUUA UUCUACUUUC 7930       7940       7950       7960       7970       7980
      UUUCUUGGUG GCUCCAUCUU AGCCCUAGUC ACGGCUAGCU GUGAAAGGUC CGUGAGCCGC 7990       8000       8010       8020       8030       8040
      AUGACUGCAG AGAGUGCCGU AACUGGUCUC UCUGCAGAUC AUGU
```

Fig.3A

```
            10         20         30         40         50         60
         ACCCGCCCCU AAUAGGGGCG ACACUCCGCC AUGAAUCACU CCCCUGUGAG GAACUACUGU
            70         80         90        100        110        120
         CUUCACGCAG AAAGCGUCUA GCCAUGGCGU UAGUAUGAGU GUCGUACAGC CUCCAGGCCC
           130        140        150        160        170        180
         CCCCCUCCCG GGAGAGCCAU AGUGGUCUGC GGAACCGGUG AGUACACCGG AAUUGCCGGG
           190        200        210        220        230        240
         AAGACUGGGU CCUUUCUUGG AUAAACCCAC UCUAUGCCCG GCCAUUGGG CGUGCCCCCG
           250        260        270        280        290        300
         CAAGACUGCU AGCCGAGUAG CGUUGGGUUG CGAAAGGCCU UGUGGUACUG CCUGAUAGGG
           310        320        330        340        350        360
         UGCUUGCGAG UGCCCCGGGA GGUCUCGUAG ACCGUGCACC AUGAGCACAA AUCCCAAACC
           370        380        390        400        410        420
         UCAAAGAAAA ACCAAAAGAA ACACUAACCG UCGCCCAAUG AUUGAACAAG AUGGAUUGCA
           430        440        450        460        470        480
         CGCAGGUUCU CCGGCCGCUU GGUGGAGAG GCUAUUCGGC UAUGACUGGG CACAACAGAC
           490        500        510        520        530        540
         AAUCGGCUGC UCUGAUGCCG CCGUGUUCCG GCUGUCAGCG CAGGGGCGCC CGGUUCUUUU
           550        560        570        580        590        600
         UGUCAAGACC GACCUGUCCG GUGCCCUGAA UGAACUGCAG GACGAGGCAG CGCGGCUAUC
           610        620        630        640        650        660
         GUGGCUGGCC ACGACGGGCG UUCCUUGCGC AGCUGUGCUC GACGUUGUCA CUGAAGCGGG
           670        680        690        700        710        720
         AAGGGACUGG CUGCUAUUGG GCGAAGUGCC GGGGCAGGAU CUCCUGUCAU CUCACCUUGC
           730        740        750        760        770        780
         UCCUGCCGAG AAAGUAUCCA UCAUGGCUGA UGCAAUGCGG CGGCUGCAUA CGCUUGAUCC
           790        800        810        820        830        840
         GGCUACCUGC CCAUUCGACC ACCAAGCGAA ACAUCGCAUC GAGCGAGCAC GUACUCGGAU
           850        860        870        880        890        900
         GGAAGCCGGU CUUGUCGAUC AGGAUGAUCU GGACGAAGAG CAUCAGGGGC UCGCGCCAGC
           910        920        930        940        950        960
         CGAACUGUUC GCCAGGCUCA AGGCGCGCAU GCCCGACGGC GAGGAUCUCG UCGUGACCCA
           970        980        990       1000       1010       1020
         UGGCGAUGCC UGCUUGCCGA AUAUCAUGGU GGAAAAUGGC CGCUUUUCUG GAUUCAUCGA
          1030       1040       1050       1060       1070       1080
         CUGUGGCCGG CUGGGUGUGG CGGACCGCUA UCAGGACAUA GCGUUGGCUA CCCGUGAUAU
          1090       1100       1110       1120       1130       1140
         UGCUGAAGAG CUUGGCGGCG AAUGGGCUGA CCGCUUCCUC GUGCUUUACG GUAUCGCCGC
          1150       1160       1170       1180       1190       1200
         UCCCGAUUCG CAGCGCAUCG CCUUCUAUCG CCUUCUUGAC GAGUUCUUCU GAGUUUAAAC
          1210       1220       1230       1240       1250       1260
         CCUCUCCCUC CCCCCCCCCU AACGUUACUG GCCGAAGCCG CUUGGAAUAA GGCCGGUGUG
          1270       1280       1290       1300       1310       1320
         CGUUUGUCUA UAUGUUAUUU UCCACCAUAU UGCCGUCUUU UGGCAAUGUG AGGGCCCGGA
          1330       1340       1350       1360       1370       1380
         AACCUGGCCC UGUCUUCUUG ACGAGCAUUC CUAGGGGUCU UUCCCCUCUC GCCAAAGGAA
```

Fig.3B

```
          1390       1400       1410       1420       1430       1440
     UGCAAGGUCU GUUGAAUGUC GUGAAGGAAG CAGUUCCUCU GGAAGCUUCU UGAAGACAAA 1450       1460       1470       1480       1490       1500
     CAACGUCUGU AGCGACCCUU UGCAGGCAGC GGAACCCCCC ACCUGGCGAC AGGUGCCUCU 1510       1520       1530       1540       1550       1560
     GCGGCCAAAA GCCACGUGUA UAAGAUACAC CUGCAAAGGC GGCACAACCC CAGUGCCACG 1570       1580       1590       1600       1610       1620
     UUGUGAGUUG GAUAGUUGUG GAAAGAGUCA AAUGGCUCUC CUCAAGCGUA UUCAACAAGG 1630       1640       1650       1660       1670       1680
     GGCUGAAGGA UGCCCAGAAG GUACCCCAUU GUAUGGGAUC UGAUCUGGGG CCUCGGUGCA 1690       1700       1710       1720       1730       1740
     CAUGCUUUAC AUGUGUUUAG UCGAGGUUAA AAAAACGUCU AGGCCCCCCG AACCACGGGG 1750       1760       1770       1780       1790       1800
     ACGUGGUUUU CCUUUGAAAA ACACGAUAAU ACCAUGGCCC CCAUCACCGC UUACGCCCAG 1810       1820       1830       1840       1850       1860
     CAGACACGAG GUCUCUUGGG CUCUAUAGUG GUGAGCAUGA CGGGGCGUGA CAAGACAGAA 1870       1880       1890       1900       1910       1920
     CAGGCCGGGG AGGUCCAAGU CCUGUCCACA GUCACUCAGU CCUUCCUCGG AACAUCCAUU 1930       1940       1950       1960       1970       1980
     UCGGGGUCU UAUGGACUGU UUACCACGGA GCUGGCAACA AGACACUAGC CGGCUCGCGG 1990       2000       2010       2020       2030       2040
     GGCCCGUCA CGCAGAUGUA CUCGAGCGCC GAGGGGACU UGGUCGGGUG GCCCAGCCCU 2050       2060       2070       2080       2090       2100
     CCUGGGACCA AAUCUUUGGA GCCGUGUACG UGUGGAGCGG UCGACCUGUA UUUGGUCACG 2110       2120       2130       2140       2150       2160
     CGGAACGCUG AUGUCAUCCC GGCUCGAAGA CGCGGGGACA AGCGGGAGC GCUGCUCUCC 2170       2180       2190       2200       2210       2220
     CCGAGACCCC UUUCGACCUU GAAGGGGUCC UCGGGGGGAC CUGUGCUUUG CCCUAGGGGC 2230       2240       2250       2260       2270       2280
     CACGCUGUCG GAAUCUUCCG GGCAGCUGUG UGCUCUCGGG GUGUGGCUAA GUCCAUAGAU 2290       2300       2310       2320       2330       2340
     UUCAUCCCCG UUGAGACGCU CGACAUCGUC ACGCGGUCUC CCACCUUUAG UGACAACAGC 2350       2360       2370       2380       2390       2400
     ACACCACCAG CUGUGCCCCA GACCUAUCAG GUGGGGUACU UGCACGCCCC CACUGGCAGU 2410       2420       2430       2440       2450       2460
     GGAAAAAGCA CCAAGGUCCC CGUCGCGUAC GCCGCCCAGG GGUAUAAAGU GCUGGUGCUC 2470       2480       2490       2500       2510       2520
     AAUCCCUCGG UGGCUGCCAC CCUGGGAUUU GGGGCGUACU UGUCCAAGGC ACAUGGCAUC 2530       2540       2550       2560       2570       2580
     AACCCCAACA UUAGGACUGG AGUCAGAACU GUGACGACCG GGAGCCCAU UACAUACUCC 2590       2600       2610       2620       2630       2640
     ACGUAUGGUA AAUUCCUCGC CGAUGGGGGC UGCGCAGGCG GCGCCUAUGA CAUCAUCAUA 2650       2660       2670       2680       2690       2700
     UGCGAUGAAU GCCACUCUGU GGAUGCUACC ACUAUUCUCG GCAUCGGGAC AGUCCUUGAC 2710       2720       2730       2740       2750       2760
     CAAGCAGAGA CAGCCGGGGU CAGGCUAACU GUACUGGCCA CGGCCACGCC CCCCGGGUCG
```

Fig.3C

```
         2770       2780       2790       2800       2810       2820
    GUGACAACCC CCCAUCCCAA UAUAGAGGAG GUAGCCCUCG GACAGGAGGG UGAGAUCCCC 2830       2840       2850       2860       2870       2880
    UUCUAUGGGA GGGCGUUUCC CCUGUCUUAC AUCAAGGGAG GGAGGCACUU GAUUUUCUGC 2890       2900       2910       2920       2930       2940
    CACUCAAAGA AAAAGUGUGA CGAGCUCGCA ACGGCCCUUC GGGGCAUGGG CUUGAACGCU 2950       2960       2970       2980       2990       3000
    GUGGCAUAUU ACAGAGGGUU GGACGUCUCC AUAAUACCAA CUCAAGGAGA UGUGGUGGUC 3010       3020       3030       3040       3050       3060
    GUUGCCACCG ACGCCCUCAU GACGGGUAU ACUGGAGACU UUGACUCCGU GAUCGACUGC 3070       3080       3090       3100       3110       3120
    AACGUAGCGG UCACCCAGGC CGUAGACUUC AGCCUGGACC CCACCUUCAC UAUAACCACA 3130       3140       3150       3160       3170       3180
    CAGACUGUCC CGCAAGACGC UGUCUCAGGU AGUCAGCGCC GAGGCGCAC GGGUAGAGGA 3190       3200       3210       3220       3230       3240
    AGACUGGGCA UUUAUAGGUA UGUUUCCACU GGUGAGCGAG CCUCAGGAAU GUUGACAGU 3250       3260       3270       3280       3290       3300
    GUAGUACUCU GUGAGUGCUA CGACGCAGGA GCUGCUUGGU AUGAGCUCUC ACCAGUGGAG 3310       3320       3330       3340       3350       3360
    ACGACCGUCA GGCUCAGGGC GUAUUUCAAC ACGCCUGGCU UGCCUGUGUG CCAGGACCAC 3370       3380       3390       3400       3410       3420
    CUUGAGUUUU GCGAGGCAGU UUUCACCGGC CUCACACACA UAGACGCUCA UUUCCUUUCC 3430       3440       3450       3460       3470       3480
    CAGACAAAGC AGUCGGCGGA AAAUUUCGCA UACUUAGUAG CCUAUCAGGC CACAGUGUGC 3490       3500       3510       3520       3530       3540
    GCCAGGGCCA AAGCGCCCCC CCCGUCCUGG GACGUCAUGU GGAAGUGCUU GACUCGACUC 3550       3560       3570       3580       3590       3600
    AAGCCCACGC UUGUGGGCCC UACACCUCUC CUGUACCGUU UGGGCUCUGU UACCAACGAG 3610       3620       3630       3640       3650       3660
    GUCACCCUUA CACACCCCGU GACAAAAUAC AUCGCCACAU GCAUGCAAGC UGACCUCGAG 3670       3680       3690       3700       3710       3720
    GUCAUGACCA GCACGUGGGU CCUGGCUGGG GGAGUCUUAG CAGCCGUCGC CGCGUAUUGC 3730       3740       3750       3760       3770       3780
    UUAGCGACCG GGUGUGUUUC CAUCAUUGGC CGUUUACACA UCAACCAGCG AGCUGUCGUC 3790       3800       3810       3820       3830       3840
    GCUCCGGACA AGGAGGUCCU CUAUGAGGCU UUUGAUGAGA UGGAGGAAUG UGCCUCCAGA 3850       3860       3870       3880       3890       3900
    GCGGCUCUCC UUGAAGAGGG GCAGCGGAUA GCCGAGAUGC UGAAGUCCAA GAUCCAAGGC 3910       3920       3930       3940       3950       3960
    UUAUUGCAGC AAGCCUCUAA ACAGGCCCAG GACAUACAAC CCGCUGUGCA AGCUUCGUGG 3970       3980       3990       4000       4010       4020
    CCCAAGAUGG AGCAAUUCUG GGCCAAACAU AUGUGGAACU UCAUAAGCGG CAUUCAGUAC 4030       4040       4050       4060       4070       4080
    CUCGCAGGAC UGUCAACACU GCCAGGGAAC CCUGCUGUGG CUUCCAUGAU GGCAUUCAGC 4090       4100       4110       4120       4130       4140
    GCCGCCCUCA CCAGUCCGUU GUCAACUAGC ACCACCAUCC UUCUUAACAU UCUGGGGGC
```

Fig.3D

```
           4150       4160       4170       4180       4190       4200
      UGGCUGGCGU CCCAAAUUGC GCCACCCGCG GGGGCCACUG GCUUUGUUGU CAGUGGCCUG
           4210       4220       4230       4240       4250       4260
      GUGGGAGCUG CUGUUGGCAG CAUAGGCUUG GGUAAAGUGC UGGUGGACAU CCUGGCAGGG
           4270       4280       4290       4300       4310       4320
      UAUGGUGCGG GCAUUUCGGG GGCCCUCGUC GCGUUUAAGA UCAUGUCUGG CGAGAAGCCC
           4330       4340       4350       4360       4370       4380
      UCCAUGGAGG AUGUCAUCAA CUUGCUGCCU GGGAUUCUGU CUCCAGGUGC UCUGGUGGUG
           4390       4400       4410       4420       4430       4440
      GGAGUCAUCU GCGCGGCCAU UCUGCGCCGC CAUGUGGGAC CGGGGGAAGG CGCGGUCCAA
           4450       4460       4470       4480       4490       4500
      UGGAUGAACA GGCUUAUCGC CUUCGCUUCC AGAGGAAACC ACGUCGCCCC UACUCACUAC
           4510       4520       4530       4540       4550       4560
      GUGACGGAGU CGGAUGCGUC GCAGCGUGUC ACCCAACUGC UUGGCUCUCU CACUAUAACU
           4570       4580       4590       4600       4610       4620
      AGUCUACUCA GGAGACUUCA CAACUGGAUC ACUGAGGAUU GCCCCAUCCC AUGCGCCGGC
           4630       4640       4650       4660       4670       4680
      UCGUGGCUCC GCGAUGUGUG GGACUGGGUC UGUACCAUCC UAACAGACUU UAAGAACUGG
           4690       4700       4710       4720       4730       4740
      CUGACCUCCA AGCUGUUCCC AAAGAUGCCU GGCCUCCCCU UUAUCUCUUG CCAAAAGGGG
           4750       4760       4770       4780       4790       4800
      UACAAGGGCG UGUGGCCGG CACUGGCAUC AUGACCACAC GAUGCCCCUG CGGCGCCAAC
           4810       4820       4830       4840       4850       4860
      AUCUCUGGCA ACGUCCGCUU GGGCUCUAUG AGAAUCACAG GACCCAAAAC CUGCAUGAAC
           4870       4880       4890       4900       4910       4920
      ACCUGGCAGG GGACCUUCCC UAUCAAUUGU UAUACAGAAG GCCAGUGCUU GCCGAAACCC
           4930       4940       4950       4960       4970       4980
      GCGUUAAACU UCAAGACCGC CAUCUGGAGA GUGGCGGCCU CAGAGUACGC GGAAGUGACG
           4990       5000       5010       5020       5030       5040
      CAGCACGGAU CAUAUGCCUA UAUAACAGGG CUGACCACUG ACAACUUAAA AGUCCCUUGC
           5050       5060       5070       5080       5090       5100
      CAACUCCCCU CUCCAGAGUU UUUCUCUUGG GUGGACGGAG UACAAAUCCA UAGGUCCGCC
           5110       5120       5130       5140       5150       5160
      CCCACACCAA AGCCGUUUUU CCGGGAUGAG GUCUCGUUCA GCGUUGGGCU CAAUUCAUUU
           5170       5180       5190       5200       5210       5220
      GUCGUCGGGU CUCAGCUUCC CUGUGACCCU GAGCCCGACA CUGAGGUAGU GAUGUCCAUG
           5230       5240       5250       5260       5270       5280
      CUAACAGACC CAUCCCAUAU CACGGCGGAG GCUGCAGCGC GGCGUUUAGC GCGGGGUCA
           5290       5300       5310       5320       5330       5340
      CCCCCAUCUG AGGCAAGCUC CUCAGCGAGC CAGCUGUCGG CGCCAUCGCU GCGAGCCACC
           5350       5360       5370       5380       5390       5400
      UGCACCACCC ACGGUAGGAC CUAUGAUGUG GACAUGGUGG AUGCCAACCU GUUCAUGGGG
           5410       5420       5430       5440       5450       5460
      GGCGGCGUGA UUCGGAUAGA GUCUGAGUCC AAAGUGGUCG UUCUGGACUC CCUCGACUCA
           5470       5480       5490       5500       5510       5520
      AUGACCGAGG AAGAGGGCGA CCUUGAGCCU UCAGUACCAU CGGAGUAUAU GCUCCCCAGG
```

Fig.3E

```
          5530       5540       5550       5560       5570       5580
     AAGAGGUUCC CACCGGCCUU ACCGGCUUGG GCGCGGCCUG AUUACAACCC ACCGCUUGUG 5590       5600       5610       5620       5630       5640
     GAAUCGUGGA AGAGGCCAGA UUACCAACCA CCCACUGUUG CGGGCUGUGC UCUCCCCCCC 5650       5660       5670       5680       5690       5700
     CCCAAAAAGA CCCCGACGCC UCCUCCAAGG AGACGCCGGA CAGUGGUCU GAGCGAGAGC 5710       5720       5730       5740       5750       5760
     ACCAUAGGAG AUGCCCUCCA ACAGCUGGCC AUCAAGUCCU UUGGCCAGCC CCCCCCAAGC 5770       5780       5790       5800       5810       5820
     GGCGAUUCAG GCCUUUCCAC GGGGGCGGAC GCCGCCGACU CGGCGAUCG GACACCCCCU 5830       5840       5850       5860       5870       5880
     GACGAGUUGG CUCUUUCGGA GACAGGUUCU ACCUCCUCCA UGCCCCCCCU CGAGGGGGAG 5890       5900       5910       5920       5930       5940
     CCUGGGGACC CAGACCUGGA GCCUGAGCAG GUAGAGCUUC AACCUCCUCC CCAGGGGGGG 5950       5960       5970       5980       5990       6000
     GAGGCAGCUC CCGGCUCGGA CUCGGGGUCC UGGUCUACUU GCUCCGAGGA GGAUGACUCC 6010       6020       6030       6040       6050       6060
     GUCGUGUGCU GCUCCAUGUC AUAUUCCUGG ACCGGGCUC UAAUAACUCC UUGUAGCCCC 6070       6080       6090       6100       6110       6120
     GAAGAGGAAA AGUUGCCAAU UAACUCCUUG AGCAACUCGC UGUUGCGAUA CCAUAACAAG 6130       6140       6150       6160       6170       6180
     GUAUACUGUA CUACAUCAAA GAGUGCCUCA CUAAGGGCUA AAAAGGUAAC UUUUGAUAGG 6190       6200       6210       6220       6230       6240
     AUGCAAGUGC UCGACGCCUA UUAUGAUUCA GUCUUAAAGG ACAUCAAGCU AGCGGCCUCC 6250       6260       6270       6280       6290       6300
     AAGGUCAGCG CAAGGCUCCU CACCUUAGAG GAGGCGUGCC AAUUGACCCC ACCCCACUCU 6310       6320       6330       6340       6350       6360
     GCAAGAUCCA AGUAUGGGUU UGGGGCUAAG GAGGUCCGCA GCUUGUCCGG GAGGGCCGUC 6370       6380       6390       6400       6410       6420
     AACCACAUCA AGUCCGUGUG GAAGGACCUC UUGGAAGACU CACAAACACC AAUUCCUACA 6430       6440       6450       6460       6470       6480
     ACCAUCAUGG CCAAAAAUGA GGUGUUCUGC GUGGACCCCG CCAAGGGGGG UAAAAAACCA 6490       6500       6510       6520       6530       6540
     GCUCGCCUUA UCGUUUACCC UGACCUCGGC GUCAGGGUCU GCGAGAAGAU GGCCCUUUAU 6550       6560       6570       6580       6590       6600
     GAUGUCACAC AAAAGCUUCC UCAGGCGGUG AUGGGGCUU CUUAUGGCUU CCAGUACUCC 6610       6620       6630       6640       6650       6660
     CCCGCUCAGC GGGUGGAGUU UCUCUUGAAG GCAUGGGCGG AAAAGAGAGA CCCUAUGGGU 6670       6680       6690       6700       6710       6720
     UUUUCGUAUG AUACCCGAUG CUUUGACUCA ACCGUCACUG AGAGAGACAU CAGGACUGAG 6730       6740       6750       6760       6770       6780
     GAGUCCAUAU ACCAGGCCUG CUCCUUACCC GAGGAGGCCC GAACUGCCAU ACACUCGCUG 6790       6800       6810       6820       6830       6840
     ACUGAGAGAC UCUAUGUGGG AGGGCCCAUG UUCAACAGCA AGGCCAGUC CUGCGGGUAC 6850       6860       6870       6880       6890       6900
     AGGCGCUGCC GCGCCAGCGG GGUGCUUACC ACUAGUAUGG GAACACCAU CACAUGCUAU
```

Fig.3F

```
          6910       6920       6930       6940       6950       6960
     GUAAAAGCCC UAGCGGCUUG CAAGGCUGCG GGGAUAAUUG CGCCCACGAU GCUGGUAUGC 6970       6980       6990       7000       7010       7020
     GGCGACGACU UGGUCGUCAU CUCAGAAAGC CAGGGGACUG AGGAGGACGA GCGGAACCUG 7030       7040       7050       7060       7070       7080
     AGAGCCUUCA CGGAGGCUAU GACCAGGUAU UCUGCCCCUC CUGGUGACCC CCCCAGACCG 7090       7100       7110       7120       7130       7140
     GAAUAUGACC UGGAGCUAAU AACAUCUUGU UCCUCAAACG UGUCUGUGGC ACUUGGCCCA 7150       7160       7170       7180       7190       7200
     CAGGGCCGCC GCAGAUACUA CCUGACCAGA GACCCCACCA CUUCAAUUGC CCGGGCUGCC 7210       7220       7230       7240       7250       7260
     UGGGAAACAG UUAGACACUC CCCUGUCAAU UCAUGGCUGG GAAACAUCAU CCAGUACGCU 7270       7280       7290       7300       7310       7320
     CCAACCAUAU GGGUUCGCAU GGUCCUGAUG ACACACUUCU UCUCCAUUCU CAUGGCCCAG 7330       7340       7350       7360       7370       7380
     GACACCCUAG ACCAGAACCU UAACUUUGAA AUGUACGGAU CGGUGUACUC CGUGAGUCCU 7390       7400       7410       7420       7430       7440
     CUGGACCUCC CAGCCAUAAU UGAAAGGUUA CACGGCUUG ACGCCUUCUC UCUGCACACA 7450       7460       7470       7480       7490       7500
     UACACUCCCC ACGAACUGAC GCGGGUGGCU UCAGCCCUCA GAAAACUUGG GGCGCCACCC 7510       7520       7530       7540       7550       7560
     CUCAGAGCGU GGAAGAGUCG GGCGCGUGCA GUUAGGCGU CCCUCAUCUC CCGUGGGGG 7570       7580       7590       7600       7610       7620
     AGGGCGGCCG UUUGCGGUCG GUACCUCUUC AACUGGGCGG UGAAGACCAA GCUCAAACUC 7630       7640       7650       7660       7670       7680
     ACUCCUUUGC CGGAGGCACG CCUCCUGGAU UUGUCCAGUU GGUUACCGU CGGCGCCGGC 7690       7700       7710       7720       7730       7740
     GGGGGCGACA UUUAUCACAG CGUGUCGcGu GCCCGACCCC GCCUAUUACU CCUUAGCCUA 7750       7760       7770       7780       7790       7800
     CUCCUACUUU CUGUAGGGGU AGGCCUCUUC CUACUCCCCG CUCGAUAGAG CGGCACACAU 7810       7820       7830       7840       7850       7860
     UAGCUACACU CCAUAGCUAA CUGUUCCUUU UUUUUUUUUU UUUUUUUUUU UUUUUUUUUU 7870       7880       7890       7900       7910       7920
     UUUUUUUUUU CUUUUUUUUU UUUUCCCUC UUUCUUCCCU UCUCAUCUUA UUCUACUUUC 7930       7940       7950       7960       7970       7980
     UUUCUUGGUG GCUCCAUCUU AGCCCUAGUC ACGGCUAGCU UGAAAGGUC CGUGAGCCGC 7990       8000       8010       8020       8030       8040
     AUGACUGCAG AGAGUGCCGU AACUGGUCUC UCUGCAGAUC AUGU
```

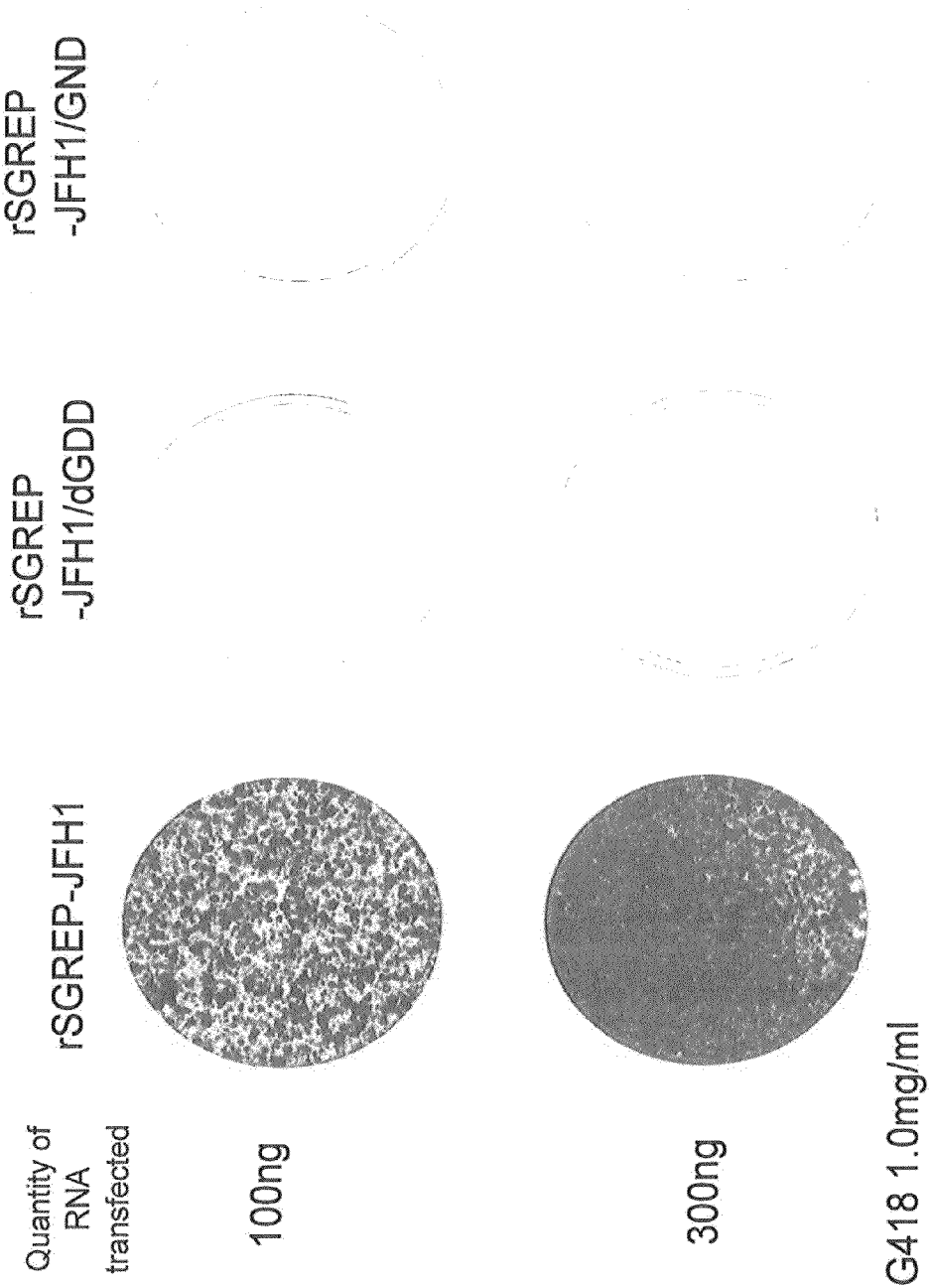

Fig.6
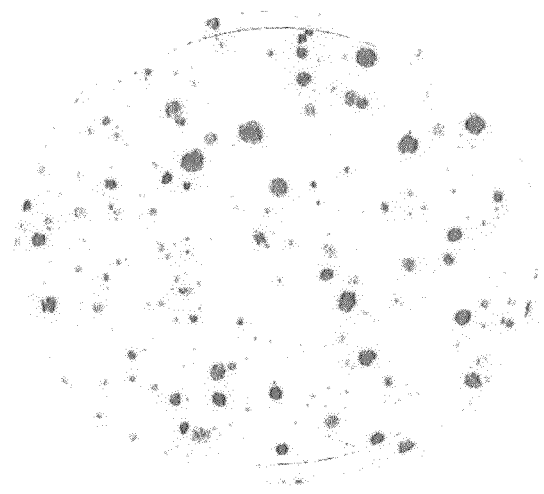
Treated with Mung Bean Nuclease
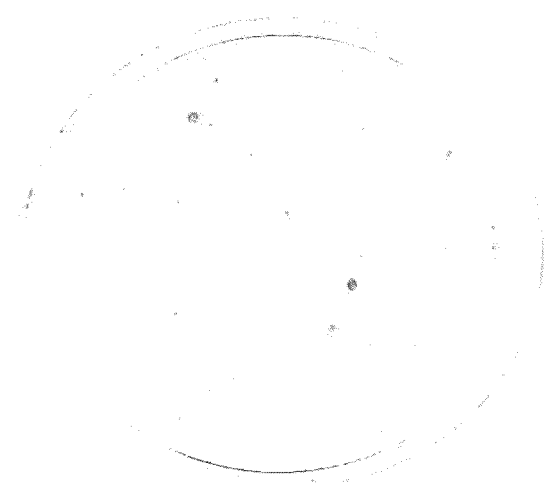
Untreated with Mung Bean Nuclease
rSGREP-JFH1
100ng
G418 1.0mg/ml

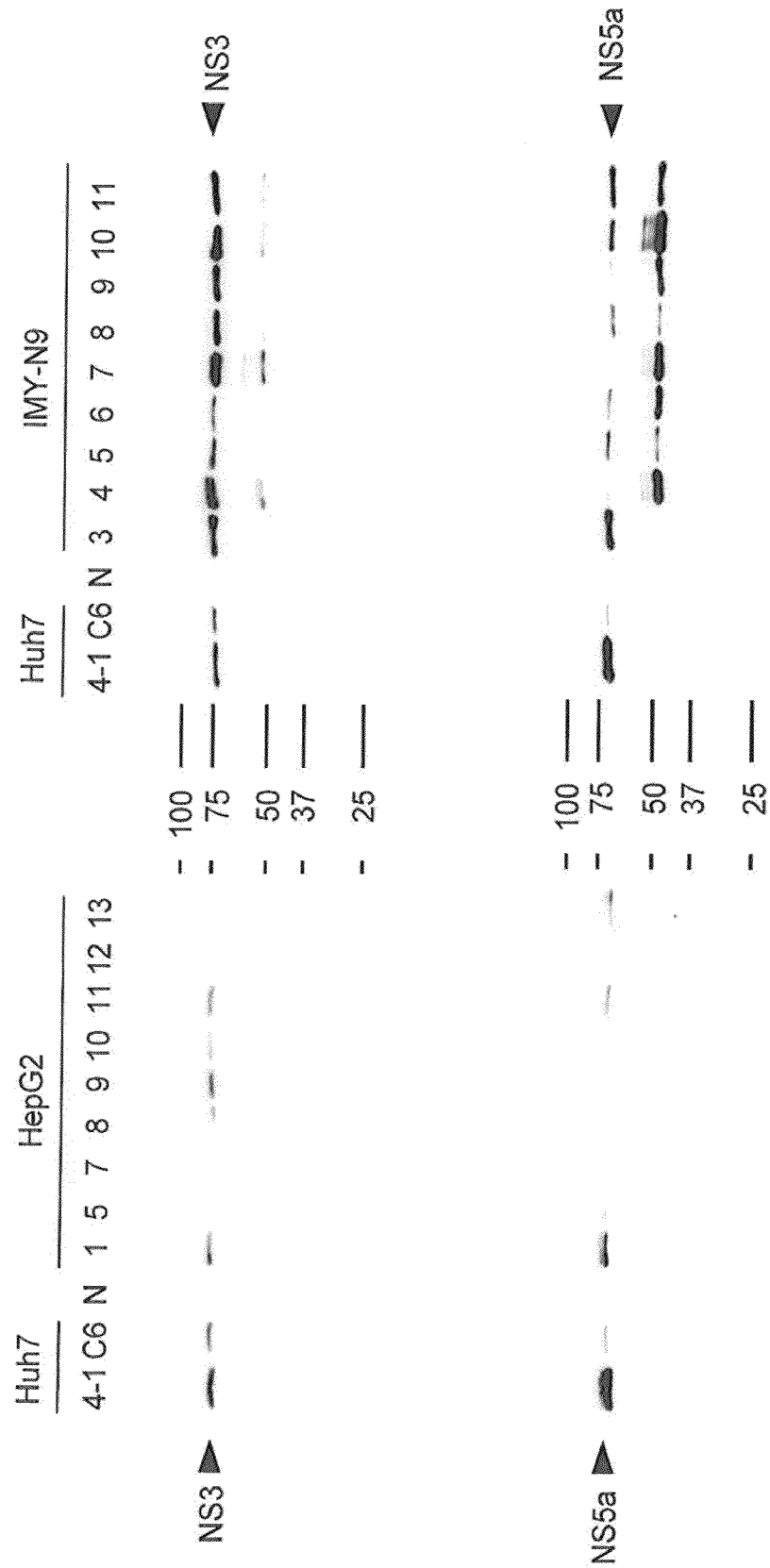

NUCLEIC ACID CONSTRUCT CONTAINING A NUCLEIC ACID DERIVED FROM THE GENOME OF HEPATITIS C VIRUS (HCV) OF GENOTYPE 2A, AND A CELL HAVING SUCH NUCLEIC ACID CONSTRUCT INTRODUCED THEREIN

This application is a Divisional of co-pending application Ser. No. 10/558,155 filed on Jan. 3, 2007 and for which priority is claimed under 35 U.S.C. §120. Application Ser. No. 10/558,155 is the national phase of PCT International Application No. PCT/JP2003/015038 filed on Nov. 25, 2003 under 35 U.S.C. §371 which claims priority under 35 USC §119 (a)-(d) of Application No. 2003-148242 filed in Japan on May 26, 2003 and Application No. 2003-329115 filed in Japan on Sep. 19, 2003. The entire contents of each of the above-identified applications are hereby incorporated by reference.

TECHNICAL FIELD

The present invention relates to a replicon RNA of the hepatitis C virus of genotype 2a, a replicon-replicating cell wherein the replicon RNA is introduced, and a method of increasing the replication efficiency of the replicon RNA.

BACKGROUND ART

The hepatitis C virus (HCV) is a virus belonging to the family Flaviviridae. It has a single-stranded (+) strand sense RNA as its genome and is known to cause hepatitis C. Recent studies have revealed that Hepatitis C virus is classified into a number of types based on genotypes or serotypes. According to the phylogenetic analysis of Simmonds et al., using the nucleotide sequences of the HCV strains, which is currently a mainstream method of classifying HCV genotypes, HCV is classified into 6 genotypes: genotype 1a, genotype 1b, genotype 2a, genotype 2b, genotype 3a and genotype 3b (see Simmonds, P. et al, Hepatology, (1994) 10, pp. 1321-1324). Each of these types is further classified into several subtypes. The nucleotide sequences of the full-length genomes of a several number of genotypes of HCV have been determined to date (see JP Patent Publication (Kokai) No. 2002-171978 A; Choo et al., Science, (1989) 244, pp. 359-362; Kato et al., J. Med. Virol., (2001) 64(3) pp. 334-339; Okamoto, H et al, J. Gen, Virol., (1992) 73 pp. 673-679; and Mori, S. et al, Biochem. Biophis. Res. Commun., (1992) 183, pp. 334-342).

HCV causes chronic hepatitis by persistent infection. Currently, the main cause of chronic hepatitis observed worldwide is persistent HCV infection. Actually, around 50% of individuals with persistent infection develop chronic hepatitis. Chronic hepatitis in approximately 20% of these patients shifts to liver cirrhosis over the course of 10 to 20 years, and some of these patients further go on to advanced lethal pathological conditions such as hepatic cancer.

Hepatitis C is currently treated mainly by a therapy using interferon-α or interferon-β, or a therapy using in combination interferon-α and ribavirin, the purine-nucleoside derivative. However, even when these therapies are performed, the therapeutic effects are observed in only approximately 60% of all the treated patients. When the therapies are ceased after the exertion of the effects, the disease recrudesces in more than half of the patients. The therapeutic effect of interferones is known to relate to HCV genotypes, and is said to be lower against genotype 1b and higher against genotype 2a (see Yoshioka et al., Hepatology, (1992) 16(2): pp. 293-299).

It is an important goal to develop therapeutic agents or prophylactic agents effective against hepatitis C, the incidence rate of which is high in industrial countries, for which currently no causal treatment are present, and which finally bring about serious results. Hence, the development of HCV-specific chemotherapies and vaccine therapies are earnestly desired. A target for the development of an anti-HCV agent may be the suppression of HCV replication or the suppression of infection of cells with HCV.

Until recently, propagation of HCV in a cell culture system and infecting cultured cells with HCV have been difficult. Moreover, a chimpanzee has been the only animal that can be infected with HCV and can be used in experiments, so that it has been difficult to carry out studies on the replication mechanism of HCV and the infection mechanism of HCV. However, recently, HCV subgenomic RNA replicons have been prepared as HCV-derived autonomously replicable RNA (see JP Patent Publication (Kokai) No. 2001-17187 A; Lohmann et al., Science, (1999) 285, pp. 110-113; Blight et al., Science, (2000) 290, pp. 1972-1974; Friebe et al., J. Viral., (2001) 75(24): pp. 12047-12057; Ikeda et al., J. Virol., (2002) 76(6): pp. 2997-3006), which enables the analysis of the replication mechanism of HCV using cultured cells. These HCV subgenomic RNA replicons are each prepared by substituting structural proteins existing downstream of HCV IRES in the 5' untranslated region of the HCV genomic RNA of genotype 1b with a neomycin resistance gene and EMCV IRES that has been ligated downstream of the resistance gene. It has been demonstrated that this RNA replicon is autonomously replicated in human hepatic cancer cells, Huh7 cells, when introduced into the Huh7 cells followed by culture in the presence of neomycin.

However, regarding such intracellular RNA replication systems for HCV, only those using HCV genomic RNA of genotype 1b have been prepared so far. Since there has been a report that different genotypes of HCV differ also in viral proteins encoded, it may be difficult to sufficiently elucidate the replication mechanism of HCV only by analyzing the subgenomic RNA replicons derived from HCV of genotype 1b. Furthermore, based on the fact that the therapeutic effects of interferons differ depending on the HCV genotypes, it may be particularly difficult to develop an anti-HCV agent having an effect on various types of HCV by the use of only an HCV replication system containing the subgenomic RNA replicon of HCV of genotype 1b.

SUMMARY OF THE INVENTION

The contents of Japanese Patent Application Nos. 2003-148242 and 2003-329115, from which the present application claims priority, are incorporated herein.

An object of the present invention is to provide an HCV-derived replicon RNA of a HCV genotype for which replicon RNA has not yet been prepared.

As a result of intensive studies to achieve the above object, we have succeeded in preparing the replicon RNA of HCV genotype 2a.

That is, the present invention is as follows.

[1] A replicon RNA, comprising a nucleotide sequence containing at least the 5' untranslated region, the nucleotide sequence encoding NS3 protein, NS4A protein, NS4B protein, NS5A protein and NS5B protein and the 3' untranslated region on the genomic RNA of hepatitis C virus of genotype 2a. Preferably, this replicon RNA further contains at least one selection marker gene or a reporter gene, and at least one IRES sequence.

[2] A replicon RNA, comprising a nucleotide sequence containing the 5' untranslated region comprising the nucleotide sequence represented by either SEQ ID NO: 9 or 10; at least one selection marker gene or a reporter gene; an IRES sequence; the nucleotide sequence encoding NS3 protein, NS4A protein, NS4B protein, NS5A protein and NS5B protein on the genomic RNA of hepatitis C virus of genotype 2a; and the 3' untranslated region comprising the nucleotide sequence represented by either SEQ ID NO: 11 or 12.

[3] The replicon RNA of [1] or [2] above, wherein the genomic RNA of hepatitis C virus of genotype 2a is an RNA comprising the nucleotide sequence represented by SEQ ID NO: 3 or 5.

[4] A replicon RNA, comprising the following RNA (a) or (b):
(a) an RNA comprising the nucleotide sequence represented by SEQ ID NO: 1 or 2; and
(b) an RNA comprising a nucleotide sequence derived from the nucleotide sequence represented by SEQ ID NO: 1 or 2 by deletion, substitution or addition of 1 to 10 nucleotides, and being capable of autonomous replication.

[5] A replicon-replicating cell, which is prepared by introducing the replicon RNA of any one of [1] to [4] above into a cell. For this replicon-replicating cell, a cell into which the replicon RNA is introduced is preferably a eukaryotic cell, more preferably a human liver-derived cell, a human uterine cervix-derived cell or a human fetal kidney-derived cell, and further more preferably any one cell selected from the group consisting of an Huh7 cell, an HepG2 cell, an IMY-N9 cell, an HeLa cell and a 293 cell.

[6] The replicon RNA of [1] to [4] above, which is for producing or evaluating a therapeutic agent or a diagnostic agent against hepatitis C virus infection.

[7] The replicon-replicating cell of [5] above, which is for producing or evaluating a therapeutic agent or a diagnostic agent against hepatitis C virus infection.

[8] The replicon RNA of [1] to [4] above, which is for producing a vaccine against hepatitis C virus infection.

[9] The replicon-replicating cell of [5] above, which is for producing a vaccine against hepatitis C virus infection.

[10] A method of producing a replicon RNA of hepatitis C virus of genotype 2a, comprising extracting the replicon RNA from the replicon-replicating cell of [5] above.

[11] A method of producing a viral protein of hepatitis C virus of genotype 2a, comprising culturing the replicon-replicating cell of [5] above, and obtaining the viral protein from the resulting culture product.

[12] A method of screening for a substance promoting or suppressing the replication of hepatitis C virus, comprising culturing the replicon-replicating cell of [5] above in the presence of a test substance, and detecting the replication of a replicon RNA in the resulting culture product.

[13] A method of increasing the replication efficiency of the replicon RNA of hepatitis C virus of genotype 2a, comprising performing once or more the following: obtaining a replicated replicon RNA from the replicon-replicating cell of [5] above, and introducing the thus obtained replicated replicon RNA into a cell that is different from the replicon-replicating cell so as to prepare a new replicon-replicating cell. In this method, it is more preferred that the replication efficiency increases to become preferably at least two times greater than that of the replicon RNA that is introduced at the beginning into the replicon-replicating cell.

[14] A method of producing a replicon RNA of hepatitis C virus of genotype 2a having increased replication efficiency, comprising performing once or more the following: obtaining a replicated replicon RNA from the replicon-replicating cell of [5] above, and introducing the thus obtained replicated replicon RNA into a cell that is different from the replicon-replicating cell so as to prepare a new replicon-replicating cell; and obtaining a replicated replicon RNA from the finally obtained replicon-replicating cell.

[15] A method of producing a replicon RNA of hepatitis C virus of genotype 2a having increased replication efficiency, comprising detecting a nucleotide mutation or an amino acid mutation between the replicon RNA that is produced so as to have an increased replication efficiency by the method of [14] above and the replicon RNA that is introduced at the beginning into the replicon-replicating cell; and introducing the thus detected nucleotide mutation or amino acid mutation into a replicon RNA whose replication efficiency is to be increased.

[16] A replicon RNA, comprising a nucleotide sequence derived from the nucleotide sequence represented by SEQ ID NO: 1 by at least one mutation selected from the group consisting of the following (a) to (u):
(a) a mutation from A to G at nucleotide site 7157;
(b) a mutation from C to U at nucleotide site 4955;
(c) a imitation from A to G at nucleotide site 4936;
(d) a mutation from A to G at nucleotide site 5000;
(e) a mutation from A to G at nucleotide site 7288;
(f) a mutation from G to U at nucleotide site 5901;
(g) a mutation from A to U at nucleotide site 6113;
(h) a mutation from A to G at nucleotide site 2890;
(i) a mutation from C to A at nucleotide site 6826;
(j) a mutation from C to A at nucleotide site 6887;
(k) a mutation from U to A at nucleotide site 6580;
(l) a mutation from U to C at nucleotide site 7159;
(m) a mutation from U to A at nucleotide site 7230;
(n) a mutation from C to A at nucleotide site 6943;
(o) a mutation from G to A at nucleotide site 5687;
(p) a mutation from A to G at nucleotide site 6110;
(q) a mutation from U to C at nucleotide site 5550;
(r) a mutation from A to G at nucleotide site 7217;
(s) a mutation from A to G at nucleotide site 3643;
(t) a mutation from G to A at nucleotide site 5851; and
(u) a mutation from G to A at nucleotide site 5914.

According to the present invention, an HCV-RNA replicon derived from the genotype 2a strain of HCV has been provided for the first time. The replicon-replicating cell according to the present invention can be used as a culture system for the continuous production of RNA and HCV proteins derived from HCV of genotype 2a. Furthermore, the replicon-replicating cell according to the present invention is useful as a test system for screening for various substances that affect HCV replication and/or the translation of HCV proteins.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 2 A to F shows the nucleotide sequence of rSGREP-JFH1 (SEQ ID NO: 1).

FIG. 3 A to F shows the nucleotide sequence of rSGREP-JCH1 (SEQ ID NO: 2).

FIG. 4 shows photographs showing the colony formation of Huh7 cells to which rSGREP-JFH1, rSGREP-JFH1/GND and rSGREP-JFH1/dGDD was transfected, respectively. The amount of each of three transfected RNAs in the upper section was 100 ng and that of three transfected RNAs in the lower section was 300 ng. 1.0 mg/ml G418 was added to each culture dish.

FIG. 6 shows photographs showing the effect of Mung Bean Nuclease treatment conducted on the colony-forming ability of the transfected cells. The amount of rSGREP-JFH1 RNA transfected was 100 ng for both cases. The concentration of G418 was 1.0 mg/ml in both media.

FIG. 15 shows photographs showing the results of analyzing by the Western blot method NS3 and NS5a proteins derived from the replicon-replicating cell clones.

BEST MODE OF CARRYING OUT THE INVENTION

Figure 1:
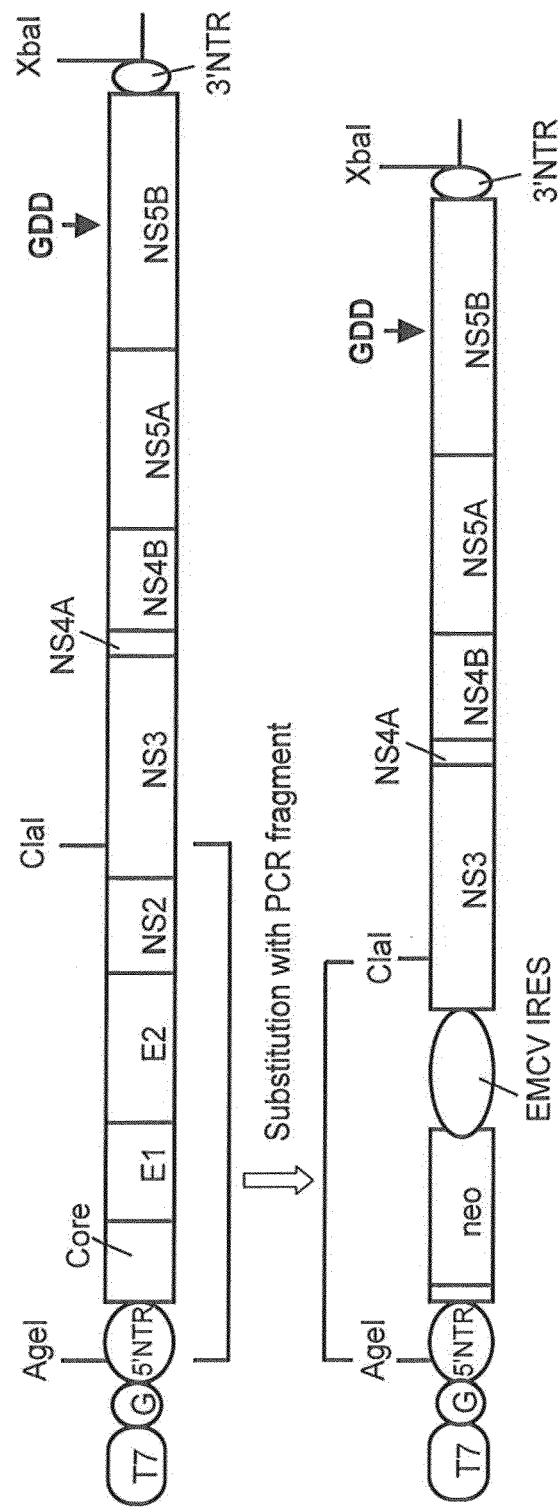
FIG. 1 is a schematic view showing procedures for constructing a template DNA for preparing the HCV-RNA replicon according to the present invention. The upper section of FIG. 1 shows the structure of the region within pJFH1 or pJCH1, with the viral genome inserted into it. The lower section of FIG. 1 shows the structure of the region within plasmid DNA pSGREP-JFH1 or pSGREP-JCH1, with the viral genome inserted into it, that had been constructed by substituting a part of viral genome-inserted region of pJFH1 or pJCH1 with a DNA fragment containing a neomycin resistance gene and EMCV IRES. Symbols in FIG. 1 are as described below. T7, T7 RNA promoter; G, dGTP that was inserted upstream of the 5' end of the inserted DNA derived from JFH-1 or JCH-1 and downstream of the 3' end of T7 RNA promoter sequence; 5' NTR, 5' untranslated region; Core, core protein; and 3' NTR, 3' untranslated region. E1 and E2 represent envelope proteins. NS2, NS3, NS4A, NS4B, NS5A and NS5B represent non-structural proteins. Age I, Cla I and Xba I represent cleavage sites of restriction enzymes Age I, Cla I and Xba I, respectively. GDD, the position of amino acid motif GDD corresponding to the active center of NS5B protein; neo, neomycin resistance gene; and EMCV IRES, internal ribosome entry site of encephalomyocarditis virus (EMCV IRES).

The present invention is explained in detail as follows.

1. HCV-DERIVED REPLICON RNA ACCORDING TO THE PRESENT INVENTION

The genome of hepatitis C virus (HCV) is a single-stranded (+) strand RNA comprising approximately 9600 nucleotides. This genomic RNA comprises the 5' untranslated region (also denoted as 5' NTR or 5' UTR), a translated region composed of a structural region and a non-structural region and the 3' untranslated region (also denoted as 3' NTR or 3' UTR). HCV structural proteins are encoded in the structural region, and a plurality of non-structural proteins are encoded in the non-structural region.

Such HCV structural proteins and non-structural proteins are generated through the translation into a continuous form thereof, a polyprotein, from the translated region, restricted degradation of the polyprotein by protease, and then the release of the structural proteins (Core, E1 and E2) and non-structural proteins (NS2, NS3, NS4A, NS4B, NS5A and NS5B), respectively. Among these structural and non-structural proteins, that is, viral proteins of HCV, Core is a core protein, E1 and E2 are envelope proteins, and non-structural proteins (NS2, NS3, NS4A, NS4B, NS5A and NS5B) are proteins involved in virus's own replication. NS2 is known to have metalloprotease activity, and NS3 is known to have serine protease activity (at one-third of the N terminal side) and helicase activity (at two-thirds of the C-terminal side). Furthermore, NS4A is a cofactor for protease activity of NS3, and NS5B has been reported to have RNA-dependent RNA polymerase activity. Furthermore, the genome of HCV of genotype 2a has already been reported to have a similar gene structure (see JP Patent Publication (Kokai) No. 2002-171978 A).

We have constructed RNA capable of autonomous replication using such HCV genome of genotype 2a. Specifically, the HCV-derived replicon RNA of the present invention is an RNA construct, which contains the whole or partial RNA of the HCV genome of genotype 2a and is capable of autonomous replication.

In this specification, RNA that is prepared by altering the viral genome of HCV and is capable of autonomous replication is referred to as "replicon RNA" or "RNA replicon." RNA that is artificially prepared from HCV of genotype 2a and is capable of autonomous replication is referred to as "replicon RNA derived from HCV of genotype 2a." In this specification, the HCV-derived replicon RNA is also referred to as an HCV-RNA replicon.

In the present invention, "hepatitis C virus of genotype 2a" or "HCV of genotype 2a" means hepatitis C virus identified as genotype 2a according to the international classification of Simmonds et al. The "hepatitis C virus of genotype 2a" or the "HCV of genotype 2a" of the present invention encompasses not only a virus having naturally occurring HCV genomic RNA, but also a virus having genomic RNA prepared by artificially altering a naturally occurring HCV genomic sequence. Specific examples of HCV of genotype 2a include viruses of NH-1 strain and the JCH-1 strain (see JP Patent Publication (Kokai) No. 2002-171978 A).

Furthermore, "the genomic RNA of hepatitis C virus of genotype 2a" means RNA that comprises the single-stranded (+) strand sense RNA of hepatitis C virus of genotype 2a and has the nucleotide sequence throughout the entire region of its genome. The genomic RNA of hepatitis C virus of genotype 2a is preferably RNA comprising the nucleotide sequence represented by SEQ ID NO: 3 or 5, but is not limited thereto.

In the specification of the present application, "5' untranslated region" (5'NTR or 5'UTR), "a sequence encoding NS3 protein, NS4A protein, NS4B protein, NS5A protein and NS5B protein," "a sequence encoding Core protein" (Core region or C region), "a sequence encoding E1 protein" (E1 region), "a sequence encoding E2 protein" (E2 region), "a sequence encoding N2 protein" (NS2 region), "a sequence encoding NS3 protein" (NS3 region), "a sequence encoding NS4A protein" (NS4A region), "a sequence encoding NS4B protein" (NS4B region), "a sequence encoding NS5A protein" (NS5A region), "a sequence encoding NS5B protein" (NS5B region) and "3' untranslated region" (3' NTR or 3' UTR), and other specific regions or sites are determined based on the nucleotide sequence of SEQ ID NO: 3 of the full-length cDNA (JFH-1 clone) encoding the entire region of the genome of the JFH-1 strain, which is HCV of genotype 2a. The nucleotide sequence of SEQ ID NO: 3 can be obtained from the International DNA Data Bank (DDBJ/EMBL/GenBank) by referring to the accession No. AB047639. Specifically, when a particular HCV RNA sequence is aligned with the nucleotide sequence represented by SEQ ID NO: 3, a sequence to be aligned with nucleotides 1 to 340 on the nucleotide sequence represented by SEQ ID NO: 3 is "5' untranslated region" of the RNA, a sequence to be aligned with the nucleotides 3431 to 9442 on the same are a sequence encoding NS3 protein, NS4A protein, NS4B protein, NS5A protein and NS5B protein, a sequence to be aligned with the nucleotides 3431 to 5323 on the same is "a sequence encoding NS3 protein," a sequence to be aligned with the nucleotides 5324 to 5485 on the same is "a sequence encoding NS4A protein," a sequence to be aligned with the nucleotides 5486 to 6268 on the same is a sequence encoding NS4B protein," a sequence to be aligned with the nucleotides 6269 to 7666 on the same is "a sequence encoding NS5A protein," a sequence to be aligned with the nucleotides 7667 to 9442 on the same is "a sequence encoding NS5B protein," and a sequence to be aligned with the nucleotides 9443 to 9678 on the same is "3' untranslated region." Furthermore, in this case, gaps, additions, deletions, substitutions or the like may be present in the "aligned" sequences. Furthermore, the above "particular HCV" is not limited thereto, and includes the JFH-1 strain or JCH-1 strain, or viral strains that are derivatives thereof.

One embodiment of the HCV RNA-replicon according to the present invention is a replicon RNA comprising a nucleotide sequence containing at least the 5' untranslated region, a sequence encoding NS3 protein, NS4A protein, NS4B protein, NS5A protein and NS5B protein, and the 3' untranslated region on the genomic RNA of hepatitis C virus of genotype 2a. The replicon RNA may further contain at least one selection marker gene or one reporter gene, and at least one IRES sequence, Furthermore, this replicon RNA may also contain a sequence encoding a viral protein other than NS3, NS4A, NS4B, NS5A and NS5B proteins on the genomic RNA of hepatitis C virus of genotype 2a.

Another preferred embodiment of HCV RNA-replicon according to the present invention is a replicon RNA comprising a nucleotide sequence containing the 5' untranslated region comprising the nucleotide sequence represented by SEQ ID NO: 9 or 10, at least one selection marker gene or reporter gene, the IRES sequence, a sequence encoding NS3 protein, NS4A protein, NS4B protein, NS5A protein and NS5B protein on the genomic RNA of hepatitis C virus of genotype 2a, and the 3' untranslated region comprising the nucleotide sequence represented by SEQ ID NO: 11 or 12. In this case the nucleotide sequences represented by SEQ ID NO: 9 and 10 are sequences of the 5' untranslated regions of rSGREP-JFH1 (SEQ ID NO: 1) and rSGREP-JCH1 (SEQ ID NO: 2), respectively, which are replicon RNAs according to the present invention. Furthermore, the nucleotide sequences represented by SEQ ID NO: 11 and 12 are sequences of the 3' untranslated regions of rSGREP-JFH1 (SEQ ID NO: 1) and rSGREP-JCH1 (SEQ ID NO: 2), respectively, which are replicon RNAs according to the present invention.

A more preferred embodiment of HCV RNA-replicon according to the present invention is a replicon RNA comprised of an RNA comprising the nucleotide sequence represented by SEQ ID NO: 1 or 2. Furthermore, a replicon RNA comprising a nucleotide sequence derived from the nucleotide sequence represented by SEQ ID NO: 1 or 2 by deletion, substitution or addition of 1 to 50, 1 to 30, 1 to 10, 1 to 6, or 1 to several (2 to 5) nucleotides, and being capable of autonomous replication is also included in the scope of the present invention as a preferred embodiment. In the present invention, "capable of autonomous replication" means that when replicon RNA is introduced into a cell, the replicon RNA allows its own full-length sequence to be replicated within the cell. For example, this ability of autonomous replication can be confirmed by transfecting replicon RNA into Huh7 cells, culturing the Huh7 cells, extracting RNA from the cells in the thus resulting culture product and conducting Northern blot hybridization for the extracted RNA using a probe that can specifically detect the transfected replicon RNA so as to detect the presence of the replicon RNA. However, examples of such a method are not limited thereto. Specific procedures for confirming the ability of autonomous replication can be conducted according to descriptions given in the Examples of this specification such as those for measuring the ability of colony formation, those for confirming the expression of HCV proteins or those for detecting replicon RNA.

In the present invention, a "selection marker gene" means a gene that can provide a cell with selectivity such that only the cell expressing the gene is selected. A general example of a selection marker gene is an antibiotic resistance gene. In the present invention, preferred examples of a selection marker gene include a neomycin resistance gene, a thymidine kinase gene, a kanamycin resistance gene, a pyrithiamine resistance gene, an adenylyl transferase gene, a Zeocin resistance gene and a puromycin resistance gene. The neomycin resistance gene and the thymidine kinase gene are preferred, and the neomycin resistance gene is more preferred. However, the selection marker gene in the present invention is not limited to these genes.

Furthermore in the present invention, a "reporter gene" means a marker gene encoding a gene product that is a marker for the expression of the gene. General examples of a reporter gene include structural genes of enzymes that catalyze light emitting reaction or color reaction. Preferred examples of the reporter gene in the present invention include a transposon Tn9-derived chloramphenicol acetyltransferase gene, an *Escherichia coli*-derived β glucuronidase or β galactosidase gene, a luciferase gene, a green fluorescence protein gene, an aequorin gene from jellyfish, and a secreted placental alkaline phosphatase (SEAP) gene. However, the reporter gene in the present invention is not limited to these genes.

Either only one or both of the above selection marker gene and reporter gene may be contained in replicon RNA.

In the present invention, "IRES sequence" means an internal ribosome entry site that allows translation to be initiated by binding ribosomes within the inside of RNA. Preferred examples of IRES sequence in the present invention include, but are not limited to, EMCV IRES (the internal ribosome entry site of encephalomyocarditis virus), FMDV IRES and HCV IRES. EMCV IRES and HCV IRES are more preferred, and EMCV IRES is the most preferred sequence.

The replicon RNA according to the present invention may further contain a sequence on the genomic RNA of another HCV strain or HCV of another genotype. For example, the replicon RNA may also contain a fragment of HCV genome of genotype 1b. Examples of another HCV strain include, but are not limited to, HCV-1, HCV-H, HC-J1, HCT-18, H77, DK-7, US11, S14, HCT23, HCV-Th, DR1, DR4, HCT27, 518, SW1, DK9, H90, TD-6E1, S9, HCV-BK, T10, DK1, HC-J4, HCV-J, HK3, HK8, HK5, HCV-G3, IND5, IND8, P10, D1, D3, SW2, T3, S45, SA10, US6, HCV-JK1, HCV-JK4, HCV-JK3, HCV-JK2, HCV-JT, HCV-T, HK4, HC-G9, Z1, Bi, S. I., Cho, J. M., HCV-J6, T4, T9, US10, HC-J5, T2, HC-J7, DK11, SW3, DK8, T8, HC-J8, S83, HK2, HC-J6, HC-J8, BEBE1, HCV-J6, HCV-J8, HD10-2, BR36-9, S52, S54, S2, BR33-1, HK10, DK12, HCV-TR, BA-1, BA-2, DK13, Z1, Z4, Z6, Z7, HK2, SA1, SA4, SA5, SA7, SA13, SA6, NZL1, SA30, EG-13, HCV-K3a/650, ED43, EUH1480, EUHK2, Th580, VN235, VN405, VN004, JK049, JK046, JFH-1, JCH-2, JCH-3, JCH-4, JCH-5, JCH-6, J6CF and H77.

The replicon RNA according to the present invention preferably has the 5' untranslated region on the genomic RNA of HCV of genotype 2a on the 5'-most side, and the 3' untranslated region on the genomic RNA of HCV of genotype 2a on the 3'-most side. A selection marker gene or a reporter gene may be ligated upstream of the IRES sequence, or upstream or downstream of "the sequence encoding NS3 protein, NS4A protein, NS4B protein, NS5A protein and NS5B protein," or inserted in the middle of "the sequence encoding NS3 protein, NS4A protein, NS4B protein, NS5A protein and NS5B protein."

The replicon RNA according to the present invention more preferably has the 5' untranslated region on the genomic RNA of HCV of genotype 2a on the 5'-most side, and a selection marker gene or a reporter gene, the IRES sequence and "the sequence encoding NS3 protein, NS4A protein, NS4B protein, NS5A protein and NS5B protein" downstream of the 5' untranslated region in this order, and the 3' untranslated region on the genomic RNA of HCV of genotype 2a on the 3'-most side.

Examples of the replicon RNA according to the present invention may include an RNA containing any foreign gene to be expressed within a cell into which the replicon RNA is introduced, in addition to the sequences as described above. A foreign gene may also be ligated downstream of the 5' untranslated region, or ligated upstream or downstream of a selection marker gene or a reporter gene, or ligated upstream or downstream of "the sequence encoding NS3 protein, NS4A protein, NS4B protein, NS5A protein and NS5B protein," or may be inserted in the middle of "the sequence encoding NS3 protein, NS4A protein, NS4B protein, NS5A protein and NS5B protein." A replicon RNA containing a foreign gene can express a protein encoded by the foreign gene when it is translated within a cell into which the RNA is introduced. Thus, the replicon RNA containing a foreign gene can be appropriately used also for gene therapy or the like, the purpose of which is to generate a particular gene product within a cell.

The replicon RNA according to the present invention may further contain a ribozyme. A ribozyme is inserted to ligate a selection marker gene, a reporter gene or a foreign gene on the 5' side in the replicon RNA to those located on the 3' side thereof including the IRES sequence and "the sequence encoding NS3 protein, NS4A protein, NS4B protein, NS5A protein and NS5B protein," so that it enables cleavage and separation of the two by the self-cleavage activity of the ribozyme.

In the replicon RNA according to the present invention, the above described selection marker gene, reporter gene, sequences encoding viral proteins on the genomic RNA of hepatitis C virus of genotype 2a, sequences encoding viral proteins of HCV of a genotype other than genotype 2a, a foreign gene or the like are ligated so that they are translated from the replicon RNA in the correct reading frame. Among these sequences, the protein-coding sequences may be ligated to each other via a protease cleavage site and the like, so that after the proteins are expressed as a fusion protein with the polyprotein that is translated from "the sequence encoding NS3 protein, NS4A protein, NS4B protein, NS5A protein and NS5B protein" of hepatitis C virus of genotype 2a, the fusion protein is separated by protease into each protein.

2. PREPARATION OF REPLICATION RNA ACCORDING TO THE PRESENT INVENTION

The HCV RNA-replicon according to the present invention can be prepared using any genetic engineering techniques known by persons skilled in the art. The HCV RNA-replicon can be prepared by, for example, the following method, but the method of preparation is not limited thereto.

First, DNA corresponding to the entire region of the genomic RNA of hepatitis C virus of genotype 2a is ligated downstream of an RNA promoter according to a standard procedure so as to prepare a DNA clone. As used herein, "DNA corresponding to RNA" means a DNA having a nucleotide sequence derived from the nucleotide sequence of the RNA by substituting U (uracil) with T (thymine). The above RNA promoter is preferably an RNA promoter contained in a plasmid clone. An example of an RNA promoter is not limited, but T7 RNA promoter is particularly preferred.

Next, for the thus prepared DNA clone, for example, the structural region (Core sequence, E1 sequence and E2 sequence) located downstream of the 5' untranslated region and the sequence encoding NS2 protein are substituted with a DNA fragment containing a selection marker gene or a reporter gene and the TRES sequence ligated downstream thereof. In this substitution, portions other than the structural region, such as a fragment on the 3' terminal side of the 5' untranslated region or a part of the sequence encoding NS3 protein may be substituted with a sequence derived from HCV of another genotype.

Subsequently, using the DNA clone after the substitution as a template, RNA is synthesized using RNA polymerase. RNA synthesis can be initiated by a standard procedure from the 5' untranslated region and the IRES sequence. When a template DNA is a plasmid clone, the above DNA region ligated downstream of an RNA promoter is excised by a restriction enzyme from the plasmid clone, and then RNA can be synthesized using the DNA fragment as a template. In addition, preferably the 3' terminus of RNA to be synthesized agrees with the 3' untranslated region of the viral genomic RNA, and no other sequences are added or deleted. The thus synthesized RNA is the replicon RNA according to the present invention.

3. PREPARATION OF REPLICON-REPLICATING CELLS INTO WHICH REPLICON RNA FROM HCV OF GENOTYPE 2A IS INTRODUCED

The replicon RNA that is prepared as described above is introduced into cells in which the replicon RNA should be replicated, so that cells wherein the replicon RNA is continuously replicated can be obtained. In this specification, a cell wherein replicon RNA is continuously replicated is referred to as a "replicon-replicating cell."

As a cell into which replicon RNA is introduced, any cell can be used, as long as it can be subcultured. Such a cell is preferably a eukaryotic cell, more preferably a human liver-derived cell, a human uterine cervix-derived cell or a human fetal kidney-derived cell, and further preferably any cell selected from the group consisting of Huh7 cells, HepG2 cells, IMY-N9 cells, HeLa cells and 293 cells. As these cells, commercially available cells may be utilized, these cells may be obtained from cell depositories, or cell lines established from any cells (e.g., cancer cells or stein cells) may also be used.

As the above cells, cells that can be mass-cultured are preferably used for the purpose of the mass production of HCV proteins, such as in the case of vaccine production. From such a viewpoint, the cells are preferably those other than Huh7 cells.

Introduction of replicon RNA into cells can be performed using any technique known by persons skilled in the art. Examples of such an introduction method include electroporation, a particle gun method, a lipofection method, a calcium phosphate method, a microinjection method and a DEAE sepharose method. The method using electroporation is particularly preferred.

A replicon RNA of interest may be introduced alone, or may be introduced after it is mixed with other nucleic acids. To vary the quantity of replicon RNA while keeping RNA quantity to be introduced at a certain level, the replicon RNA of interest is mixed with total cellular RNA extracted from cells into which the RNA is introduced, and then the mixture is used for introduction into cells. The quantity of replicon RNA to be used for introduction into cells may be determined depending on the introduction method employed, and is preferably between 1 picogram and 100 micrograms, and more preferably between 10 picograms and 10 micrograms.

When replicon RNA containing a selection marker gene or a reporter gene is used for introduction into cells, cells wherein the replicon RNA is introduced and continuously replicated can be selected utilizing the expression of the selection marker gene or the reporter gene. Specifically, for example, such cells into which replicon RNA has been introduced may be cultured in media whereby the cells can be selected by the expression of the selection marker gene or the reporter gene. As an example, when replicon RNA contains a neomycin resistance gene as a selection marker gene, cells into which replicon RNA has been intracellularly introduced are seeded into a culture dish, After 16 to 24 hours of culture, 0418 (neomycin) is added to the culture dish at a concentration of 0.05 milligrams/milliliter to 3.0 milligrams/milliliter. The cells are continuously cultured for preferably 10 days to 40 days and more preferably 14 days to 28 days after seeding, while exchanging the culture solution twice a week. Next, surviving cells are stained with crystal violet, so that cells into which the replicon RNA has been introduced and is being continuously replicated can be selected as formed colonies.

Cloned cells can be obtained from the formed colonies by cloning surviving cells by a standard procedure, and then continuing the culture of the cells. The thus obtained cell clone wherein the replicon RNA of interest is continuously replicated is referred to as "a replicon-replicating cell clone" in this specification.

Regarding the established cell clone, detection of a replicon RNA that has been replicated from the introduced replicon RNA in the cell clone, confirmation of the presence or the absence of the incorporation of a selection marker gene or a reporter gene in the introduced replicon RNA into a host genomic DNA, and confirmation of the expression of an HCV protein are preferably carried out to confirm the fact that a replicon RNA of interest is actually and continuously replicated.

A replicon RNA that has been replicated from the introduced replicon RNA in the cell clone (in this specification, hereinafter conveniently referred to as "replicated replicon RNA") may be detected according to any RNA detection method known by persons skilled in the art. For example, detection can be performed by conducting the Northern hybridization method for total RNA extracted from the cell clone using as a probe a DNA fragment specific to the introduced replicon RNA.

Furthermore, the presence or the absence of the incorporation of a selection marker gene or a reporter gene in the introduced replicon RNA into a host genomic DNA can be confirmed by, for example, performing PCR for the host genomic DNA extracted from the cell clone to amplify at least a part of the selection marker gene or the reporter gene, and then confirming the presence or the absence of the amplified product. However, examples of relevant methods are not limited thereto. A cell clone for which the amplified product is confirmed is considered to have a selection marker gene or a reporter gene incorporated in the host genome. Thus, regarding the cell clone, the replicon RNA itself may not be continuously replicated within the cell. In this case, whether or not the replicon RNA is continuously replicated can be confirmed by conducting an experiment to confirm the expression of an HCV protein, as described below.

The expression of an HCV protein can be confirmed by, for example, causing an antibody against an HCV protein to be expressed from the introduced replicon RNA and to react with a protein extracted from a cell clone. This method can be conducted by any protein detection method known by persons skilled in the art. Specifically, for example, a protein sample extracted from the cell clone is blotted onto a nitrocellulose membrane, with which an anti-HCV protein antibody (e.g., an anti-NS3-specific antibody or an antiserum collected from a hepatitis C patient) is reacted, and then the anti-HCV protein antibody is detected. If the HCV protein is detected among proteins extracted from the cell clone, it can be concluded that this cell clone continuously replicate HCV-derived replicon RNA to express the HCV protein.

As described above, cell clones confirmed to continuously replicate a replicon RNA of interest (replicon-replicating cell clones) can be obtained. Furthermore in the present invention, replicon RNA can be obtained by any method known by persons skilled in the art, for example, by extracting RNA from the replicon-replicating cell, and then separating replicon RNA from the RNA by an electrophoresis method. The present invention also relates to such a method of producing replicon RNA. Moreover, preferably, the replicon-replicating cell according to the present invention can be used for producing HCV proteins. Persons skilled in the art can obtain HCV proteins from the replicon-replicating cells according to any standard method. Specifically, for example, a viral protein of hepatitis C virus of genotype 2a can be produced by culturing replicon-replicating cells, collecting proteins from the resulting culture product (including cultured cells and culture media) by a standard procedure, and then selectively obtaining viral proteins from the proteins by detection or the like using an anti-HCV protein antibody.

Moreover, when the replicon-replicating cell according to the present invention continuously replicates replicon RNA containing a foreign gene, a protein encoded by the foreign gene can be obtained by the expression thereof using the replicon-replicating cell. Specifically, for example, the protein encoded by a foreign gene can be obtained by culturing replicon-replicating cells, collecting proteins from the resulting culture product (including cultured cells and culture media) by a standard procedure, and then selectively obtaining the protein from among the proteins by detection or the like using an antibody against the protein of interest.

4. INTRODUCTION OF MUTATION THAT INCREASES REPLICATION EFFICIENCY INTO REPLICON RNA FROM HCV OF GENOTYPE 2A

Mutation producing enhancement of replication efficiency frequently takes place in the replicon RNA that is replicated or generated in the replicon-replicating cell (replicated replicon RNA) according to the present invention. Such a mutation may be an adaptive mutation.

Utilizing this fact, introduction of a mutation enhancing replication efficiency into the replicon RNA according to the present invention can be promoted in the present invention.

Specifically, the step comprising obtaining a first replicated replicon RNA by extraction or the like from a first replicon-replicating cell (preferably, a replicon-replicating cell, wherein the replicon RNA according to the present invention has been introduced), and then re-introducing the first replicated replicon RNA into another cell to prepare a second replicon-replicating cell is performed repeatedly once or more, preferably 1 to 10 times, more preferably 1 to 5 times, and further preferably 1 to 2 times, so that the mutation increasing replication efficiency can be introduced at a high frequency into the replicon RNA within the replicon-replicating cells.

As a cell into which a replicated replicon RNA is re-introduced, any cell can be used. Such a cell is preferably derived from a biological species that is the same as that of a cell wherein replicon RNA is introduced at the beginning, more preferably derived from the same tissue derived from the same biological species as that of a cell wherein replicon RNA is introduced at the beginning, and further preferably of a cell line that is the same as that for a cell wherein replicon RNA is introduced at the beginning.

Therefore in the present invention, using the above method, replicon RNA wherein the mutation increasing replication efficiency is introduced can be produced. Specifically, the step comprising obtaining a first replicated replicon RNA by extraction or the like from a first replicon-replicating cell (preferably, a replicon-replicating cell, into which the replicon RNA according to the present invention has been introduced), and then re-introducing the first replicated replicon RNA into another cell so as to prepare a second replicon-replicating cell is performed repeatedly once or more, preferably 1 to 10 times, more preferably 1 to 5 times, and further preferably 1 to 2 times. Subsequently, the replicated replicon RNA is obtained by extraction or the like from the replicon-replicating cell finally obtained at the end of the repeated steps, so that replicon RNA with increased replication efficiency can be produced.

In the present invention, the replication efficiency of a replicon RNA can be increased at least 2 times, preferably 10 to 100 times, and more preferably 100 to 10000 times by the above method.

Regarding the replicon RNA that is produced by such a method so as to have increased replication efficiency, the nucleotide sequence is preferably determined by a known method, for example, by obtaining cDNA by reverse transcription PCR and subjecting such cDNA to sequencing.

Furthermore, the thus determined nucleotide sequence or the amino acid sequence encoded by the nucleotide sequence is compared with the nucleotide sequence of replicon RNA that had been introduced at the beginning into cells, so that adaptive mutation can be identified. As adaptive mutation increasing replication efficiency, in particular, nonsynonymous substitution that mutates an amino acid in a viral protein encoded by replicon RNA is preferred.

The present invention also provides a method whereby the replicon RNA of hepatitis C virus of genotype 2a having increased replication efficiency can be produced by introducing the thus identified adaptive mutation into replicon RNA, the replication efficiency of which is to be increased, by a standard procedure.

The replicon RNA that is produced as described above so as to have increased replication efficiency can be used for producing replicon RNA in large quantity within cells that have been used for the method.

The replication efficiency of the replicon RNA according to the present invention can be determined by a method known by persons skilled in the art. For example, it can be determined according to the following method. Replicon RNAs are transfected in quantities of 0.0001, 0.0003, 0.001, 0.003, 0.01, 0.03, 0.1, 0.3 and 1.0 micrograms, respectively, into Huh7 cells, selective culture with G418 is performed for 21 days in a method similar to the above experimental techniques, and then the number of colonies formed (number of colonies) is counted. The quantity of RNA introduced is compared with the number of colonies formed to determine the range of the quantity of the replicon RNA introduced, within which colony formation increases in a quantity-dependent manner. The number of colonies formed within the range is divided by the quantity of RNA introduced, and the resulting value is regarded as the colony forming activity per microgram. This equation is as follows.

> Colony forming activity [(Colony Forming Unit, or CFU)/microgram]=Number of colonies formed [colony]/quantity of RNA introduced [microgram]

The thus calculated colony forming activity is regarded as a value representing the replication efficiency of replicon RNA introduced. Specifically, the higher the colony forming activity, the higher the replication efficiency of the replicon RNA. In addition, the replication efficiency of replicon RNA can also be shown via a colony-forming ability that is represented by the number of copies of the replicon RNA introduced per formed colony. That is, in this case, the ability can be calculated according to the following equation.

> Colony forming ability=number of copies of replicon RNA introduced [copy]/number of formed colonies [colony]

5. OTHER EMBODIMENTS OF THE PRESENT INVENTION

The replicon RNA-replicating cell according to the present invention can also be used as a test system for, for example, screening for a substance that promotes or suppresses the replication of hepatitis C virus. Specifically, for example, replicon replicating cells are cultured in the presence of a test substance, replication of the replicon RNA in the resulting culture product is detected, and then whether or not the test substance promotes or suppresses the replication of the replicon RNA is determined, so that a substance that promotes or suppresses the replication of hepatitis C virus can be screened for In this case, detection of the replication of the replicon RNA in the resulting culture product may be conducted by detecting the quantity of, or the presence or the absence of, the replicon RNA in the RNAs extracted from the replicon RNA-replicating cell, or by detecting the quantity of, or the presence or the absence of, HCV protein contained in the proteins in the culture product or in the replicon RNA-replicating cells contained in the culture product.

Such a test cell system using the replicon RNA-replicating cells according to the present invention may be aimed at producing or evaluating a therapeutic agent or a diagnostic agent for treating hepatitis C virus infection. Specific examples of such purposes include the following examples.

(1) Search for a Substance Suppressing the Proliferation of HCV of Genotype 2a

Examples of a substance suppressing the proliferation of HCV of genotype 2a include organic chemicals directly or indirectly affecting the proliferation of HCV of genotype 2a, and antisense oligonucleotides directly or indirectly affecting the proliferation of HCV or the translation of HCV proteins by hybridizing to a target sequence in the HCV genome of genotype 2a or a complementary strand thereof.

(2) Evaluation of Various Substances Having Antiviral Action in Cell Culture

Examples of the various substances include substances obtained through rational drug design or high throughput screening (e.g., an isolated and purified enzyme) and the like.

(3) Identification of a New Target for Attack for Treating Patients Infected with HCV of Genotype 2a To identify a host cellular protein that plays an important role in proliferation of HCV virus, for example, the replicon-replicating cell according to the present invention can be used.

(4) Evaluation of the Ability of HCV Virus to Acquire Resistance Against a Drug or the Like and Identification of Mutation Concerning Such Resistance (5) Production of a Viral Protein as an Antigen that Can Be Used for Developing, Producing and Evaluating a Diagnostic Agent or a Therapeutic Agent for Hepatitis C Virus Infection (6) Viral Genome Replication System for Producing HCV Virus or Virus-Like Particles that Can Be Used for developing, Producing and Evaluating a Diagnostic Agent or a Therapeutic Agent for Hepatitis C Virus Infection (7) Production of a Vaccine Antigen that Can Be Used as a Vaccine Against HCV of Genotype 2a (8) Production of Hepatic Cell-Directed Genetic Vector that is Used After the Incorporation of a Foreign Gene therein for Gene Therapy

6. EXAMPLES

The present invention will be described more specifically based on the following examples and drawings. However, the technical scope of the present invention is not limited by these examples.

Example 1

Preparation of Replicon RNA (A) Construction of Expression Vector

DNA corresponding to the entire region of viral genome of hepatitis C virus JFH-1 strain (genotype 2a) that had been separated from patients with fulminant hepatic failure was obtained from a JFH-1 clone containing the full-length genomic cDNA of the virus strain. The DNA was inserted downstream of T7 RNA promoter sequence that had been inserted in pUC19 plasmid. The thus constructed plasmid DNA is hereinafter referred to as pJFH1. Similarly, DNA corresponding to the entire region of viral genome of hepatitis C virus JCH-1 strain (genotype 2a) that had been separated from patients with chronic hepatitis was obtained from a JCH-1 clone containing the full-length genomic cDNA of the virus strain. The DNA was inserted downstream of the T7 RNA promoter sequence that had been inserted in pUC19 plasmid. The thus constructed plasmid DNA is hereinafter referred to as pJCH1. In addition, the preparation of the above JFH1 clone and JCH-1 clone is described in JP Patent Publication (Kokai) No. 2002-171978 A and Kato et al., J. Med. Vivol., (2001) 64(3) pp. 334-339. Moreover, the nucleotide sequence of the full-length cDNA of JFH-1 clone was registered at the International DNA Data Bank (DDBJ/EMBL/GenBank) under accession No. AB047639, and the nucleotide sequence of the full-length cDNA of the JCH-1 clone under accession No. AB047640.

The structures of the thus constructed plasmid DNA pJFH1 and pJCH1 are shown in the upper section of FIG. 1. "T7" represents T7 RNA promoter, and "G" represents dGTP inserted upstream of the 5' end of the inserted JFH-1- or JCH-1-derived DNA and downstream of the 3' end of T7 RNA promoter sequence. A region from "5' NTR" to "3' NTR" is DNA corresponding to the entire genomic region of hepatitis C virus.

Next, the structural regions and a part of the non-structural regions of plasmid DNA pJFH1 and pJCH1 were substituted with a neomycin resistance gene (neo; also referred to as a neomycin phosphotransferase gene) and EMCV-IRES (internal ribosome entry site of encephalomyocarditis virus), thereby constructing plasmid DNA pSGREP-JFH1 and pSGREP-JCH1, respectively (lower section of FIG. 1). This construction procedure was conducted according to a previous report (Lohmann et al., Science, (1999) 285, pp. 110-113). Specifically, plasmid pJFH1 and pJCH1 were cleaved with restriction enzymes Age I and Cla I, and between the Age I and Cla I restriction sites, the following fragments were inserted to be ligated; a fragment was prepared by binding of a sequence ranging from 5' NTR to Core region derived from pJFH-1 with the neomycin resistance gene derived from pRSV5NEO by PCR amplification and then cleaving it with restriction enzymes Age I and Pme I, and, a fragment was prepared by binding of sequences ranging from EMCV IRES to NS3 region by PCR amplification and then cleaving it with restriction enzymes Pme I and Cla I.

Moreover, a mutation that mutates an amino acid motif GDD to GND, corresponding to the active center of RNA polymerase encoded by the NS5B region, was introduced into the NS5B region in pSGREP-JFH1, thereby preparing a mutant plasmid clone pSGREP-JFH1/GND.

Moreover, a mutation that results in the deletion of a sequence of 10 continuous amino acids containing an amino acid motif GDD corresponding to the active center of RNA polymerase encoded by the NS5B region was introduced into the NS5B region in pSGREP-JFH1, thereby preparing a mutant plasmid clone pSGREP-JFH1/dGDD.

The above-prepared mutant clones pSGREP-JFH1/GND and pSGREP-JFH1/dGDD cannot express active NS5B protein, which is required for the replication of replicon RNA, because the amino acid sequence of the active site of NS5B protein encoded by these clones has mutated.

(B) Preparation of Replicon RNA

To prepare template DNA for use in synthesis of replicon RNA, the above-constructed expression vectors pSGREP-JFH1, pSGREP-JCH1, pSGREP-JFH1/GND and pSGREP-JFH1/dGDD were each cleaved with a restriction enzyme Xba I.

Subsequently, 10 to 20 μg each of these Xba I-cleaved fragments was contained in 50 μl of a reaction solution, and then further treated by 30 minutes of incubation at 30° C. with 20 U of Mung Bean Nuclease. Mung Bean Nuclease is an enzyme catalyzing a reaction for selectively degrading a single-stranded portion of double-stranded DNA. Generally, when RNA synthesis is performed using directly the above Xba I-cleaved fragment as a template, a replicon RNA having four nucleotides of CUGA, a part of the recognition sequence of Xba I, excessively added to the 3' terminus would be synthesized. Hence, in this example, Xba I-cleaved fragments were treated with Mung Bean Nuclease, so as to remove the four nucleotides of CUGA from the fragments. The solutions containing Xba I-cleaved fragments, which had been treated with Mung Bean Nuclease, were treated to remove proteins according to a general method, so that Xba I-cleaved fragments, from which the four nucleotides of CUGA had been removed, were purified and used as template DNAs.

Next, from the template DNA, RNA was synthesized in vitro using T7 RNA polymerase. For this RNA synthesis, MEGAscript from Ambion, Inc. was used. Reaction was carried out using 20 μl of a reaction solution containing 0.5 to 1.0 micrograms of the template DNA according to the instructions of the manufacturer.

After completion of RNA synthesis, DNase (2 U) was added to the reaction solution to conduct reaction at 37° C. for 15 minutes. RNA extraction using acidic phenol was further performed to remove the template DNA. RNAs (replicon RNAs) synthesized in this manner from the above template DNAs derived from pSGREP-JFH1, pSGREP-JCH1, pSGREP-JFH1/GND and pSGREP-JFH1/dGDD were respectively named rSGREP-JFH1, rSGREP-JCH1, rSGREP-JFH1/GND and rSGREP-JFH1/dGDD. Regarding the nucleotide sequences of these replicon RNAs, the nucleotide sequence of rSGREP-JFH1 is shown in SEQ ID NO: 1 and FIG. 2A to F, that of rSGREP-JCH1 is shown in SEQ ID NO: 2 and FIG. 3A to F, that of rSGREP-JFH1/GND is shown in SEQ ID NO: 7, and that of rSGREP-JFH1/dGDD is shown in SEQ ID NO: 8.

Example 2

Establishment of Replicon-Replicating Cell Clone (C) Transfection of Replicon RNA, Determination of Colony-Forming Ability of Transfected Cells and Establishment of Cell Clones Each of the above-synthesized replicon RNAs (rSGREP-JFH1, rSGREP-JCH1, rSGREP-JFH1/GND and rSGREP-JFH1/dGDD) was mixed in different quantities with total cellular RNA extracted from Huh7 cells so as to have a total RNA quantity of 10 μg. Subsequently, the mixed RNA was introduced into Huh7 cells by the electroporation method, The Huh7 cells subjected to the electroporation treatment were seeded into culture dishes, and then cultured for 16 hours to 24 hours. G418 (neomycin) was then added to the culture dishes at different concentrations. Thereafter, culture was continued while exchanging the culture solutions twice a week. After 21 days of culture following seeding, surviving cells were stained with crystal violet. The number of stained colonies was counted, and then the number of colonies obtained per μg of the transfected replicon RNA was calculated.

For rSGREP-JFH1 or rSGREP-JCH1-transfected cells, for which colony formation had been observed, colonies of the surviving cells were further cloned from the above culture dishes after 21 days of culture, and were continuously cultured. By such cloning of colonies, several strains of cell clones could be established.

For the established cell clones, detection of the replicated replicon RNA, confirmation of the presence or the absence of the incorporation of the neomycin resistance gene into the host genomic DNA, and confirmation of the expression of HCV proteins were performed as described later, in Example 4. Cell clones for which the replication of the replicon had been confirmed in the cells were regarded as replicon-replicating cell clones.

(D) Colony-Forming Ability in each Transfected Cell

As a result of the above transfection, for rSGREP-JFH1-transfected Huh7 cells, the colony-forming ability per μg of the transfected replicon RNA was 94700 CFU (Colony Forming Unit)/μg·RNA when G418 concentration was 1.0 mg/ml (the left column in FIG. 4). In contrast, colony formation was not observed in the Huh7 cells, into which rSGREP-JFH1/dGDD and rSGREP-JFHUGND had each been transfected (the central column and the right column in FIG. 4). This suggests that the colony-forming ability confirmed for the Huh7 cells, into which rSGREP-JFH1 replicon RNA had been transfected, depends on the activity of NS5B (RNA polymerase) expressed by rSGREP-JFH1. Specifically, it was considered that in cells that had formed colonies, rSGREP-JFH1 replicon RNA autonomously replicated due to the action of NS5B expressed by rSGREP-JFH1, and the neomycin resistance gene was continuously expressed to maintain G418 resistance, so that cell growth was enabled.

Figure 5:
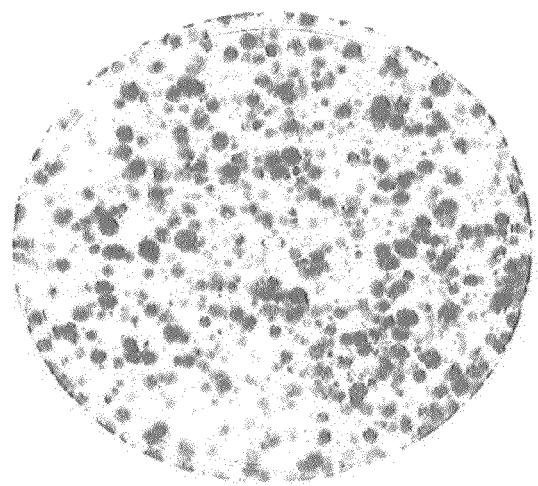
FIG. 5 shows photographs showing colony formation of Huh7 cells to which rSGREP-JFH1 and rSGREP-JCH1 respectively had been transfected when the concentration of G418 was 0.5 mg/ml of the medium. The amount of each of these RNAs transfected was 100 ng.

On the other hand, in the Huh7 cells, into which rSGREP-JCH1 had been transfected, no colony formation was observed in the ease of 1 to 0.5 mg/ml G418 concentrations (FIG. 5). When 0418 concentration was lowered to 0.25 mg/ml, colony formation was observed in the Huh7 cells, into which rSGREP-JCH1 had been transfected as well.

Furthermore, Xba I-cleaved fragment of the expression vector pSGREP-JFH1 obtained in (B) above was used as a template DNA for RNA synthesis without treating, the fragment with Mung Bean Nuclease, so as to synthesize replicon RNA. This replicon RNA was transfected to Huh7 cells in a manner similar to that in (C) above. The replicon RNA that had been prepared without performing Mung Bean Nuclease treatment had the four nucleotides of CUGA excessively added to the 3' terminus.

As a result, the colony-forming ability of the Huh7 cells, into which the replicon RNA prepared without treatment with Mung Bean Nuclease had been transfected, decreased to 512 CFU/μg·RNA (the left side in FIG. 6). This result revealed that the sequence on the 3' terminus of the replicon RNA affects the colony-forming ability of the transfected cells.

Example 3

(E) Re-Transfection of Replicated Replicon RNA Derived from Replicon-Replicating Cells From the replicon-replicating cell clones that had been established by transfection of rSGREP-JFH1 into Huh7 cells according to descriptions of Example 2, total RNA was extracted by a standard procedure. The number of copies of the replicated replicon RNA contained in the cellular RNA was determined by Northern blot analysis and a quantitative RT-PCR method.

Northern blot analysis was performed according to the description in Molecular Cloning, A laboratory Manual, $2^{nd}$ edition, J. Sambrook, E. F. Fritsch, T. Maniatis, Cold Spring Harbor Laboratory Press (1989). Specifically, RNA extracted from the cells was subjected to denaturing agarose electrophoresis. After electrophoresis, the RNA was transferred onto a positively charged nylon membrane. The $^{32}$P-labeled DNA or RNA probe prepared from pSGREP-JFH1 was hybridized to the RNA transferred to the membrane as described above. Next the membrane was washed, and then exposed to a film, so as to detect a replicon-specific RNA band.

Detection of the replicon RNA by quantitative RT-PCR was conducted by detecting the 5' untranslated region RNA within HCV RNA according to Takeuchi T, Katsume A, Tanaka T, Abe A, Inoue K, Tsukiyama-Kohara K, Kawaguchi R, Tanaka S and Kohara M., Real-time detection system for quantification of Hepatitis C virus genome, Gastroenterology 116: 636-642 (1999). Specifically, the replicon RNA contained in RNA extracted from the cells was amplified by PCR using synthetic primers: R6-130-S17, 5'-CGGGAGAGC-CATAGTGG-3' (SEQ ID NO: 13) and R6-290-R19, 5'-AG-TACCACAAGGCCTTTCG-3' (SEQ ID NO: 14); TaqMan Probe; R6-148-S21FT, 5'-CTGCGGAACCGGTGAGTA-CAC-3' (SEQ ID NO: 15) and an EZ rTth RNA PCR kit, and then detected using an ABI Prism 7700 sequence detector system.

Figure 7:
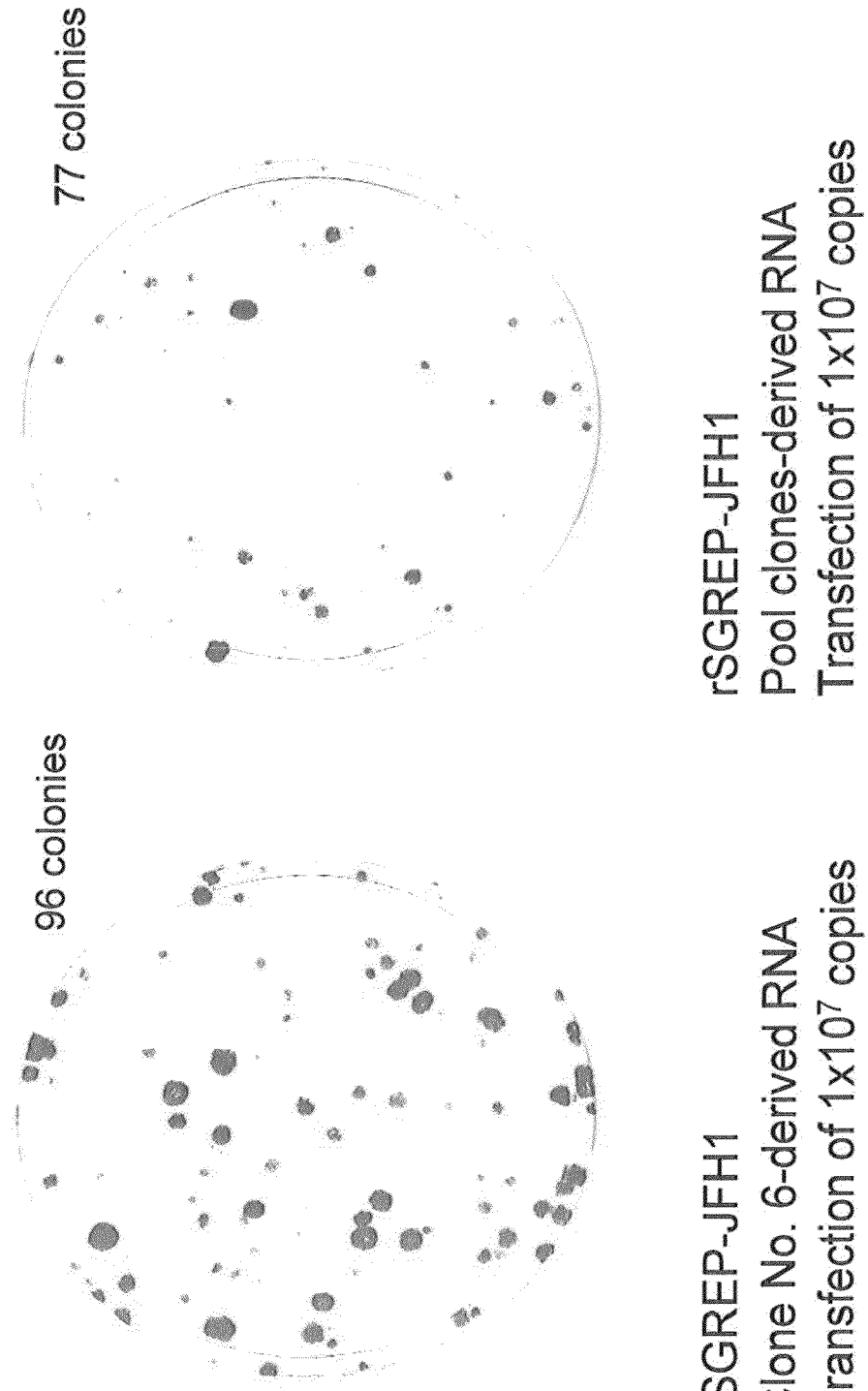
FIG. 7 shows photographs showing colony formation when total cellular RNA derived from the replicon-replicating cell clone, which had been established by transfection of rSGREP-JFH1, was retransfected to another Huh7 cells. The photograph on the left shows that the formation of 96 colonies was observed as a result, when using the total cellular RNA derived from the replicon-replicating cell clone No. 6. The photograph on the right shows that the formation of 77 colonies was observed as a result, when using the total cellular RNA derived from the pool clones. In both cases, RNA was retransfected in an amount containing $1 \times 10^7$ copies of the replicon RNA.

Next, aliquots of total cellular RNAs extracted from clone 6 (among the above-mentioned replicon-replicating cell clones) and pool clones (prepared by collecting replicon-replicating cells that had formed colonies from whole one dish and culturing them) were each introduced into another Huh7 cells by retransfection. Total cellular RNA used for the transfection was prepared to contain $1 \times 10^7$ copies of replicon RNA based on the number of copies of the above-determined replicon RNA. Transfection was performed as described in (C) above, and then selective culture was performed under G418 concentration conditions of 1 mg/ml. Thus, the colony formation of the replicon-replicating cells was observed (FIG. 7). The colony-forming ability in this case was 1 colony or more per $1 \times 10^6$ copies of the replicon RNA used for transfection, when it was calculated from the number of colonies obtained.

On the other hand, the number of copies of in vitro synthetic RNA that had been synthesized in vitro using pSGREP-JFH1 as a template and T7 RNA polymerase was approximately $2 \times 10^{11}$ copies/μg·RNA, when calculated based on the weight and the length of the RNA. The colony-forming ability in the case of using the in vitro synthetic RNA for transfection in a manner similar to the above method was 1 colony per $5 \times 10^7$ copies. These results revealed that when RNA derived from cells extracted from replicon-replicating cells and in vitro synthetic RNA were each transfected to Huh7 cells as replicon RNA in the same number of copies, the use of the replicon RNA replicated within Huh7 cells resulted in colony-forming ability approximately 50 times higher than that of the in vitro synthetic RNA.

Example 4

(F) Detection of Replicon RNA

According to (E) above, cell clones [clones Nos. 1 to 11] were established by retransfection of total RNA that had been obtained from the replicon-replicating cell clone established by transfection of rSGREP-JFH1 to Huh7 cells to another Huh7 cells, From the established cell clones and pool clones (prepared by collecting cell clones that had formed colonies from whole one dish and then culturing them), respectively, total RNAs were extracted by an acidic phenol extraction method. Subsequently the total RNAs were analyzed by the Northern blot method using a pSGREP-JFH1-specific probe as a probe. As control, total RNA extracted similarly from untransfected Huh7 cells (in FIG. 8, denoted as "Huh7"), a sample prepared by adding $10^7$ copies of replicon RNA synthesized in vitro to the total RNA extracted from Huh7 cells (in FIG. 8, denoted as "$10^7$"), and a sample (in FIG. 8, denoted as "$10^8$") prepared by adding $10^8$ copies of replicon RNA synthesized in vitro to the total RNA extracted from Huh7 cells, were used. In FIG. 8, 1 to 11 represent cell clone Numbers.

Figure 8:
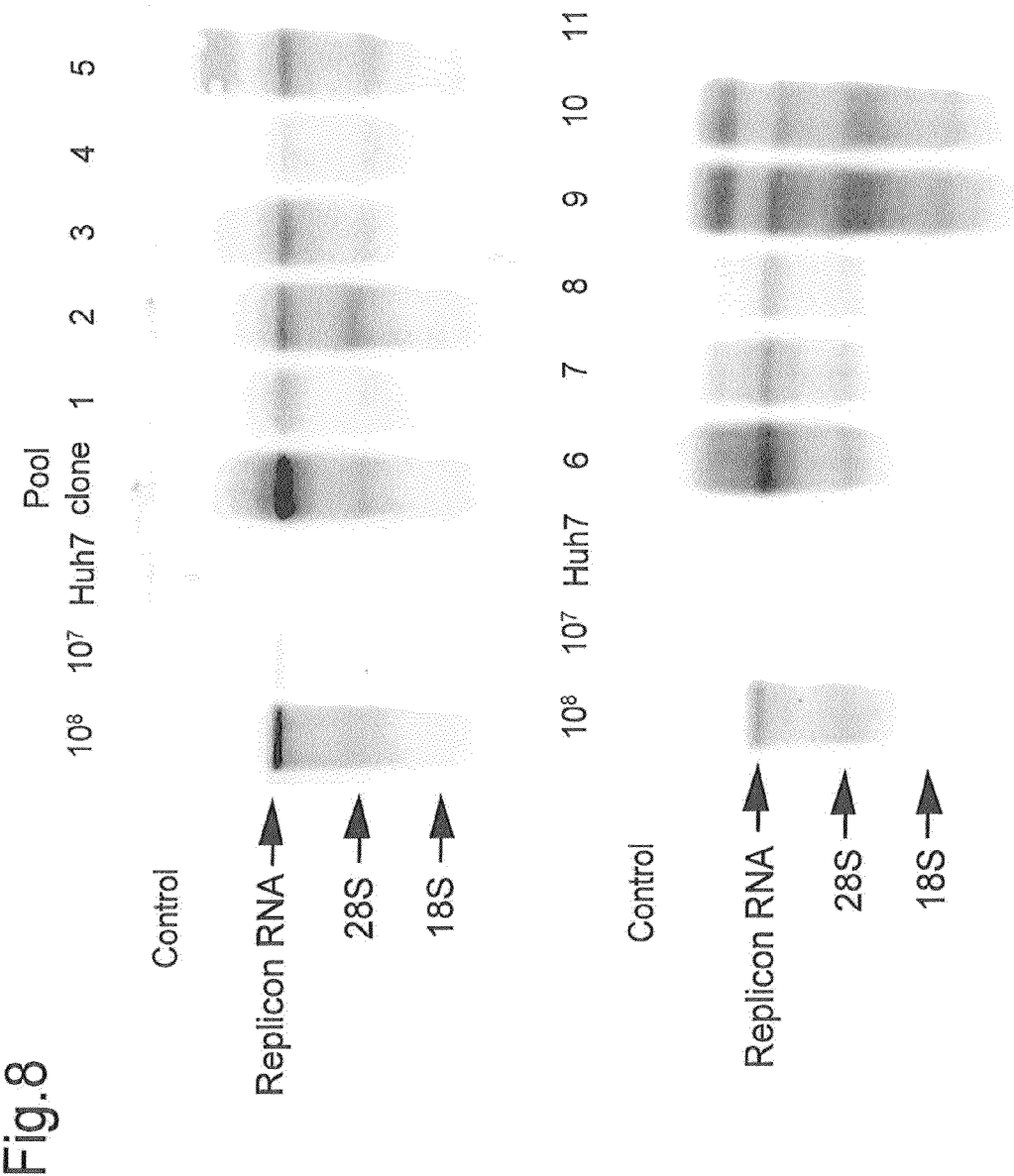
FIG. 8 shows photographs showing the results of detecting by the Northern blot method using an rSGREP-JFH1-specific probe for the total RNA derived from a cell clone that had been obtained by retransfecting the total cellular RNA (derived from the replicon-replicating cell clone established by transfection of rSGREP-JFH1) into another Huh7 cells. Explanation of the lanes is as follows. $10^8$ represents sample prepared by adding $10^8$ copies of the replicon RNA synthesized in vitro to total RNA extracted from Huh7 cells. $10^7$ represents sample prepared by adding $10^7$ copies of the replicon RNA synthesized in vitro to total RNA extracted from Huh7 cells. Huh7, total RNA extracted from untransfected Huh7 cells; pool clone, total RNA extracted from the pool clones; and 1-11, total RNA extracted from each of cell clones Nos. 1 to 11. "Replicon RNA" represents the electrophoresed position of a molecular weight marker indicating the size of rSGREP-JFH1, "28S" represents the same of a ribosomal RNA marker indicating the size of molecular weight of 4.5 kb, and "18S" represents the same of a ribosomal RNA marker indicating the size of molecular weight of 1.9 kb.

As a result, RNA of approximately the same size as that of rSGREP-JFH1 was detected using a pSGREP-JFH1-specific probe (FIG. 8). Thus, it was confirmed that the replicon RNA from rSGREP-JFH1 that had been transfected at the beginning replicated and proliferated within the cell clones. In addition, it was shown that the cell clones differed from each other in the quantity of the replicated replicon RNA. In FIG. 8, for example, clones 2, 6, 9 and 10 contained high quantities of the replicated replicon RNA, and clones 4, 8 and 11 contained low quantities of the replicated replicon RNA.

Figure 9:
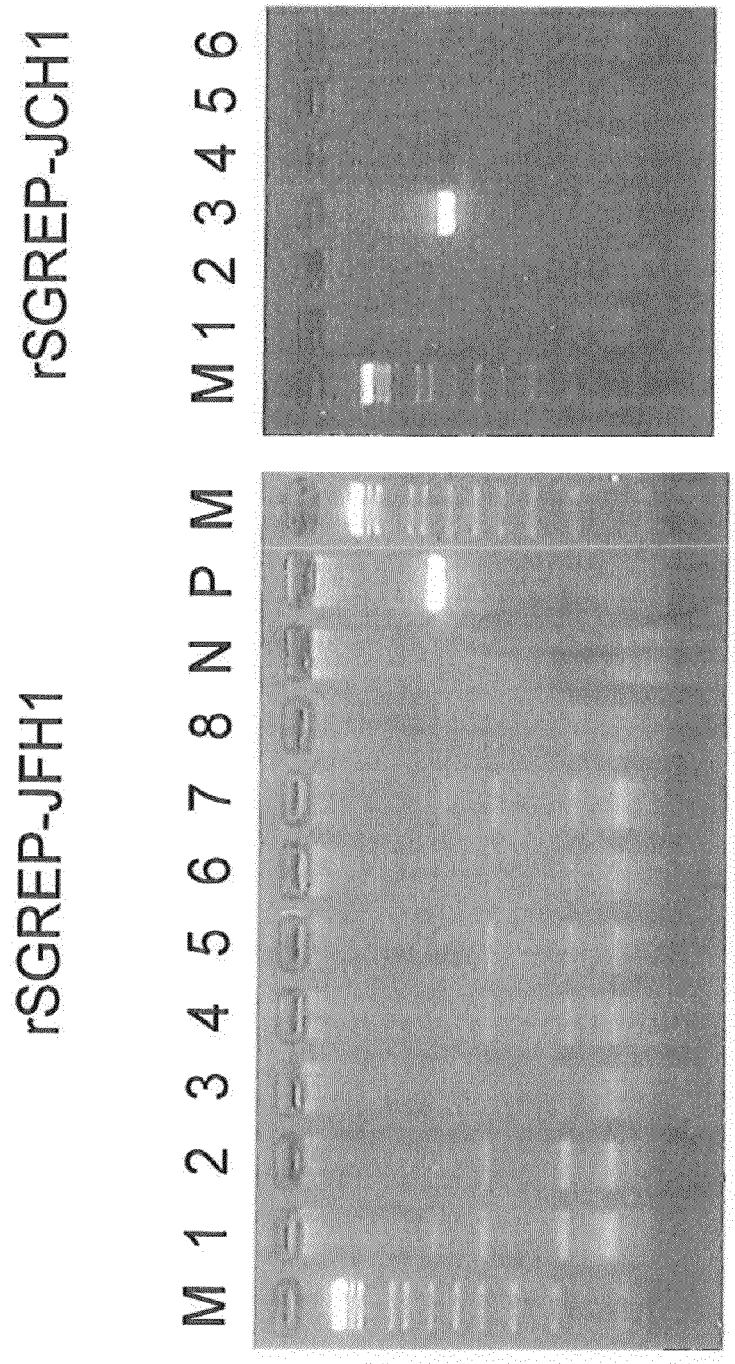
FIG. 9 shows photographs showing the presence or the absence of the incorporation of a neomycin resistance gene into the genomic DNA of a host cell in the cell clone to which rSGREP-JFH1- or rSGREP-JCH1-derived replicated replicon RNA was retransfected. Explanation of the lanes in the photograph on the left is as follows. M, DNA molecular weight marker; 1-8, rSGREP-JFH1-derived cell clones Nos. 1 to 8; N, untransfected Huh7 cells; and P, positive control (PCR amplification product of the neomycin resistance gene). Furthermore, explanation of the lanes in the photograph on the right is as follows. M, DNA molecular weight marker; and 1-6, rSGREP-JCH1-derived cell clones Nos. 1 to 6.

(G) Confirmation of the Presence or the Absence of the Incorporation of a Neomycin Resistance Gene into Genomic DNA For the cell clones that had been obtained by retransfection of replicon RNA as described in Example 3, PCR amplification was performed using neomycin resistance gene-specific primers; sense primer, NEO-S3: 5'-AACAAGATGGATTG-CACGCA-3' (SEQ ID NO: 16) and antisense primer, NEO-R: 5'CGTCAAGAAGGCGATAGAAG-3' (SEQ ID NO: 17), and the host cellular genomic DNA extracted from each of the cell clones as a template, in order to confirm that the resistance of each of the cell clones against G418 was not due to the incorporation of the neomycin resistance gene into the genome. The cell clones used herein were the cell clones Nos. 1 to 8 obtained by retransfection of rSGREP-JFH1-derived replicated replicon RNA (rSGREP-JFH1-derived cell clones Nos. 1 to 8), and cell clones Nos. 1 to 6 obtained by retransfection of rSGREP-JCH1-derived replicated replicon RNA (rSGREP-JCH1-derived cell clones Nos. 1 to 6). As a result, as shown in FIG. 9, in the eight examined rSGREP-JFH1-derived cell clones, positive clones showing the amplification of the neomycin resistance gene were not observed. For rSGREP-JCH1-derived cell clones, only 1 out of the 6 examined clones was positive (in FIG. 9, lane 3 in the right photograph). It was considered that this positive clone had acquired G418 resistance by the incorporation of the neomycin resistance gene in rSGREP-JCH1-derived replicated replicon RNA into the genomic DNA of the host cells. Thus, in the positive clone, unlike other clones, it was thought that the replicon RNA itself did not autonomously replicate within the cells. This was confirmed by the results of the experiment shown in the next (H) that no HCV proteins were detected from the positive clone.

(H) Detection of HCV Protein

Figure 10:
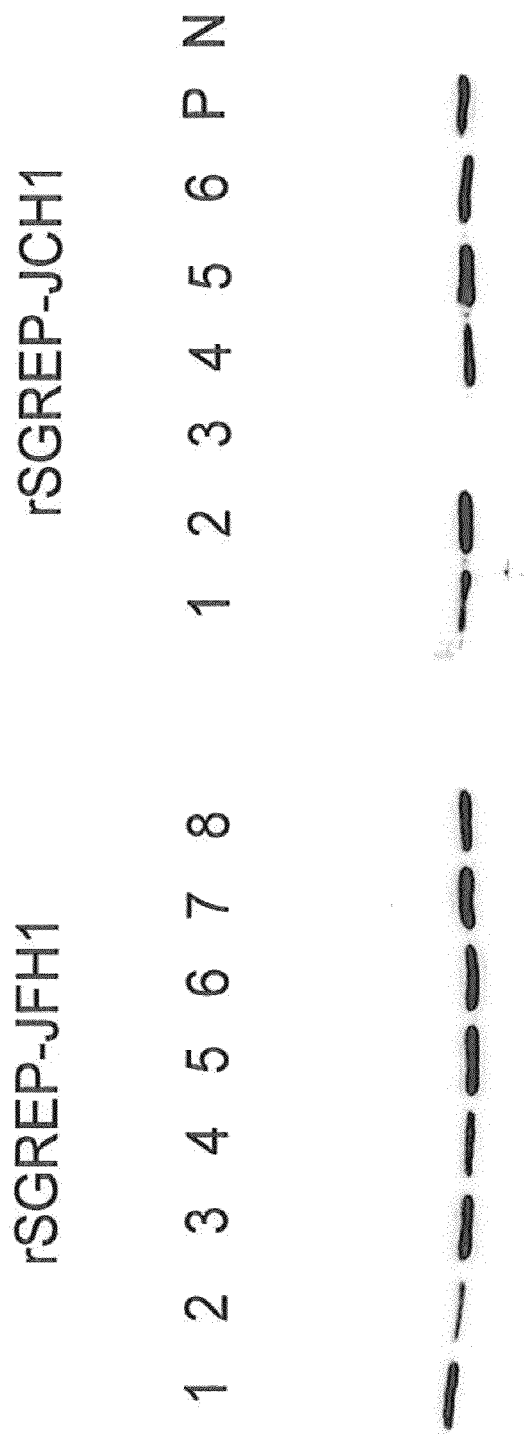
FIG. 10 shows photographs showing the results of detecting NS3 protein expressed in the cell clone that was retransfected with rSGREP-JFH1- or rSGREP-JCH1-derived replicated replicon RNA. Lanes 1 to 8 of the photograph on the left represent rSGREP-JFH1-derived cell clones Nos. 1 to 8. Lanes 1-6 of the photograph on the right represent rSGREP-JCH1-derived cell clones Nos. 1 to 6. Lane P of the photograph on the right represents NS3 protein (positive control) and N represents protein extracted from untransfected Huh7 cells (negative control).

Protein was extracted from rSGREP-JFH1- and rSGREP-JCH1-transfected cell clones by a standard procedure, and then analyzed by SDS-PAGE and Western blot method (FIG. 10). The examined cell clones were the same as those used in (G) above: rSGREP-JFH1-derived cell clones Nos. 1 to 8 and rSGREP-JCH1-derived cell clones Nos. 1 to 6. In addition, a cellular extract from the cell obtained by transiently transfecting expression plasmid DNA containing NS3 gene into Huh7 cells was regarded as a positive control (NS3 protein). Furthermore, a protein extracted from the untransfected Huh7 cells was used as a negative control. A protein sample extracted from each cell clone was blotted onto a PVDF membrane (Immobilon-P, Millipore), and then detection of NS3 protein encoded by replicated replicon RNA was performed using anti-NS3-specific antibody (provided by Dr, Moradpour; Wolk B, et al, J. Virology. 2000, 74: 2293-2304). As shown in FIG. 10, in rSGREP-JFH1-derived cell clones Nos. 1 to 8 and rSGREP-JCH1-derived cell clones Nos. 1, 2 and 4 to 6, proteins of the same size as those of the positive control were detected. In rSGREP-JCH1-derived cell clone No. 3 (the clone detected as a positive clone in (G) above), no expression of NS3 protein was detected. That is, in rSGREP-JCH1-derived cell clone No. 3, no replication of replicon RNA was confirmed. NS3 protein was not detected in the untransfected Huh7 cells, revealing that in cell clones wherein NS3 protein was detected, the transfected replicon RNA autonomously replicated so that NS3 protein was expressed.

Moreover, by the use of the serum of a hepatitis C patient as an antibody, the expression of NS5a protein from the replicon RNA was also confirmed in each cell clone for which the expression of NS3 protein had been confirmed as described above.

Based on the results of (G) and (H) above, it was confirmed that replicon RNAs were replicated in the cell clones established by transfection of the replicon RNA.

Example 5

(I) Analysis of Adaptive Mutation

According to descriptions of Example 3, total RNA obtained from the replicon-replicating cell clones established through the transfection of rSGREP-JFH1 into Huh7 cells was re-transfected to another Huh7 cells, thereby establishing 21 cell clones. Total RNA was extracted from each of these cell clones by a standard procedure. cDNA corresponding to the replicon RNA was synthesized using the total RNA as a template, reverse transcriptase Superscript II (Invitrogen) and primer 9641 R-IH (5'-GCACTCTCTGCAGTCATGCG-GCTCACGGAC-3' (SEQ ID NO: 18)). The composition of a reaction solution for the synthesis of cDNA by reverse transcription reaction is as shown below.

| Composition of Reaction Solution | Fluid Volume (μl) |
|---|---|
| 5x 1st strand Buffer | 4 |
| 2 mM dNTP | 5 |
| 0.1M DTT | 1 |
| 9651R-IH primer (100 μM) | 1 |
| DW (distilled water) | 6.5 |
| Sample RNA (2 mg/mL) | 1 |
| RNasin (Promega) (40 U/μL) | 0.5 |
| Superscript II RT (Invitrogen) | 1 |
| Total | 20 μl |

In cDNA synthesis reaction, the above reagents other than RNasin and Superscript II were mixed to prepare a first reaction solution. The solution was heated at 90° C. for 3 minutes, and then cooled on ice. Subsequently, RNasin and Superscript II were added to this reaction solution, and then the solution was allowed to react at 42° C. for 1 hour, followed by another reaction at 70° C. for 15 minutes.

Furthermore, PCR amplification was performed using the thus obtained eDNA together with five primer sets by the following procedures, so that DNA amplification fragments covering almost all the regions of the replicon RNA were obtained. The primer sets used and regions amplified by each primer set are shown in Table 1 and Table 2 below.

TABLE 1

| Designation of amplified fragment | Primer set | | Amplified region |
|---|---|---|---|
| | Primer 1 | Primer 2 | |
| A/ | 42S-IH | 433R-neo | 41-470 |
| B/ | C/S17ssp | 4680R-IH | 28-3026 |
| C/ | 4534S-IH | 7279R-IH | 2880-5625 |
| D/ | 7198S-IH | 9367R-IH | 5544-7713 |
| E/ | 9247S-NF | 9576R-NF | 7597-7960 |

In Table 1, an amplified region is represented by nucleotide numbers in rSGREP-JFH1 (SEQ ID NO: 1) that the region corresponds to.

TABLE 2

| Primer designation | Nucleotide sequence (5'→3') | SEQ ID NO: |
|---|---|---|
| 42S-IH | CCCCTGTGAGGAACTACTGTCTTCACGC | SEQ ID NO: 19 |
| C/S17ssp | CCGGGAGAGCCATAGTGGTCTGCG | SEQ ID NO: 20 |
| 4534S-IH | CCACTCAAAGAAAAAGTGTGACGAGCTCGC | SEQ ID NO: 21 |
| 7198S-IH | GGCTTGGGCACGGCCTGA | SEQ ID NO: 22 |
| 9247S-NF | GCGGTGAAGACCAAGCTCAAACTCACTCCA | SEQ ID NO: 23 |
| 433R-neo | AGAACCTGCGTGCAATCCATC | SEQ ID NO: 24 |
| 4680R-IH | CCCGTCATGAGGGCGTCGGTGGC | SEQ ID NO: 25 |
| 7279R-IH | ACCAGCAACGGTGGGCGGTTGGTAATC | SEQ ID NO: 26 |
| 9367R-RI | GGCACGCGACACGCTGTG | SEQ ID NO: 27 |
| 9576R-NF | AGCTAGCCGTGACTAGGGCTAAGATGGAGC | SEQ ID NO: 28 |

The composition of a reaction solution in this PCR reaction is as follows.

| Composition of Reaction Solution | Fluid Volume (μl) |
|---|---|
| Primer 1 (10 μM) | 1.0 |
| Primer 2 (10 μM) | 1.0 |
| 2.5 mM dNTPs | 5.0 |
| 10× LA Buffer | 5.0 |
| MgCl$_2$ (25 mM) | 5.0 |
| LA Taq (TAKARA) (5 U/μl) | 0.3 |
| DW (distilled water) | 30.7 |
| Template cDNA | 2.0 |
| Total | 50 μl |

In addition, PCR reaction conditions are as follows: 95° C. for 2 minutes; 35 cycles of 98° C. for 10 seconds and then 68° C. for 8 minutes; and 72° C. for 7 minutes; after which the temperature is kept at 4° C.

The nucleotide sequence of each PCR product obtained as described above was determined, and then the RNA sequence corresponding to the DNA sequence was compared with the sequence of rSGREP-JFH1. The results are shown in Table 3.

TABLE 3

| Region | Synonymous substitution | Nonsynonymous substitution | Total number of mutations |
|---|---|---|---|
| NS3 | 0 | 5 | 5 |
| NS4A | 0 | 2 | 2 |
| NS4B | 0 | 3 | 3 |
| NS5A | 0 | 7 | 7 |
| NS5B | 3 | 5 | 8 |
| Total | 3 | 22 | 25 |

As shown in Table 3, total number of nucleotide mutations observed in 21 cell clones was 25. 22 of these mutations were nonsynonymous substitutions inducing amino acid mutation. Types of these mutations are as shown in Table 4. In addition, the positions of these mutations in the non-structural region are shown in FIG. 11.

TABLE 4

| | Mutation site | | | |
|---|---|---|---|---|
| Clone designation | Nucleotide No. | Nucteotide mutation | Amino acid mutation | Amino acid No. |
| C1 | 7098 | A⇒G | None | |
| | 7157 | A⇒G | Y⇒C | 2824 |
| C2 | 4955 | C⇒U | A⇒V | 2090 |
| C3 | 4936 | A⇒G | T⇒A | 2084 |
| | 5000 | A⇒G | Y⇒C | 2105 |
| | 7287 | A⇒G | None | |
| | 7288 | A⇒G | M⇒V | 2868 |
| C4 | 5901 | G⇒U | E⇒D | 2405 |
| | 6113 | A⇒U | H⇒L | 2476 |
| C5 | 2890 | A⇒G | K⇒E | 1402 |
| C6 | 7209 | A⇒G | None | |

Figure 11:
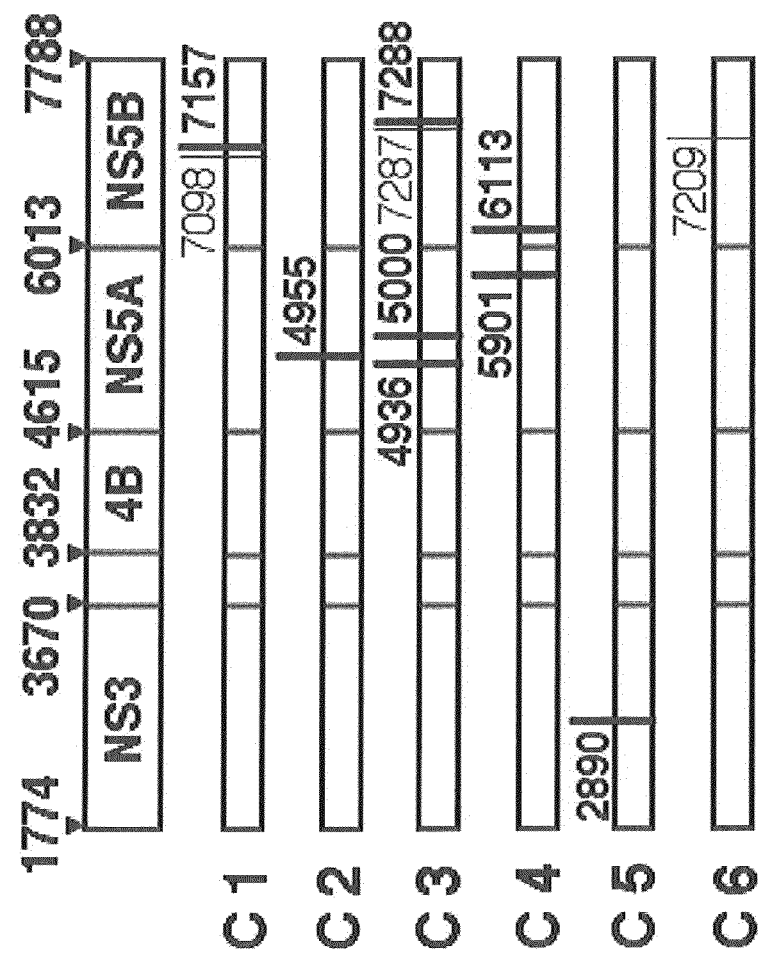
FIG. 11 shows the positions of nucleotide mutations in replicon RNAs obtained from 21 cell clones that were established through the re-transfection of rSGREP-JFH1-derived replicated replicon RNA into Huh7 cells. Mutation positions are indicated using bar lines shown with nucleotide numbers listed in Table 4. A thick bar line denotes nonsynonymous substitution and a thin bar line denotes synonymous substitution.
Figure 12:
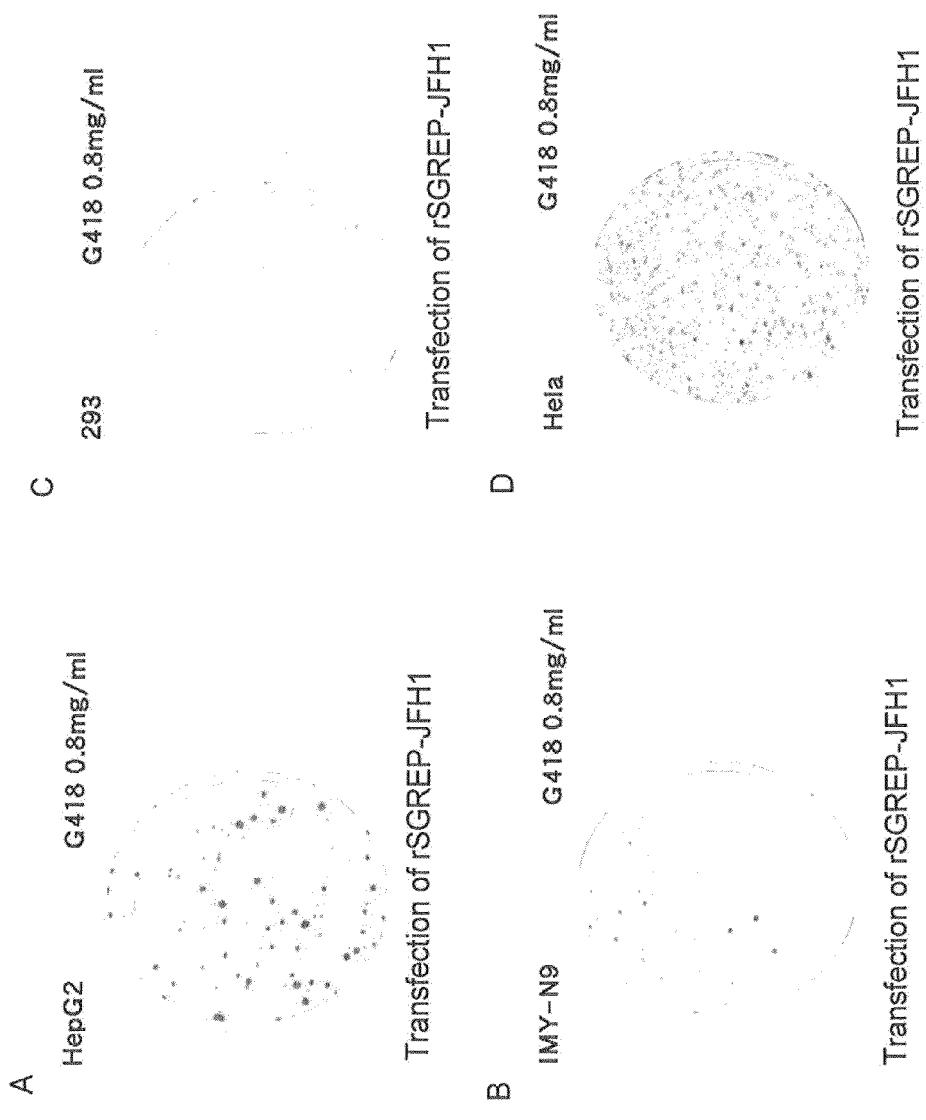
FIG. 12 shows photographs showing the results of transfection with rSGREP-JFH1 using A, HepG2 cells; B, IMY-N9 cells; C, 293 cells; or D, HeLa cells. 0.8 mg/ml G418 was added to each culture dish.

In Table 4 and FIG. 11, "C1 to C6" represent replicon-replicating cell clones C1 to C6 having replicon RNA found to have mutations. "Nucleotide No." shows the corresponding nucleotide numbers within the nucleotide sequence of replicon RNA rSGREP-JFH1 (SEQ ID NO: 1). "Amino acid No." shows the corresponding amino acid numbers within the amino acid sequence encoded by the JFH-1 clone (SEQ ID NO: 4). The types of nucleotides and amino acids at mutation sites are described according to their general notations. As shown in Table 4, in clone C2, a nucleotide corresponding to nucleotide No. 4955 of SEQ ID NO: 1 on the replicon RNA mutated from C (cytosine) to U (uracil), which results in a mutation of an amino acid corresponding to amino acid No. 2090 of SEQ ID NO: 4 from A (alanine) to V (valine).

Furthermore, mutation positions shown in FIG. 11 are shown with bar lines with the nucleotide numbers shown in Table 4. A thick bar line represents nonsynonymous substitution, and a thin bar line represents synonymous substitution.

There were 2 clones having no nucleotide mutations at all that cause amino acid mutations. When Northern blot analysis was conducted for the 2 clones, it was shown that in these 2 clones, the quantity of replicon RNAs replicated was lower than those in the cell clones that had replicated replicon RNAs having a nucleotide mutation that causes an amino acid mutation. Hence, it was considered that the nucleotide mutation causing an amino acid mutation within the replicon RNA was an adaptive mutation for increasing the replication efficiency of the replicon RNA in Huh7 cells.

Example 6

(J) Establishment of Replicon-Replicating Cell Clone Using Cells Other Than Huh7 Cells According to the method described in Example 1, rSGREP-JFH1 was transfected into some hepatic cancer cells other than Huh7 cells and non-liver-derived cells. The transfected cells were seeded into culture dishes and then cultured. Colony formation was observed and the number of colonies was counted. The cells used for transfection are as follows.
(1) HepG2 cells (representative hepatic cancer cells as well as Huh7 cells)
(2) IMY-N9 cells (established by Ito et al; fusion cells of HepG2 cells and human primary culture hepatic cells (Hepatology 2001, 34: 566-572))
(3) HeLa cells (human cervical cancer-derived cells (Can Cer Res. 1952, 12: 264-265))
(4) 293 cells (human fetal kidney-derived cells (Gen. Virol, 1977, 36; 59-72))

The results of transfection using HepG2 cells, IMY-N9 cells, HeLa cells or 293 cells, respectively, are shown in FIG. 12A to D. As shown in FIG. 12A to D, all HepG2 cells, IMY-N9 cells, HeLa cells, and 293 cells showed colony formation for rSGREP-JFH1-transfected cells.

For the established cell clones, detection of the replicated replicon RNA, confirmation of the presence or the absence of the incorporation of the neomycin resistance gene into host genomic DNA, and confirmation of the expression of HCV protein were performed as described later, (L) and (M). The cell clones, for which the replication of the replicon in the cells had been confirmed, were regarded as replicon-replicating cell clones. Specifically, it was demonstrated that the use of rSGREP-JFH1 also enables the preparation of HCV replicon-replicating cells using hepatic cancer cells other than Huh7 cells and non-hepatic cells with which the production of HCV replicon-replicating cells had previously been unsuccessful (Blight et al., Science, (2000) 290; 1972-1974).

Figure 13:
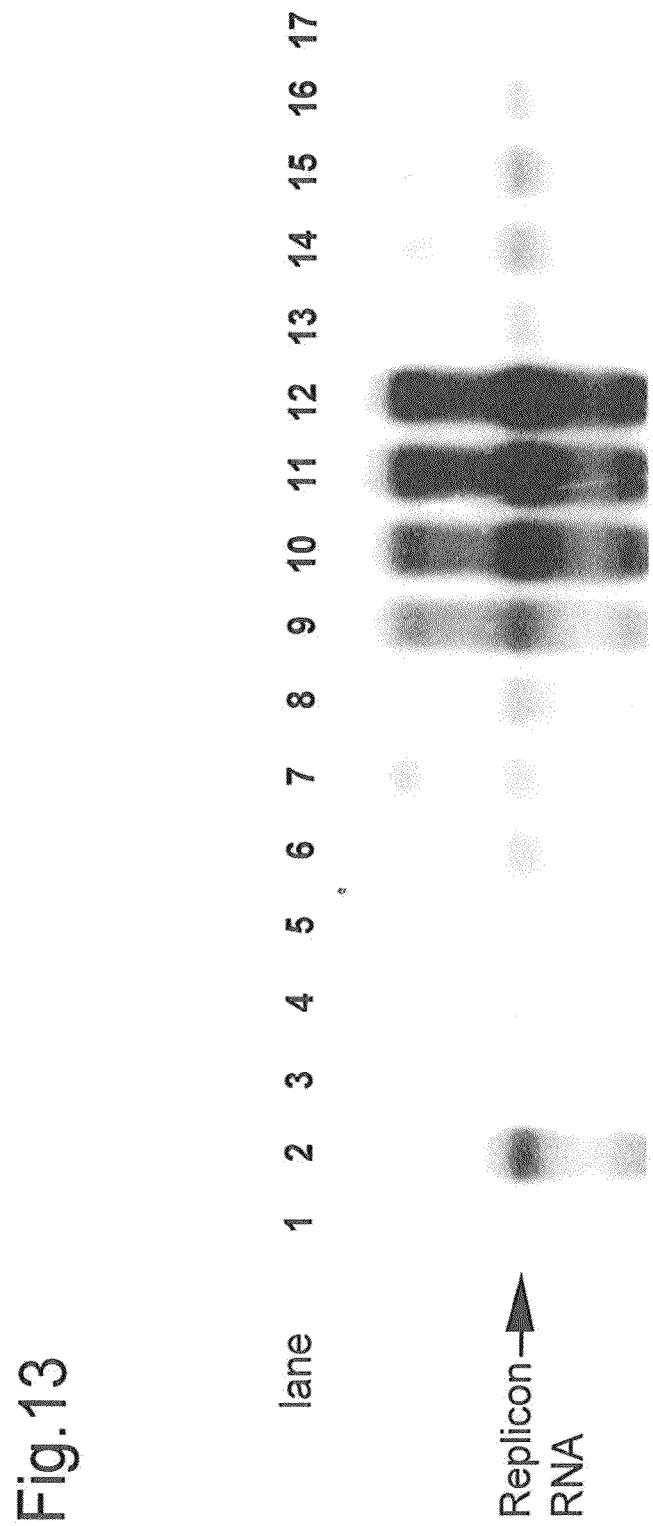
FIG. 13 shows photographs showing the results of performing Northern blotting for replicon-replicating cell clones. Lane 1, HepG2 (negative control); lane 2, $10^8$ copies of synthetic RNA; lane 3, $10^7$ copies of synthetic RNA; lane 4, Hep-IH-1 (derived from HepG2 cells); lane 5, 1-lep-IH-3 (derived from HepG2 cells); lane 6, Hep-IH-5 (derived from HepG2 cells); lane 7, Hep-IH-11 (derived from HepG2 cells); lane 8, Hep-IH-13 (derived from HepG2 cells); lane 9, IMY-IH-3 (derived from IMY-N9 cells); lane 10, IMY-IH-4 (derived from IMY-N9 cells); lane 11, IMY-IH-7 (derived from IMY-N9 cells); lane 12, IMY-IH-10 (derived from IMY-N9 cells); lane 13, cell pools containing 293-IH transfected therein (derived from 293 cells); lane 14, HeLa-IH-9 (derived from HeLa cells); lane 15, HeLa-IH-12 (derived from HeLa cells); lane 16, HeLa-IH-13 (derived from HeLa cells); and lane 17, HeLa (negative control).

(K) Detection of Replicon RNA in Replicon-Replicating Cells Using Cells Other Than Huh7 Cells Northern blot analysis was conducted according to a description of Molecular Cloning, A laboratory Manual, 2nd edition, J. Sambrook, E. F. Fritsch, T. Maniatis, Cold Spring Harbor Laboratory Press (1989). In accordance with the descriptions of the previous section (J), total RNA was extracted by the acidic phenol extraction method from each of the replicon-replicating cell clones that had been established by transfection of rSGREP-JFH1 into HepG2, IMY-N9 or HeLa cells respectively, and from pool clones of the replicon-replicating cells that had been established through transfection of rSGREP-JFH1 into 239 cells (prepared by collecting cell clones that had formed colonies from whole one dish and culturing them). Next, the total RNAs were analyzed by the Northern blot method using a pSGREP-JFH1-specific probe as a probe. As controls, total RNAs (lanes 1 and 17 in FIG. 13) extracted similarly from untransfected Huh7 cells and HepG2 cells, and RNA (lanes 2 and 3 in FIG. 13) prepared by adding $10^7$ copies or $10^8$ copies of the replicon RNA synthesized in vitro to total RNA extracted from Huh7 cells were used. As a result, RNA of approximately the same size of that of rSGREP-JFH1 was detected using a pSGREP-JFH1-specific probe (FIG. 13). Accordingly, it was confirmed that the replicon RNA derived from rSGREP-JFH1 that had been transfected at the beginning was replicated and proliferated within the cell clone. Furthermore, it was also revealed that the quantities of replicated replicon RNAs differed depending on cell type, and IMY-N9 cells were found to replicate the replicon RNA particularly efficiently. Moreover, it was revealed that the clones differed from each other in the quantity of the replicated replicon RNA.

Figure 14:
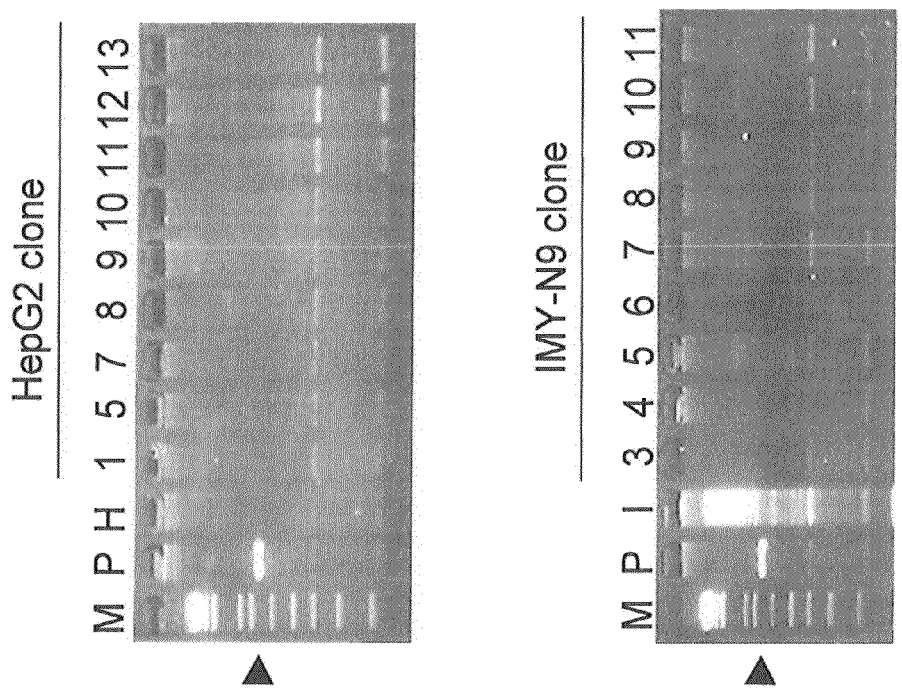
FIG. 14 shows photographs showing the results of electrophoresis performed for confirming the incorporation of the neomycin resistance gene into genomic DNA. For each genomic DNA of HepG2 replicon cells (upper section) and IMY-N9 replicon cells (lower section), detection of the neomycin resistance gene was performed by PCR analysis, M, DNA size marker; P, positive control; H, HepG2 cells; 1, IMY-N9 cells; and ▶, PCR product.

(L) Confirmation of the Presence or the Absence of the Incorporation of the Neomycin Resistance Gene into Genomic DNA For the thus established replicon RNA-replicating cell clone, PCR amplification was performed using neomycin resistance gene-specific primers (sense primer, NEO-S3: 5'-AACAAGATGGATTGCACGCA-3' (SEQ ID NO: 29), antisense primer, NEO-R: 5'-CGTCAAGAAGGCGATA-GAAG-3' (SEQ ID NO: 30)) and the host cellular genomic DNA extracted from each of the cell clones as a template, in order to confirm that the resistance of each of the cell clones against G418 was not due to the incorporation of the neomycin resistance gene into the genome. The cell clones used herein were the cell clones Nos. 1, 5, 7, 8, 9, 10, 11, 12 and 13 obtained by retransfection of rSGREP-JFH1-derived replicated replicon RNA into HepG2 cells, and the cell clones Nos. 3, 4, 5, 6, 7, 8, 9, 10 and 11 obtained by retransfection of rSGREP-JFH1-derived replicated replicon RNA into IMY-N9 cells. As a result, as shown in FIG. 14, in the nine examined cell clones obtained by introduction of rSGREP-JFH1 into HepG2 cells, a positive clone showing the amplification of the neomycin resistance gene was not observed. In the 9 examined cell clones obtained by introduction of rSGREP-JFH1 into IMY-N9 cells, a positive clone showing the amplification of the neomycin resistance gene was not observed.

A similar examination was performed for cell clones obtained by retransfection of rSGREP-JFH1-derived replicated replicon RNA into HeLa cells, and cell clones obtained by retransfection of rSGREP-JFH1-derived replicated replicon RNA into 293 cells, Then, a positive clone showing the amplification of the neomycin resistance gene was not observed, (M) Detection of HCV Protein Proteins were extracted from the established cell clones by a standard procedure, and then analyzed by SDS-PAGE and the Western blot method (FIG. 15). The cell clones examined in this case were the same as those used in the above section: the cell clones Nos. 1, 5, 7, 8, 9, 10, 11, 12 and 13 obtained by retransfection of rSGREP-JFH1-derived replicated replicon RNA into HepG2 cells, and the cell clones Nos. 3, 4, 5, 6, 7, 8, 9, 10 and 11 obtained by retransfection of rSGREP-JFH1-derived replicated replicon RNA into IMY-N9 cells. Furthermore, according to a previous report (Lehmann et. al., Science, (1999)), the HCV RNA replicon-replicating cell clone prepared by introducing rSGREP-JFH1 into HuH7 was regarded as a positive control (FIG. 15, lane 4-1, C6). Moreover, a protein extracted from untransfected cells was used as a negative control (FIG. 15, lane N). Protein samples extracted from each cell clone were blotted onto PVDF membranes (Immobilon-P, Millipore), and then detection of NS3 protein encoded by the replicated replicon RNA was performed using anti-NS3-specific antibody (provided by Dr. Moradpour; Wolk B, et al, J. Virology, 2000, 74: 2293-2304). As shown in the upper section in FIG. 15, a protein of the same size as that of the positive control was detected in the cell clones Nos. 1, 5, 7, 8, 9, 10, 11, 12 and 13 obtained by retransfection of rSGREP-JFH1-derived replicated replicon RNA, and in the cell clones Nos. 3, 4, 5, 6, 7, 8, 9, 10 and 11 obtained by retransfection of rSGREP-JFH1-derived replicated replicon RNA into IMY-N9 cells.

Moreover, by the use of the serum of a hepatitis C patient as an antibody, the confirmation of the expression of NS5a protein from the replicon RNA was performed for each cell clone that had been confirmed above to express NS3 protein. In this experiment, examination was performed in a manner similar to that in the case of the expression of NS3 protein, except using anti-NS5a antibody instead of the serum of the patient. As a result, as shown in the lower section in FIG. 15, a protein of the same size as that of the positive control was detected in the cell clones Nos. 1, 5, 7, 8, 9, 10, 11, 12 and 13 obtained by retransfection of rSGREP-JFH1-derived replicated replicon RNA, and the cell clones Nos. 3, 4, 5, 6, 7, 8, 9, 10 and 11 obtained by retransfection of rSGREP-JFH1-derived replicated replicon RNA into IMY-N9 cells.

When similar examination was performed for the cell clones obtained by retransfection of rSGREP-JFH1-derived replicated replicon RNA into HeLa cells, and the cell clones obtained by retransfection of rSGREP-JFH 1-derived replicated replicon RNA into 293 cells, the expression of NS3 and that of NS5a proteins could be confirmed.

As described above, it was confirmed that the replicon RNA was replicated in the cell clones that had been established through transfection of the replicon RNA.

Example 7

(N) Analysis of Adaptive Mutation

According to the descriptions of Example 3, total RNAs obtained from the replicon-replicating cell clones established through the transfection of rSGREP-JFH1 into HepG2 and HeLa cells were re-transfected into another cells of the each cell line, respectively, so that 14 cell clones were established for HepG2 cells and 8 cell clones were established for HeLa cells. From each of these cell clones, total RNA was extracted by a standard procedure. cDNA corresponding to the replicon RNA was synthesized using the total RNA as a template, reverse transcriptase Superscript II (Invitrogen) and a primer 9641R-IH (5'-GCACTCTCTGCAGTCATGCGGCTCACG-GAC-3' (SEQ ID NO: 31)). The composition of a reaction solution for the synthesis of cDNA by reverse transcription reaction is as shown below.

| Composition of Reaction Solution | Fluid Volume (μl) |
|---|---|
| 5× 1st strand Buffer | 4 |
| 2 mM dNTP | 5 |
| 0.1M DTT | 1 |
| 9651R-IH primer (100 μM) | 1 |
| DW (distilled water) | 6.5 |
| Sample RNA (2 mg/mL) | 1 |
| RNAsin (Promega)(40 U/μL) | 0.5 |
| Superscript II RT (Invitrogen) | 1 |
| Total | 20 μl |

In cDNA synthesis reaction, the above reagents other than RNAsin and Superscript 11 were mixed to prepare a first reaction solution. The first reaction solution was heated at 90° C. for 3 minutes, and then cooled on ice. Subsequently, RNAsin and Superscript II were added to the reaction solution, and then the solution was allowed to react at 42° C. for 1 hour, followed by another reaction at 70° C. for 15 minutes.

Furthermore, PCR amplification was performed using the thus obtained cDNA together with five primer sets by the following procedures, so that DNA amplification fragments covering almost all the regions of replicon RNA were obtained. The primer sets used and regions amplified by each primer set are shown in Table 5 and Table 6 below.

TABLE 5

| Designation of amplified fragment | Primer set | | Amplified region |
|---|---|---|---|
| | Primer 1 | Primer 2 | |
| A | 42S-IH | 433R-neo | 41-470 |
| B | C/S17ssp | 4680R-IH | 28-3026 |
| C | 4534S-IH | 7279R-IH | 2280-5625 |
| D | 7198S-IH | 9367R-IH | 5544-7713 |
| E | 9247S-NF | 9576R-NF | 7597-7966 |

In this table, an amplified region is represented by nucleotide numbers in rSGREP-JFH1 (SEQ ID NO: 1) that the region corresponds to.

TABLE 6

| Primer Designation | Nucleotide Sequence (5' to 3') | SEQ ID NO: |
|---|---|---|
| 43S-IH | CCCCTGTGAGGAACTACTGTCTTCACGC | SEQ ID NO: 32 |
| C/S17ssp | CCGGGAGAGCCATAGTGGTCTGCG | SEQ ID NO: 33 |
| 4534S-IH | CCACTCAAAGAAAAAGTGTGACGAGCTCGC | SEQ ID NO: 34 |
| 7198S-IH | GGCTTGGGCACGGCCTGA | SEQ ID NO: 35 |
| 9247S-NF | GCGGTGAAGACCAAGCTCAAACTCACTCCA | SEQ ID NO: 36 |
| 433R-neo | AGAACCTGCGTGCAATCCATC | SEQ ID NO: 37 |
| 4680R-IH | CCCGTCATGAGGGCGTCGGTGGC | SEQ ID NO: 38 |
| 7279R-IH | ACCAGCAACGGTGGGCGGTTGGTAATC | SEQ ID NO: 39 |
| 9367R-IH | GGAACGCGACACGCTGTG | SEQ ID NO: 40 |
| 9576R-NF | AGCTAGCCGTGACTAGGGCTAAGATGGAGC | SEQ ID NO: 41 |

The composition of a reaction solution in this PCR reaction is as follows.

| Composition of Reaction Solution | Fluid Volume (μl) |
|---|---|
| Primer 1 (10 μM) | 1.0 |
| Primer 2 (10 μM) | 1.0 |
| 2.5 mM dNTPs | 5.0 |
| 10× LA Buffer | 5.0 |
| MgCl$_2$ (25 mM) | 5.0 |
| LA Taq (TAKARA) (5 U/μl) | 0.3 |
| DW (distilled water) | 30.7 |
| Template cDNA | 2.0 |
| Total | 50 μl |

In addition, PCR reaction conditions are as follows: 95° C. for 2 minutes; 35 cycles of 98° C. for 10 seconds and then 68° C. for 8 minutes; followed by 72° C. for 7 minutes, after which the temperature is kept at 4° C.

The nucleotide sequence of each PCR product obtained as described above was determined, and then the RNA sequence corresponding to the DNA sequence was compared with the sequence of rSGREP-JFH1. The results are shown in Table 7 and Table 8.

TABLE 7

Analysis of adaptive mutation of JFH-1 replicon in HepG2 cells

| Clone | Mutation site | | Mutation | |
|---|---|---|---|---|
| | Nucleotide No. | Amino acid No. | Nucleotide | Amino acid |
| HepIH1 | 6826 | 2714 | C⇒A | Q⇒K |
| HepIH3 | 6887 | 2734 | C⇒A | T⇒N |
| HepIH5 | 6887 | | U⇒A | None |
| HepIH8 | 6580 | 2632 | U⇒A | S⇒T |
| | 7159 | 2825 | U⇒C | Y⇒H |
| HepIH9 | 3342 | | A⇒G | None |
| | 3594 | | C⇒A | None |
| | 7230 | 2848 | U⇒A | N⇒K |
| HepIH10 | 5052 | | U⇒C | None |
| | 6943 | 2753 | C⇒A | P⇒T |
| HepIH12 | None | | | |
| HepIH13 | 4302 | | C⇒U | None |
| | 5687 | 2334 | G⇒A | G⇒D |
| | 6110 | 2475 | A⇒G | Y⇒C |

As shown in Table 7, in the case of HepG2 cells, a total of 13 nucleotide mutations were observed in 8 cell clones, and 8 of these mutations were nonsynonymous substitutions that cause amino acid mutations. Types of these mutations are shown in Table 8. On the other hand, in the case of HeLa cells, a total of 7 nucleotide mutations were observed in 3 cell clones, and 5 of these mutations were nonsynonymous substitutions that cause amino acid mutations. Types of these mutations are shown in Table 8.

TABLE 8

Analysis of adaptive mutation of JFH-1 replicon in HeLa cells

| Clone | Mutation site | | Mutation | |
|---|---|---|---|---|
| | Nucleotide No. | Amino acid No. | Nucleotide | Amino acid |
| HeLaIH1 | None | | | |
| HeLaIH2 | 5550 | 2272 | U⇒C | S⇒P |
| | 6252 | | A⇒G | None |
| | 7182 | | U⇒C | None |
| | 7217 | 2844 | A⇒G | H⇒R |
| HeLaIH5 | 3643 | 1653 | A⇒G | M⇒V |
| | 5851 | 2389 | G⇒A | A⇒T |
| | 5914 | 2410 | G⇒A | E⇒K |

In Table 7, "HepIH No." represents clone numbers of replicon-replicating cell clones that have replicon RNA and have been cloned using HepG2 cells. "Nucleotide No." shows the corresponding nucleotide number in the nucleotide sequence (SEQ ID NO: 1) of replicon RNA rSGREP-JFH1. "Amino acid No." shows the corresponding amino acid number in the amino acid sequence (SEQ ID NO: 4) encoded by the JFH-1 clone. The types of nucleotides and amino acids at mutation sites are described according to their general notations. As shown in Table 7, for example, in clone HepIH1, a nucleotide corresponding to nucleotide No. 6826 of SEQ ID NO: on the replicon RNA mutated from C to A, so that an amino acid corresponding to amino acid No. 2714 of SEQ ID NO: mutated from Q to E. Similarly, in Table 8, "HeLaIH No." represents numbers of replicon-replicating cell clones that have replicon RNA and have been cloned using HeLa cells.

In addition, when Northern blot analysis was conducted for clones having no nucleotide mutations at all that cause amino acid mutations, it was shown that the quantity of replicon RNA replicated by the clones was lower than that of a cell clone replicating replicon RNA having a nucleotide mutation that causes an amino acid mutation. Hence, it was concluded that the nucleotide mutation in replicon RNA inducing an amino acid mutation was an adaptive mutation for increasing the replication efficiency of replicon RNA in cells.

INDUSTRIAL APPLICABILITY

The replicon-replicating cells according to the present invention can be utilized as a culture system for the continuous production of HCV genotype 2a-derived RNA and HCV protein. Moreover, the replicon-replicating cells according to the present invention are useful as a test system for screening for various substances affecting the replication of HCV and/or the translation into HCV protein.

All publications, patents and patent applications cited herein are incorporated herein by reference in their entirety.

SEQUENCE LISTING FREE TEXT

SEQ ID NO: 1. Explanation of artificial sequence: replicon
SEQ ID NO: 2. Explanation of artificial sequence: replicon
SEQ ID NO: 7. Explanation of artificial sequence: replicon
SEQ ID NOS: 8 to 12. Explanation of artificial sequences: synthetic RNA
SEQ ID NOS: 13 to 41. Explanation of artificial sequences: synthetic DNA

The invention claimed is:

1. A replicon RNA, comprising a nucleotide sequence containing at least the 5' untranslated region, the nucleotide sequence encoding NS3 protein, NS4A protein, NS4B protein, NS5A protein and NS5B protein and the 3' untranslated region of the genomic RNA of hepatitis C virus of genotype 2a strain JFH-1, and further containing a nucleotide sequence encoding a viral protein from the genomic RNA of an HCV strain or HCV genotype other than JFH-1.

2. The replicon of claim 1, said replicon further containing either one or both of a selection marker gene and/or a reporter gene.

3. The replicon of claim 1, wherein said HCV strain or HCV genotype other than JFH-1 is HCV-1, HCV-H, HC-J1, HCT-18, DK-7, US11, S14, HCT23, HCV-Th, DR1, DR4, HCT27, S18, SW1, DK9, H90, TD-6E1, 59, HCV-BK, T10, DK1, HC-J4, HCV-J, HK3, HK8, HK5, HCV-G3, IND5, IND8, P10, D1, D3, SW2, T3, S45, SA10, US6, HCV-JK1, HCV-JK4, HCV-JK3, HCV-JK2, HCV-JT, HC-J2, HCV-T, HK4, HC-G9, Z1, T4, T9, US10 HC-J5, T2, HC-J7, DK11, SW3, DK8, T8, HC-J8, S83, HK2, HC-J6, HC-J8, BEBE1, HCV-J6, HCV-J8, HD10-2, BR36-9, S52, S54, 82, BR33-1, HK10, DK12, HCV-TR, BA-1, BA-2, DK13, Z1, Z4, Z6, Z7, HK2, SA1, SA4, SA5, SA7, SA13, SA6, NZL1, SA30, EG-13, HCV-K3a/650, ED43, EUH1480, EUHK2, Th580, VN235, VN405, VN004, JK049, JK046, JCH-1, JCH-2, JCH-3, JCH-4, JCH-5, JCH-6, J6CF, or H77.

* * * * *

```
                         SEQUENCE LISTING

<160> NUMBER OF SEQ ID NOS: 41

<210> SEQ ID NO 1
<211> LENGTH: 8024
<212> TYPE: RNA
<213> ORGANISM: Artificial Sequence
<220> FEATURE:
<223> OTHER INFORMATION: HCV-derived synthetically created RNA replicon
      rSGREP-JFH1 sequence

<400> SEQUENCE: 1 accugcccu  aauaggggcg  acacuccgcc  augaaucacu  ccccugugag  gaacuacugu       60
cuucacgcag  aaagcgccua  gccauggcgu  uaguaugagu  gucguacagc  cuccaggccc     120 cccuccccg  ggagagccau  aguggucugc  ggaaccggug  aguaccggg  aauugccggg       180 aagacugggu  ccuuucuugg  auaaacccac  ucuaugcccg  gccauuuggg  cgugcccccg     240
```

```
caagacugcu agccgaguag cguugggung cgaaaggccu uguggulacug ccugauaggg      300 cgcuugcgag ugccccggga ggucucguag accgugcacc augagcacaa auccuaaacc      360
ucaaagaaaa accaaaagaa acaccaaccg ucgcccaaug auugaacaag auggauugca      420
cgcagguucu ccggccgcuu gguggagag gcuauucggc uaugacuggg cacaacagac       480
aaucggcugc ucugaugccg ccguguuccg gcugucagcg caggggcgcc cgguucuuuu      540
ugucaagacc gaccugugccg gugcccugaa ugaacugcag gacgaggcag gcggcuauc      600 guggcuggcc acgacgggcg uuccuugcgc agcugugcuc gacguuguca cugaagcggg      660
aagggacugg cugcuauugg gcgaagugcc ggggcaggau uccugucau ucaccuugc       720 uccugccgag aaaguaucca ucauggcuga ugcaaugcgg cggcugcaua cgcuugaucc      780
ggcuaccugc ccauucgacc accaagcgaa acaucgcauc gagcgagcac guacucggau     840
ggaagccggu cuugucgauc aggaugaucu ggacgaagag caucaggggc ucgcgccagc     900
cgaacuguuc gccaggcuca aggcgcgcau gcccgacggc gaggaucucg ucgugaccca     960
uggcgaugcc ugcuugccga auaucaluggu ggaaaaluggc cgcuuuucug gauucaucga   1020
cuguggccgg cugggugugg cggaccgcua ucaggacaua gcguuggcua cccgugauau   1080
ugcugaagag cuuggcggcg aaugggcuga ccgcuuccuc gugcuuluacg guaucgccgc    1140 ucccgauucg cagcgcaucg ccuucuaucg ccuucuugac gaguucuucu gaguuluaaac    1200 ccucucccuc ccccccccu aacguuacug gccgaagccg cuuggaauaa ggccggugug     1260
cguuugucua uauguuauuu uccaccauau ugccgucuuu uggcaaugug agggcccgga    1320
aaccuggccc ugucuucuug acgagcauuc cuaggggucu uccccucuc gccaaaggaa     1380 ugcaaggucu guugaaugc gugaaggaag caguccccucu ggaagcuucu ugaagacaaa    1440
caacgucugu agcgacccuu ugcaggcagc ggaaccccc accggcgac aggugccucu      1500 gcggccaaaa gccacguagua uaagauacac cugcaaaggc ggcacaaccc cagugccacg    1560
uugugaguug gauaguugug gaaagagaca aauggcucuc cucaagcgua ucaacaagg      1620 ggcugaagga ugcccagaag guacccaulu guaugggauc ugaucggggg ccucggugca     1680 caugculuuac augugulluuag ucgaggulaa aaaaacgucu aggcccccg aaccacgggg    1740 acgugguuuu ccuuugaaaa acacgaugau accauggcuc ccaucacugc uuaugcccag    1800
caaacacgag gccuccuggg cgccauagug gugagulauga cggggcguga caggacagaa   1860
caggccgggg aaguccaaau ccugucaca gucucucagu ccuuccucgg aacaaccauc    1920
ucggggguuu ugugglgacugu ulaccacggla gcuggcaaca agacucuagc cggcuuacgg   1980 ggulccgguca cgcagaugla ucgcgagugcu gaggggggaculu ugguaggcug gcccagcccc   2040 ccuggggacca agucuuugga gccgulgcaag ugulggagccg ucgaccuaula ucuggucacg    2100 cggaacgculg aulgcuaulccc ggcuuccggaga cgcggggaca agcggggagc auugcucucc  2160
ccgagacccg uuucgaccuu gaagggggucc ucgggggggc cggulgculcug cccuagggggc   2220 cacgulcguulg ggcuculluccg agcagculgulug ugculcucggggg gculggccaa auccaulcgau  2280 uucaulccccg uluglagacaculu cgacgulugulu acaaggulucuc ccacuuluucag ugacaacagc 2340 acgccaccgg culguglcccca gaccuaucag gulcgggulaculu ugcaulgculccc aacuggcagu    2400 ggaaagagca ccaaggulcccc ugulcgcgulaulu gccgcccagg ggulacaaagu acugulugculu    2460 aaccccculcgg ulagculgulccac ccugggguuu gggggcgulacc ulauccaaggulc acaugggcaulc  2520 aauccccaaca uluaggacugg agulcaggacc gugulaugaccg gggaggccau cacguacuccc    2580 acaulauggulca aauuucucgc cgaulggggggc ulgcgculagulcg gulcgulccaul

-continued

```
ugcgaugaau gccacgcugu ggaugcuacc uccauucucg gcaucggaac gguccuugau    2700
caagcagaga cagccggggu cagacuaacu gugcuggcua cggccacacc ccccgggguca   2760 gugacaaccc cccaucccga uauagaagag guaggccucg ggcgggaggg ugagauccccc   2820 uucuauggga gggcgauucc ccuauccugc aucaagggag ggagacaccu gauuuucugc    2880
cacucaaaga aaaagugaug cgagcucgcg gcggcccuuc ggggcauggg cuugaaugcc    2940
guggcauacu auagagggu ggacgucucc auaauaccag cucagggaga uguggugguc     3000
gucgccaccg acgcccucau gacggggguac acuggagacu uugacuccgu gaucgacugc   3060
aauguagcgg ucacccaagc ugucgacuuc agccuggacc ccaccuucac uauaaccaca    3120 cagacuguccu cacaagacgc ugucucacgu agucagcgcc gcgggcgcac agguagagga   3180
agacagggca cuuauaggua uguuccacu ggugaacgag ccucaggaau guuugacagu     3240
guagugcuuu gugagugcua cgacgcaggg gcugcguggu acgaucucac accagcggag   3300
accaccguca ggcuuagagc guauuucaac acgcccggcc uacccgugug ucaagaccau    3360
cuugaauuuu gggaggcagu uuucaccggc cucacacaca uagacgccca cuuccucucc    3420
caaacaaagc aagcggggga gaacuucgcg uaccuaguag ccuaccaagc uacgugugc     3480 gccagagcca aggccccucc cccguccugg gacgccaugu ggaagugccu ggcccgacuc    3540
aagccuacgc uugcgggccc cacaccucuc cuguaccguu ugggcccuau uaccaaugag    3600
gucacccuca cacacccugg gacgaaguac aucgccacau gcaugcaagc ugaccuugag    3660
gucaugacca gcacgugggu ccuagcugga ggagguccugg cagccgucgc cgcauauugc    3720
cuggcgacug gaugcguuuc caucaucggc cgcuugcacg ucaaccagcg agucgucguu    3780
gcgccggaua aggaggvccu guaugaggcu uuugaugaga uggaggaaug cgccucuagg    3840
gcggcucuca ucgaagaggg gcagcggaua gccgagaugu ugaaguccaa gauccaaggc    3900
uugcugcagc aggccucuaa gcaggcccag gacauacaac ccgcuaugca ggcuucaugg    3960
cccaaagugg aacaauuuug ggccagacac auguggaacu caauuagcgg cauccaauac    4020
cucgcaggau ugucaacacu gccagggaac cccgcggugg cuuccaugau ggcauucagu    4080
gccgcccuca ccaguccguu gucgaccagu accaccaucc uucucaacau caugggaggc    4140
ugguuagcgu cccagaucgc accacccgcg ggggccaccg gcuuugucgu cagugggccug   4200 guggggggcu gccgugggcag cauaggccug gguaaggugc ugguggacau ccuggcagga   4260
uauggugcgg gcauuucggg ggcccucguc gcauucaaga ucaugucugg cgagaagccc    4320
ucuauggaag augucaucaa ucuacugccu ggauccugu cccgggagc ccuggugguug     4380 ggggucaucu gcgcggccau ucugcgccgc cacgugggac cggggaggg gcgguccaa     4440 uggaugaaca ggcuuauugc cuuugcuucc agaggaaacc acgucgcccc uacucacuac    4500
gugacggagu cggaugcguc gcagcgugug acccaacuac uuggcucucu uacuauaacc    4560
agccuacuca gaagacucca caauuggaua acugaggacu gccccauccc augcuccgga    4620
uccuggcucc gcgacgugug ggacggguu ugcaccaucu ugacagacuu caaaaauugg    4680
cugaccucua aauuguuccc caagcugccc ggccucccu ucaucucuug ucaaaagggg    4740
uacaaggguu gugggccgg cacuggcauc augaccacgc gcugcccuug cggcgccaac    4800
aucucuggca uguccgccu gggcucuaug aggaucacag ggccuaaaac cugcaugaac    4860
accuggcagg ggaccuuucc uaucaauugc uacacggagg ccagugcgc gccgaaaccc    4920 cccacgaacu acaagaccgc caucuggagg guggcggccu cggagaucgc ggaggugacg    4980
cagcaugggu cguacuccua guaacagga cugaccacug acaaucugaa aauuccuugc    5040
```

| | |
|---|---|
| caacuaccuu cuccagaguu uuucuccugg guggacggug ugcagaucca uagguuugca | 5100 |
| cccacaccaa agccguuuuu ccgggaugag gucucguucu gcguugggcu uaauuccuau | 5160 |
| gcugucgggu cccagcuucc cugugaaccu gagcccgacg cagacguauu gagguccaug | 5220 |
| cuaacagauc cgccccacau cacggcggag acugcggcgc ggcgcuuggc acggggauca | 5280 |
| ccuccaucug aggcgagcuc cucagugagc cagcuaucag caccgucgcu gcgggccacc | 5340 |
| ugcaccaccc acagcaacac cuaugacgug gacauggucg augccaaccu gcucauggag | 5400 |
| ggcggugugg cucagacaga gccugagucc agggugcccg uucggacuu ucucgagcca | 5460 |
| auggccgagg aagagagcga ccuugagccc ucaauaccau cggagugcau gcuccccagg | 5520 |
| agcggguuuc cacgggccuu accggcuugg gcacggccug acuacaaccc gccgcucgug | 5580 |
| gaaucgugga ggaggccaga uuaccaaccg cccaccguug cugguugugc cucccccccc | 5640 |
| cccaagaagg ccccgacgcc ucccccaagg agacgccgga cagugggucu gagcgagagc | 5700 |
| accauaucag aagcccucca gcaacuggcc aucaagaccu uggccagcc ccccucgagc | 5760 |
| ggugaugcag gcucguccac gggggcgggc gccgccgaau ccggcggucc gacguccccu | 5820 |
| ggugagccgg cccccucaga gacagguucc gccuccucua ugccccccu cgagggggag | 5880 |
| ccuggagauc cggaccugga gucugaucag guagagcuuc aaccuccccc caggggggg | 5940 |
| ggguaguagcuс ccgguucggg cucggggucu uggucuacuu gcccgagga ggacgauacc | 6000 |
| accgugugcu gcuccaugnc auacuccugg accggggcuc uaauaacucc cuguagcccc | 6060 |
| gaagaggaaa aguugccaau caacccuuug aguaacucgc uguugcgaua ccauaacaag | 6120 |
| guguacugua caacaucaaa gagcgccuca cagagggcua aaaagguaac uuuugacagg | 6180 |
| acgcaagugc ucgacgccca uuaugacuca gucuuaaagg acaucaagcu agcggcuucc | 6240 |
| aaggucagcg caaggcuccu caccuuggag gaggcgugcc aguugacucc accccauucu | 6300 |
| gcaagaucca aguauggauu cggggccaag gagguccgca gcuugcccgg gagggccguu | 6360 |
| aaccacauca aguccgugug gaaggaccuc cuggaagacc cacaaacacc aauucccaca | 6420 |
| accaucaugg ccaaaaauga ggugu ucgc gguggacccсg ccaagggggg uaagaaacca | 6480 |
| gcucgccuca ucguuuaccc ugaccucggc guccgggucu gcgagaaaau ggcccucuau | 6540 |
| gacauuacac aaaagcuucc ucaggcggua auggagcuu ccuauggcuu ccaguacucc | 6600 |
| ccugcccaac ggguggagua ucucuugaaa gcaugggcgg aaaagaagga ccccaugggu | 6660 |
| uuucguaug auacccgaug cuucgacuca accgucacug agagagacau caggaccgag | 6720 |
| gaguccauau accaggccug cucccugccc gaggaggccc gcacugccau acacucgcug | 6780 |
| acugagagac uuuacguagg agggcccaug uucaacagca agggucaaac cugcggguuac | 6840 |
| agacguugcc gcgccagcgg ggugcuaacc acuagcaugg guaacaccau cacaugcuau | 6900 |
| gugaaagccc uagcggccug caaggcgcg gggauaguug cgcccacaau gcugguaugc | 6960 |
| ggcgaugacc uaguagucau cucagaaagc caggggacug aggaggacga gcggaaccug | 7020 |
| agagccuuca cggaggccau gaccagguac ucugccccuc cugguagauc ccccagaccg | 7080 |
| gaauaugacc uggagcuaau aacauccugu uccucaaaug ugucugugc guugggcccg | 7140 |
| cggggccgcc gcagauacua ccugaccaga gacccaacca cuccacucgc ccgggcugcc | 7200 |
| ugggaaacag uuagacacuc ccccaucaau ucauggcugg aaacaucau ccaguaugcu | 7260 |
| ccaaccauau ggguucgcau ggccuaaug acacacuucu cuccauucu cauggccaa | 7320 |
| gacacccugg accagaaccu caacuuugag auguauggau caguauacuc cgugaauccu | 7380 |
| uuggaccuuc cagccauaau ugagagguua cacgggcuug acgccuuuuc uaugcacaca | 7440 |

-continued

| | |
|---|---|
| uacucucacc acgaacugac gcgggugggcu ucagcccuca gaaaacuugg ggcgccaccc | 7500 |
| cucagggugu ggaagagucg ggcucgcgca gucagggcgu cccucaucuc ccguggaggg | 7560 |
| aaagcggccg uuugcggccg auaucucuuc aauugggcgg ugaagaccaa gcucaaacuc | 7620 |
| acuccauugc cggaggcgcg ccuacuggac uuauccaguu gguucaccgu cggcgccggc | 7680 |
| gggggcgaca uuuucacag cgugucgcgc cccgacccc gcauuacu cuucggccua | 7740 |
| cuccuacuuu ucguaggggu aggccucuuc cuacuccccg cucgguagag cggcacacac | 7800 |
| uagguacacu ccauagcuaa cuguuccuuu uuuuuuuuuu uuuuuuuuuu uuuuuuuuuu | 7860 |
| uuuuuuuuuu cuuuuuuuuu uuuuucccuc uuucuucccu ucucaucuua uucuacuuuc | 7920 |
| uuucuuggug gcuccaucuu agcccuaguc acggcuagcu gugaaagguc cgugagccgc | 7980 |
| augacugcag agagugccgu aacggucuc ucugcagauc augu | 8024 |

<210> SEQ ID NO 2
<211> LENGTH: 8024
<212> TYPE: RNA
<213> ORGANISM: Artificial Sequence
<220> FEATURE:
<223> OTHER INFORMATION: HCV-derived synthetically created RNA Replicon rSGREP-JCH1

<400> SEQUENCE: 2

| | |
|---|---|
| acccgccccu aauagggggcg acacuccgcc augaaucacu ccccugugag gaacuacugu | 60 |
| cuucacgcag aaagcgucua gccauggcgu uaguaugagu gucguacagc cuccaggccc | 120 |
| cccccucccg ggagagccau aguggucugc ggaaccggug aguacaccgg aauugccggg | 180 |
| aagacugggu ccuuucuugg auaaacccac ucuaugcccg gccauuuggg cgugccccg | 240 |
| caagacugcu agccgaguag cguuggguug cgaaaggccu gugguacug ccugauaggg | 300 |
| ugcuugcgag ugcccggga ggucucuag accgugcacc augagcacaa aucccaaacc | 360 |
| ucaaagaaaa accaaaagaa acacuaaccg ucgcccaaug auugaacaag auggauugca | 420 |
| cgcagguucu ccggccgcuu ggguggagag gcuauucggc uaugacuggg cacaacagac | 480 |
| aaucggcugc ucugaugccg ccguguuccg gcugucagcg caggggcgcc cgguucuuuu | 540 |
| ugucaagacc gaccuguccg gugcccugaa ugaacugcag gacgaggcag cgcggcuauc | 600 |
| guggcuggcc acgacgggcg uuccuugcgc agcugugcuc gacguuguca cugaagcggg | 660 |
| aagggacugg cugcuauugg gcgaagugcc ggggcaggau cuccugucau cucaccuugc | 720 |
| uccugccgag aaaguaucca ucauggcuga ugcaaugcgg cggcugcaua cgcuugaucc | 780 |
| ggcuaccugc ccauucgacc accaagcgaa acaucgcauc gagcgagcac guacucggau | 840 |
| ggaagccggu cuugucgauc aggaugaucu ggacgaagag caucgggcgc ucgccagc | 900 |
| cgaacuguuc gccaggcuca aggcgcgcau gcccgacggc gaggaucucg ucgugaccca | 960 |
| uggcgaugcc ugcuugccga auaucauggu ggaaaauggc cgcuuuucug gauucaucga | 1020 |
| cugguggccgg cuggugugg cggaccgcua ucaggacaua gcguuggcua cccgugauau | 1080 |
| ugcugaagag cuuggcggcg aaugggcuga ccgcuuccuc gugcuuuacg guaucgccgc | 1140 |
| ucccgauucg cagcgcaucg ccuucuaucg ccuucuugac gaguucuucu gaguuuaaac | 1200 |
| ccucucccuc cccccccccu aacguuacug gcgaagccg cuggaauaa ggccggugug | 1260 |
| cguuugucua uauguuauuu uccaccauau ugccgucuuu uggcaaugug agggcccgga | 1320 |
| aaccuggccc ugucuucuug acgagcauuc cuaggggucu uucccucuc gccaaaggaa | 1380 |
| ugcaaggucu guugaaugc gugaaggaag caguuccucu ggaagcuucu ugaagacaaa | 1440 |

| | |
|---|---|
| caacgucugu agcgacccuu ugcaggcagc ggaaccccc accuggcgac aggugccucu | 1500 |
| gcggccaaaa gccacgugua aagauacac cugcaaaggc ggcacaaccc cagugccacg | 1560 |
| uugugaguug gauaguugug gaaagaguca aauggcucuc cucaagcgua uucaacaagg | 1620 |
| ggcugaagga ugcccagaag guaccccauu guauggauc ugaucggggg ccucggugca | 1680 |
| caugcuuuac auguguuuag ucgagguuaa aaaaacgucu aggcccccg aaccacgggg | 1740 |
| acgugguuuu ccuuugaaaa acacgauaau accauggccc ccaucaccgc uuacgcccag | 1800 |
| cagacacgag gucucuuggg cucuauagug gugagcauga cggggcguga aagacagaa | 1860 |
| caggccgggg aggucccaagu ccugcccaca gucacucagu ccuuccucgg aacauccauu | 1920 |
| ucggggucu uauggacugu uuaccacgga gcuggcaaca agacacuagc cggcucgcgg | 1980 |
| ggcccggucca cgcagaugua cucgagcgcc gaggggacu uggucgggug gcccagcccu | 2040 |
| ccugggacca aaucuuugga gccguguacg uguggagcgg ucgaccugua uuggucacg | 2100 |
| cggaacgcug augucauccc ggcucgaaga cgcggggaca agcggggagc gcugcucucc | 2160 |
| ccgagacccc uuucgaccuu gaaggggucc ucgggggggac cugugcuuug cccuagggc | 2220 |
| cacgcgucg gaaucuuccg ggcagcugug ugcucucggg guguggcuaa guccauagau | 2280 |
| uucauccccg uugagacgcu cgacaucguc acgcggucuc ccaccuuuag ugacaacagc | 2340 |
| acaccaccag cugugcccca gaccuaucag gugggguacu ugcacgcccc cacuggcagu | 2400 |
| ggaaaagca ccaaggucccc cgucgcguac gccgcccagg gguauaaagu gcuggugcuc | 2460 |
| aauccccucgg uggcugccac ccugggauuu gggggcguacu ugccaaaggc acuggcauc | 2520 |
| aaccccaaca uuaggacugg agucagaacu ugacgaccg gggagcccau acauacuccc | 2580 |
| acguauggua aauuccucgc cgaugggggc ugcgcaggcg gcgccuauga caucaucaua | 2640 |
| ugcgaugaau gccacucugu ggaugcuacc acuauucucg gcaucgggac aguccuugac | 2700 |
| caagcagaga cagccggggu caggcuaacu guacuggcca cggccacgcc ccccgggucg | 2760 |
| gugacaaccc cccaaucccaa uauagaggag guagcccucg gacaggaggg ugagaucccc | 2820 |
| uucuauggga gggcguuucc ccugucuuac aucaagggag ggaggcacuu gauuuucugc | 2880 |
| cacucaaaga aaaaguguga cgagcucgca acggcccuuc ggggcauggg cuugaacgcu | 2940 |
| guggcauauu acagagggu ggacgucucc auaauaccaa cucaaggaga uguggugguc | 3000 |
| guugccaccg acgcccucau gacggguau acuggagacu uugacuccgu gaucgacugc | 3060 |
| aacguagcgg ucacccaggc cguagacuuc agccuggacc ccaccuucac uauaaccaca | 3120 |
| cagacuguccc cgcaagacgc ugucucacgu agucagcgcc gagggcgcac ggguagagga | 3180 |
| agacugggca uuuauaggua uguuccacu ggugagcgag ccucaggaau guugacagu | 3240 |
| guaguacucu gugagugcua cgacgcagga gcugcuuggu augagcucuc accaguggag | 3300 |
| acgaccguca ggcucagggc guauuucaac acgccuggcu ugccugugug ccaggaccac | 3360 |
| cuugaguuuu ggggaggcagu uuucaccggc cucacacaca uagacgcuca uuccuuucc | 3420 |
| cagacaaagc agucggggga aaauuucgca uacuuaguag ccuaucaggc cacagugugc | 3480 |
| gccagggcca aagcgccccc cccgucugg acgucaugu ggaagugcuu gacucgacuc | 3540 |
| aagcccacgc uugugggccc uacaccucuc cuguaccguu ugggcucugu uaccaacgag | 3600 |
| gucacccuua cacacccccgu gacaaaauac aucgccacau gcaugcaagc ugaccucgag | 3660 |
| gucaugacca gcacguggu ccuggcuggg ggagucuuag cagccgucgc cgcguauugc | 3720 |
| uuagcgaccg ggugguuuc caucauuggc cguuuacaca ucaaccagcg agcugucguc | 3780 |
| gcuccggaca aggaggucuu cuaugaggcu uuugaugaga uggaggaaug ugccuccaga | 3840 |

```
gcggcucucc uugaagaggg gcagcggaua gccgagaugc ugaaguccaa gauccaaggc    3900
uuauugcagc aagccucuaa acaggcccag gacauacaac ccgcugugca agcuucgugg    3960
cccaagaugg agcaauucug ggccaaacau auguggaacu cauaagcgg cauucaguac     4020 cucgcaggac ugucaacacu gccagggaac ccugcugugg cuuccaugau ggcauucagc    4080
gccgcccuca ccagccgguu gucaacuagc accaccaucc uucuuaacau ucugggggc     4140 uggcuggcgu cccaaauugc gccacccgcg ggggccacug gcuuuguugu cagugcccug    4200
gugggagcug cuguuggcag cauaggcuug gguaaagugc uguggacau ccuggcaggg     4260 uauggugcgg gcauuucggg ggccucaguc gcguuuaaga ucaugucugg cgagaagccc    4320
uccauggagg augucaucaa cuugcugccu gggauucugu uccaggugc ucuggugguug    4380 ggagucaucu gcgcggccau ucugcgccgc caugugggac cggggaagg cgcgguccaa     4440 uggaugaaca ggcuuaucgc cuucgcuucc agaggaaacc acgucgcccc uacucacuac    4500
gugacggagu cggaugcguc gcagcgugue acccaacgc uuggcucucu cacuauaacu     4560 aguucuacuca ggagacuuca caacuggauc acugaggauu gccccaucc augcgccggc    4620 ucgugggcucc gcgaugugug ggacggguc uguaccaucc uaacagacuu uaagaacugg    4680 cugaccuucca agcuguuccc aaagaugccu ggccucccu uuaucucuug ccaaaggggg    4740
uacaagggcg uguggccggg cacuggcauc augaccacac gaugcccug cggcgccaac    4800 aucucuggca acgucccgcuu gggcucuaug agaaucacag acccaaaac cugcaugaac    4860 accuggcagg ggaccuuucc uaucaauugu auacagaag ccagugcuu gccgaaaccc    4920 gcguuaaacu ucaagaccgc caucuggaga guggcggccu cagaguacgc ggaagugacg    4980
cagcacggau cauaugccua uaaacaggg cugaccacug acaacuuaaa aguccuugc    5040 caaucccccu cuccagaguu uuucucuugg guggacggag uacaaauccca uaggouccgcc   5100 cccacaccaa agccguuuuu ccgggaugag gucucguuca gcguugggcu caauucauuu   5160
gucgucgggu ucagcuucc cuguaccccu gagcccgaca cugagguagu gaugucccaug   5220 cuaacagacc caucccauau cacggcggag gcugcagcgc ggcguuuagc gcgggguca    5280 cccccaucug aggcaagcuc cucagcgagc cagcugucgg cgccaucgcu gcgagccacc   5340
ugcaccaccc acgguaggac cuaugaugug gacaugggu augccaaccu guucauggg    5400 ggcggcguga uucggauaga gucugagucc aaaguggucg uucuggacuc ccucgacuca   5460
augaccgagg aagagggcga ccuugagccu ucaguaccau cggaguauau gcuccccagg   5520
aagagguucc caccggccuu accggcuugg gcgcggccug auuacaaccc accgcuugug   5580
gaaucgugga gaggccaga uuaccaacca cccacuguug cgggcugugc ucucccccc    5640 cccaaaaaga ccccgacgcc uccuccaagg agacgccgga caguggoucu gagcgagagc   5700 accauaggag augcccucca acagcuggcc aucaagaccu uggccagcc ccccccaagc   5760 ggcgauucag gccuuuccac ggggcgcgac ccgccgacu ccggcgaucg gacacccccu   5820
gacgaguugg cucuuucgga gacagguucu accuccucca ugccccccu cgaggggag    5880 ccugggggacc cagaccuuga gccugagcag guagagcuuc aaccuccucc caggggggag   5940
gaggcagcuc ccggcucgga cucgggguc uggucuacuu gcuccaggga ggaugacucc    6000 gucguguqgcu gcuccauguc auauuccugg accgggcuc uaauaacucc uuguagcccc    6060
gaagaggaaa aguugccaau uaacuccuug agcaacucgc uguugcgaua ccauaacaag    6120
guauacugua cuacaucaaa gagugccuca cuaagggcua aaaagguaac uuuugauagg    6180
augcaagugc ucgacgccua uuaugauuca gucuuaaagg acaucaagcu agcggccucc    6240
```

-continued

```
aaggucagcg caaggcuccu caccuuagag gaggcgugcc aauugacccc accccacucu   6300
gcaagaucca aguauggguu uggggcuaag gagguccgca gcuuguccgg gagggccguc   6360
aaccacauca aguccgugug gaaggaccuc uuggaagacu cacaaacacc aauuccuaca   6420
accaucaugg ccaaaaauga gguguucugc guggaccccg ccaagggggg uaaaaaacca   6480
gcucgccuua ucguuuaccc ugaccucggc gucagggucu gcgagaagau ggcccuuuau   6540
gaugucacac aaaagcuucc ucaggcggug augggggcuu cuuauggcuu ccaguacucc   6600
cccgcucagc ggguggaguu ucucuugaag gcaugggcgg aaaagagaga cccuaugggu   6660
uuuucguaug auacccgaug cuuugacuca accgucacug agagagacau caggacugag   6720
gaguccauau accaggccug cuccuuaccc gaggaggccc gaacugccau acacucgcug   6780
acugagagac ucuauguggg agggcccaug uucaacagca agggccaguc cugcggguac   6840
aggcguugcc gcgccagcgg ggugcuuacc acuaguaugg ggaacaccau cacaugcuau   6900
guaaaagccc uagcggcuug caaggcugcg gggauaauug cgcccacgau gcugguaugc   6960
ggcgacgacu uggucgucau cucagaaagc caggggacug aggaggacga gcggaaccug   7020
agagccuuca cggaggcuau gaccagguau ucugccccuc cuggugaccc ccccagaccg   7080
gaauaugacc uggagcuaau aacaucuugu ucccucaaacg ugucuguggc acuuggccca   7140
cagggccgcc gcagauacua ccugaccaga gaccccacca cuucaauugc ccgggcugcc   7200
ugggaaacag uuagacacuc cccugucaau ucauggcugg gaaacaucau ccaguacgcu   7260
ccaaccauau ggguucgcau gguccugaug acacacuucu ucuccauucu cauggcccag   7320
gacacccuag accagaaccu uaacuuugaa auguacggau cgguguacuc cgugaguccu   7380
cuggaccucc cagccauaau ugaaagguua cacgggcuug acgccuucuc ucugcacaca   7440
uacacucccc acgaacugac gcggguggcu ucagcccuca gaaaacuugg ggcgccaccc   7500
cucagagcgu ggaagagucg ggcgcgugca guuagggcgu cccucaucuc ccguggggggg   7560 agggcggccg uuugcggucg guaccucuuc aacugggcgg ugaagaccaa gcucaaacuc   7620
acuccuuugc cggaggcacg ccuccuggau uuguccaguu gguuuaccgu cggcgccggc   7680
gggggcgaca uuuaucacag cgugucgcgu gcccgacccc gccuauuacu ccuuagccua   7740
cuccuacuuu cuguaggggu aggccucuuc cuacuccccg cucgauagag cggcacacau   7800
uagcuacacu ccauagcuaa cuguuccuuu uuuuuuuuuu uuuuuuuuuu uuuuuuuuuu   7860
uuuuuuuuuu cuuuuuuuuu uuuuucccuc uuucuucccu ucucaucuua uucuacuuuc   7920
uuucuuggug gcuccaucuu agcccuaguc acggcuagcu gugaaagguc cgugagccgc   7980
augacugcag agagugccgu aacuggucuc ucugcagauc augu                     8024
```

<210> SEQ ID NO 3
<211> LENGTH: 9678
<212> TYPE: DNA
<213> ORGANISM: Hepatitis C virus
<220> FEATURE:
<221> NAME/KEY: CDS
<222> LOCATION: (341)..(9442)

<400> SEQUENCE: 3

```
acctgcccct aataggggcg acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
```

```
cgcttgcgag tgccccggga ggtctcgtag accgtgcacc atg agc aca aat cct      355
                                             Met Ser Thr Asn Pro
                                              1               5 aaa cct caa aga aaa acc aaa aga aac acc aac cgt cgc cca gaa gac      403
Lys Pro Gln Arg Lys Thr Lys Arg Asn Thr Asn Arg Arg Pro Glu Asp
             10                  15                  20 gtt aag ttc ccg ggc ggc cag atc gtt ggc gga gta tac ttg ttg          451
Val Lys Phe Pro Gly Gly Gln Ile Val Gly Gly Val Tyr Leu Leu
         25                  30                  35 ccg cgc agg ggc ccc agg ttg ggt gtg cgc acg aca agg aaa act tcg      499
Pro Arg Arg Gly Pro Arg Leu Gly Val Arg Thr Thr Arg Lys Thr Ser
         40                  45                  50 gag cgg tcc cag cca cgt ggg aga cgc cag ccc atc ccc aaa gat cgg      547
Glu Arg Ser Gln Pro Arg Gly Arg Arg Gln Pro Ile Pro Lys Asp Arg
 55                  60                  65 cgc tcc act ggc aag gcc tgg gga aaa cca ggt cgc ccc tgg ccc cta      595
Arg Ser Thr Gly Lys Ala Trp Gly Lys Pro Gly Arg Pro Trp Pro Leu
 70                  75                  80                  85 tat ggg aat gag gga ctc ggc tgg gca gga tgg ctc ctg tcc ccc cga      643
Tyr Gly Asn Glu Gly Leu Gly Trp Ala Gly Trp Leu Leu Ser Pro Arg
                 90                  95                 100 ggc tct cgc ccc tcc tgg ggc ccc act gac ccc cgg cat agg tcg cgc      691
Gly Ser Arg Pro Ser Trp Gly Pro Thr Asp Pro Arg His Arg Ser Arg
                105                 110                 115 aac gtg ggt aaa gtc atc gac acc cta acg tgt ggc ttt gcc gac ctc      739
Asn Val Gly Lys Val Ile Asp Thr Leu Thr Cys Gly Phe Ala Asp Leu
                120                 125                 130 atg ggg tac atc ccc gtc gta ggc gcc ccg ctt agt ggc gcc gcc aga      787
Met Gly Tyr Ile Pro Val Val Gly Ala Pro Leu Ser Gly Ala Ala Arg
            135                 140                 145 gct gtc gcg cac ggc gtg aga gtc ctg gag gac ggg gtt aat tat gca      835
Ala Val Ala His Gly Val Arg Val Leu Glu Asp Gly Val Asn Tyr Ala
150                 155                 160                 165 aca ggg aac cta ccc ggt ttc ccc ttt tct atc ttc ttg ctg gcc ctg      883
Thr Gly Asn Leu Pro Gly Phe Pro Phe Ser Ile Phe Leu Leu Ala Leu
                170                 175                 180 ttg tcc tgc atc acc gtt ccg gtc tct gct gcc cag gtg aag aat acc      931
Leu Ser Cys Ile Thr Val Pro Val Ser Ala Ala Gln Val Lys Asn Thr
                185                 190                 195 agt agc agc tac atg gtg acc aat gac tgc tcc aat gac agc atc act      979
Ser Ser Ser Tyr Met Val Thr Asn Asp Cys Ser Asn Asp Ser Ile Thr
            200                 205                 210 tgg cag ctc gag gct gcg gtt ctc cac gtc ccc ggg tgc gtc ccg tgc     1027
Trp Gln Leu Glu Ala Ala Val Leu His Val Pro Gly Cys Val Pro Cys
            215                 220                 225 gag aga gtg ggg aat acg tca cgg tgt tgg gtg cca gtc tcg cca aac     1075
Glu Arg Val Gly Asn Thr Ser Arg Cys Trp Val Pro Val Ser Pro Asn
230                 235                 240                 245 atg gct gtg cgg cag ccc ggt gcc ctc acg cag ggt ctg cgg acg cac     1123
Met Ala Val Arg Gln Pro Gly Ala Leu Thr Gln Gly Leu Arg Thr His
                250                 255                 260 atc gat atg gtt gtg atg tcc gcc acc ttc tgc tct gct ctc tac gtg     1171
Ile Asp Met Val Val Met Ser Ala Thr Phe Cys Ser Ala Leu Tyr Val
            265                 270                 275 ggg gac ctc tgt ggc ggg gtg atg ctc gcg gcc cag gtg ttc atc gtc     1219
Gly Asp Leu Cys Gly Gly Val Met Leu Ala Ala Gln Val Phe Ile Val
            280                 285                 290 tcg ccg cag tac cac tgg ttt gtg caa gaa tgc aat tgc tcc atc tac     1267
Ser Pro Gln Tyr His Trp Phe Val Gln Glu Cys Asn Cys Ser Ile Tyr
            295                 300                 305
```

```
cct ggc acc atc act gga cac cgc atg gca tgg gac atg atg atg aac    1315
Pro Gly Thr Ile Thr Gly His Arg Met Ala Trp Asp Met Met Met Asn
310                 315                 320                 325 tgg tcg ccc acg gcc acc atg atc ctg gcg tac gtg atg cgc gtc ccc    1363
Trp Ser Pro Thr Ala Thr Met Ile Leu Ala Tyr Val Met Arg Val Pro
                330                 335                 340 gag gtc atc ata gac atc gtt agc ggg gct cac tgg ggc gtc atg ttc    1411
Glu Val Ile Ile Asp Ile Val Ser Gly Ala His Trp Gly Val Met Phe
            345                 350                 355 ggc ttg gcc tac ttc tct atg cag gga gcg tgg gcg aag gtc att gtc    1459
Gly Leu Ala Tyr Phe Ser Met Gln Gly Ala Trp Ala Lys Val Ile Val
        360                 365                 370 atc ctt ctg ctg gcc gct ggg gtg gac gcg ggc acc acc acc gtt gga    1507
Ile Leu Leu Leu Ala Ala Gly Val Asp Ala Gly Thr Thr Thr Val Gly
    375                 380                 385 ggc gct gtt gca cgt tcc acc aac gtg att gcc ggc gtg ttc agc cat    1555
Gly Ala Val Ala Arg Ser Thr Asn Val Ile Ala Gly Val Phe Ser His
390                 395                 400                 405 ggc cct cag cag aac att cag ctc att aac acc aac ggc agt tgg cac    1603
Gly Pro Gln Gln Asn Ile Gln Leu Ile Asn Thr Asn Gly Ser Trp His
                410                 415                 420 atc aac cgt act gcc ttg aat tgc aat gac tcc ttg aac acc ggc ttt    1651
Ile Asn Arg Thr Ala Leu Asn Cys Asn Asp Ser Leu Asn Thr Gly Phe
            425                 430                 435 ctc gcg gcc ttg ttc tac acc aac cgc ttt aac tcg tca ggg tgt cca    1699
Leu Ala Ala Leu Phe Tyr Thr Asn Arg Phe Asn Ser Ser Gly Cys Pro
        440                 445                 450 ggg cgc ctg tcc gcc tgc cgc aac atc gag gct ttc cgg ata ggg tgg    1747
Gly Arg Leu Ser Ala Cys Arg Asn Ile Glu Ala Phe Arg Ile Gly Trp
    455                 460                 465 ggc acc cta cag tac gag gat aat gtc acc aat cca gag gat atg agg    1795
Gly Thr Leu Gln Tyr Glu Asp Asn Val Thr Asn Pro Glu Asp Met Arg
470                 475                 480                 485 ccg tac tgc tgg cac tac ccc cca aag ccg tgt ggc gta gtc ccc gcg    1843
Pro Tyr Cys Trp His Tyr Pro Pro Lys Pro Cys Gly Val Val Pro Ala
                490                 495                 500 agg tct gtg tgt ggc cca gtg tac tgt ttc acc ccc agc ccg gta gta    1891
Arg Ser Val Cys Gly Pro Val Tyr Cys Phe Thr Pro Ser Pro Val Val
            505                 510                 515 gtg ggc acg acc gac aga cgt gga gtg ccc acc tac aca tgg gga gag    1939
Val Gly Thr Thr Asp Arg Arg Gly Val Pro Thr Tyr Thr Trp Gly Glu
        520                 525                 530 aat gag aca gat gtc ttc cta ctg aac agc acc cga ccg ccg cag ggc    1987
Asn Glu Thr Asp Val Phe Leu Leu Asn Ser Thr Arg Pro Pro Gln Gly
535                 540                 545 tca tgg ttc ggc tgc acg tgg atg aac tcc act ggt ttc acc aag act    2035
Ser Trp Phe Gly Cys Thr Trp Met Asn Ser Thr Gly Phe Thr Lys Thr
550                 555                 560                 565 tgt ggc gcg cca cct tgc cgc acc aga gct gac ttc aac gcc agc acg    2083
Cys Gly Ala Pro Pro Cys Arg Thr Arg Ala Asp Phe Asn Ala Ser Thr
                570                 575                 580 gac ttg ttg tgc cct acg gat tgt ttt agg aag cat cct gat gcc act    2131
Asp Leu Leu Cys Pro Thr Asp Cys Phe Arg Lys His Pro Asp Ala Thr
            585                 590                 595 tat att aag tgt ggt tct ggg ccc tgg ctc aca cca aag tgc ctg gtc    2179
Tyr Ile Lys Cys Gly Ser Gly Pro Trp Leu Thr Pro Lys Cys Leu Val
        600                 605                 610 cac tac cct tac aga ctc tgg cat tac ccc tgc aca gtc aat ttt acc    2227
His Tyr Pro Tyr Arg Leu Trp His Tyr Pro Cys Thr Val Asn Phe Thr
    615                 620                 625
```

-continued

| | | |
|---|---|---|
| atc ttc aag ata aga atg tat gta ggg ggg gtt gag cac agg ctc acg<br>Ile Phe Lys Ile Arg Met Tyr Val Gly Gly Val Glu His Arg Leu Thr<br>630             635                  640             645 | 2275 |
| gcc gca tgc aac ttc act cgt ggg gat cgc tgc gac ttg gag gac agg<br>Ala Ala Cys Asn Phe Thr Arg Gly Asp Arg Cys Asp Leu Glu Asp Arg<br>             650                  655                  660 | 2323 |
| gac agg agt cag ctg tct cct ctg ttg cac tct acc acg gaa tgg gcc<br>Asp Arg Ser Gln Leu Ser Pro Leu Leu His Ser Thr Thr Glu Trp Ala<br>           665                    670                675 | 2371 |
| atc ctg ccc tgc acc tac tca gac tta ccc gct ttg tca act ggt ctt<br>Ile Leu Pro Cys Thr Tyr Ser Asp Leu Pro Ala Leu Ser Thr Gly Leu<br>680             685                  690 | 2419 |
| ctc cac ctt cac cag aac atc gtg gac gta caa tac atg tat ggc ctc<br>Leu His Leu His Gln Asn Ile Val Asp Val Gln Tyr Met Tyr Gly Leu<br>695             700                  705 | 2467 |
| tca cct gct atc aca aaa tac gtc gtt cga tgg gag tgg gtg gta ctc<br>Ser Pro Ala Ile Thr Lys Tyr Val Val Arg Trp Glu Trp Val Val Leu<br>710             715                720             725 | 2515 |
| tta ttc ctg ctc tta gcg gac gcc aga gtc tgc gcc tgc ttg tgg atg<br>Leu Phe Leu Leu Leu Ala Asp Ala Arg Val Cys Ala Cys Leu Trp Met<br>                 730                  735                  740 | 2563 |
| ctc atc ttg ttg ggc cag gcc gaa gca gca ttg gag aag ttg gtc gtc<br>Leu Ile Leu Leu Gly Gln Ala Glu Ala Ala Leu Glu Lys Leu Val Val<br>745             750                  755 | 2611 |
| ttg cac gct gcg agt gcg gct aac tgc cat ggc ctc cta tat ttt gcc<br>Leu His Ala Ala Ser Ala Ala Asn Cys His Gly Leu Leu Tyr Phe Ala<br>             760                  765                  770 | 2659 |
| atc ttc ttc gtg gca gct tgg cac atc agg ggt cgg gtg gtc ccc ttg<br>Ile Phe Phe Val Ala Ala Trp His Ile Arg Gly Arg Val Val Pro Leu<br>775             780                  785 | 2707 |
| acc acc tat tgc ctc act ggc cta tgg ccc ttc tgc cta ctg ctc atg<br>Thr Thr Tyr Cys Leu Thr Gly Leu Trp Pro Phe Cys Leu Leu Leu Met<br>790             795                800             805 | 2755 |
| gca ctg ccc cgg cag gct tat gcc tat gac gca cct gtg cac gga cag<br>Ala Leu Pro Arg Gln Ala Tyr Ala Tyr Asp Ala Pro Val His Gly Gln<br>                 810                  815                  820 | 2803 |
| ata ggc gtg ggt ttg ttg ata ttg atc acc ctc ttc aca ctc acc ccg<br>Ile Gly Val Gly Leu Leu Ile Leu Ile Thr Leu Phe Thr Leu Thr Pro<br>825             830                  835 | 2851 |
| ggg tat aag acc ctc ctc ggc cag tgt ctg tgg tgg ttg tgc tat ctc<br>Gly Tyr Lys Thr Leu Leu Gly Gln Cys Leu Trp Trp Leu Cys Tyr Leu<br>             840                  845                  850 | 2899 |
| ctg acc ctg ggg gaa gcc atg att cag gag tgg gta cca ccc atg cag<br>Leu Thr Leu Gly Glu Ala Met Ile Gln Glu Trp Val Pro Pro Met Gln<br>855             860                  865 | 2947 |
| gtg cgc ggc ggc cgc gat ggc atc gcg tgg gcc gtc act ata ttc tgc<br>Val Arg Gly Gly Arg Asp Gly Ile Ala Trp Ala Val Thr Ile Phe Cys<br>870             875                880             885 | 2995 |
| ccg ggt gtg gtg ttt gac att acc aaa tgg ctt ttg gcg ttg ctt ggg<br>Pro Gly Val Val Phe Asp Ile Thr Lys Trp Leu Leu Ala Leu Leu Gly<br>             890                  895                  900 | 3043 |
| cct gct tac ctc tta agg gcc gct ttg aca cat gtg ccg tac ttc gtc<br>Pro Ala Tyr Leu Leu Arg Ala Ala Leu Thr His Val Pro Tyr Phe Val<br>905             910                  915 | 3091 |
| aga gct cac gct ctg ata agg gta tgc gct ttg gtg aag cag ctc gcg<br>Arg Ala His Ala Leu Ile Arg Val Cys Ala Leu Val Lys Gln Leu Ala<br>             920                  925                  930 | 3139 |
| ggg ggt agg tat gtt cag gtg gcg cta ttg gcc ctt ggc agg tgg act<br>Gly Gly Arg Tyr Val Gln Val Ala Leu Leu Ala Leu Gly Arg Trp Thr<br>935             940                  945 | 3187 |

| | | |
|---|---|---|
| ggc acc tac atc tat gac cac ctc aca cct atg tcg gac tgg gcc gct<br>Gly Thr Tyr Ile Tyr Asp His Leu Thr Pro Met Ser Asp Trp Ala Ala<br>950                   955                   960               965 | | 3235 |
| agc ggc ctg cgc gac tta gcg gtc gcc gtg gaa ccc atc atc ttc agt<br>Ser Gly Leu Arg Asp Leu Ala Val Ala Val Glu Pro Ile Ile Phe Ser<br>                   970                   975                   980 | | 3283 |
| ccg atg gag aag aag gtc atc gtc tgg gga gcg gag acg gct gca tgt<br>Pro Met Glu Lys Lys Val Ile Val Trp Gly Ala Glu Thr Ala Ala Cys<br>               985                   990                   995 | | 3331 |
| ggg gac att cta cat gga ctt ccc gtg tcc gcc cga ctc ggc cag gag<br>Gly Asp Ile Leu His Gly Leu Pro Val Ser Ala Arg Leu Gly Gln Glu<br>1000                 1005                1010 | | 3379 |
| atc ctc ctc ggc cca gct gat ggc tac acc tcc aag ggg tgg aag ctc<br>Ile Leu Leu Gly Pro Ala Asp Gly Tyr Thr Ser Lys Gly Trp Lys Leu<br>   1015                1020                1025 | | 3427 |
| ctt gct ccc atc act gct tat gcc cag caa aca cga ggc ctc ctg ggc<br>Leu Ala Pro Ile Thr Ala Tyr Ala Gln Gln Thr Arg Gly Leu Leu Gly<br>1030                 1035                1040                1045 | | 3475 |
| gcc ata gtg gtg agt atg acg ggg cgt gac agg aca gaa cag gcc ggg<br>Ala Ile Val Val Ser Met Thr Gly Arg Asp Arg Thr Glu Gln Ala Gly<br>                  1050                1055                1060 | | 3523 |
| gaa gtc caa atc ctg tcc aca gtc tct cag tcc ttc ctc gga aca acc<br>Glu Val Gln Ile Leu Ser Thr Val Ser Gln Ser Phe Leu Gly Thr Thr<br>              1065                1070                1075 | | 3571 |
| atc tcg ggg gtt ttg tgg act gtt tac cac gga gct ggc aac aag act<br>Ile Ser Gly Val Leu Trp Thr Val Tyr His Gly Ala Gly Asn Lys Thr<br>1080                 1085                1090 | | 3619 |
| cta gcc ggc tta cgg ggt ccg gtc acg cag atg tac tcg agt gct gag<br>Leu Ala Gly Leu Arg Gly Pro Val Thr Gln Met Tyr Ser Ser Ala Glu<br>   1095                1100                1105 | | 3667 |
| ggg gac ttg gta ggc tgg ccc agc ccc cct ggg acc aag tct ttg gag<br>Gly Asp Leu Val Gly Trp Pro Ser Pro Pro Gly Thr Lys Ser Leu Glu<br>1110                 1115                1120                1125 | | 3715 |
| ccg tgc aag tgt gga gcc gtc gac cta tat ctg gtc acg cgg aac gct<br>Pro Cys Lys Cys Gly Ala Val Asp Leu Tyr Leu Val Thr Arg Asn Ala<br>                  1130                1135                1140 | | 3763 |
| gat gtc atc ccg gct cgg aga cgc ggg gac aag cgg gga gca ttg ctc<br>Asp Val Ile Pro Ala Arg Arg Arg Gly Asp Lys Arg Gly Ala Leu Leu<br>              1145                1150                1155 | | 3811 |
| tcc ccg aga ccc att tcg acc ttg aag ggg tcc tcg ggg ggg ccg gtg<br>Ser Pro Arg Pro Ile Ser Thr Leu Lys Gly Ser Ser Gly Gly Pro Val<br>1160                 1165                1170 | | 3859 |
| ctc tgc cct agg ggc cac gtc gtt ggg ctc ttc cga gca gct gtg tgc<br>Leu Cys Pro Arg Gly His Val Val Gly Leu Phe Arg Ala Ala Val Cys<br>   1175                1180                1185 | | 3907 |
| tct cgg ggc gtg gcc aaa tcc atc gat ttc atc ccc gtt gag aca ctc<br>Ser Arg Gly Val Ala Lys Ser Ile Asp Phe Ile Pro Val Glu Thr Leu<br>1190                 1195                1200                1205 | | 3955 |
| gac gtt gtt aca agg tct ccc act ttc agt gac aac agc acg cca ccg<br>Asp Val Val Thr Arg Ser Pro Thr Phe Ser Asp Asn Ser Thr Pro Pro<br>                  1210                1215                1220 | | 4003 |
| gct gtg ccc cag acc tat cag gtc ggg tac ttg cat gct cca act ggc<br>Ala Val Pro Gln Thr Tyr Gln Val Gly Tyr Leu His Ala Pro Thr Gly<br>              1225                1230                1235 | | 4051 |
| agt gga aag agc acc aag gtc cct gtc gcg tat gcc gcc cag ggg tac<br>Ser Gly Lys Ser Thr Lys Val Pro Val Ala Tyr Ala Ala Gln Gly Tyr<br>1240                 1245                1250 | | 4099 |
| aaa gta cta gtg ctt aac ccc tcg gta gct gcc acc ctg ggg ttt ggg<br>Lys Val Leu Val Leu Asn Pro Ser Val Ala Ala Thr Leu Gly Phe Gly<br>   1255                1260                1265 | | 4147 |

```
gcg tac cta tcc aag gca cat ggc atc aat ccc aac att agg act gga    4195
Ala Tyr Leu Ser Lys Ala His Gly Ile Asn Pro Asn Ile Arg Thr Gly
    1270            1275                1280                1285 gtc agg acc gtg atg acc ggg gag gcc atc acg tac tcc aca tat ggc    4243
Val Arg Thr Val Met Thr Gly Glu Ala Ile Thr Tyr Ser Thr Tyr Gly
            1290                1295                1300 aaa ttt ctc gcc gat ggg ggc tgc gct agc ggc gcc tat gac atc atc    4291
Lys Phe Leu Ala Asp Gly Gly Cys Ala Ser Gly Ala Tyr Asp Ile Ile
        1305                1310                1315 ata tgc gat gaa tgc cac gct gtg gat gct acc tcc att ctc ggc atc    4339
Ile Cys Asp Glu Cys His Ala Val Asp Ala Thr Ser Ile Leu Gly Ile
    1320                1325                1330 gga acg gtc ctt gat caa gca gag aca gcc ggg gtc aga cta act gtg    4387
Gly Thr Val Leu Asp Gln Ala Glu Thr Ala Gly Val Arg Leu Thr Val
1335                1340                1345 ctg gct acg gcc aca ccc ccc ggg tca gtg aca acc ccc cat ccc gat    4435
Leu Ala Thr Ala Thr Pro Pro Gly Ser Val Thr Thr Pro His Pro Asp
1350                1355                1360                1365 ata gaa gag gta ggc ctc ggg cgg gag ggt gag atc ccc ttc tat ggg    4483
Ile Glu Glu Val Gly Leu Gly Arg Glu Gly Glu Ile Pro Phe Tyr Gly
            1370                1375                1380 agg gcg att ccc cta tcc tgc atc aag gga ggg aga cac ctg att ttc    4531
Arg Ala Ile Pro Leu Ser Cys Ile Lys Gly Gly Arg His Leu Ile Phe
        1385                1390                1395 tgc cac tca aag aaa aag tgt gac gag ctc gcg gcg gcc ctt cgg ggc    4579
Cys His Ser Lys Lys Lys Cys Asp Glu Leu Ala Ala Ala Leu Arg Gly
    1400                1405                1410 atg ggc ttg aat gcc gtg gca tac tat aga ggg ttg gac gtc tcc ata    4627
Met Gly Leu Asn Ala Val Ala Tyr Tyr Arg Gly Leu Asp Val Ser Ile
1415                1420                1425 ata cca gct cag gga gat gtg gtg gtc gtc gcc acc gac gcc ctc atg    4675
Ile Pro Ala Gln Gly Asp Val Val Val Val Ala Thr Asp Ala Leu Met
1430                1435                1440                1445 acg ggg tac act gga gac ttt gac tcc gtg atc gac tgc aat gta gcg    4723
Thr Gly Tyr Thr Gly Asp Phe Asp Ser Val Ile Asp Cys Asn Val Ala
            1450                1455                1460 gtc acc caa gct gtc gac ttc agc ctg gac ccc acc ttc act ata acc    4771
Val Thr Gln Ala Val Asp Phe Ser Leu Asp Pro Thr Phe Thr Ile Thr
        1465                1470                1475 aca cag act gtc cca caa gac gct gtc tca cgc agt cag cgc cgc ggg    4819
Thr Gln Thr Val Pro Gln Asp Ala Val Ser Arg Ser Gln Arg Arg Gly
    1480                1485                1490 cgc aca ggt aga gga aga cag ggc act tat agg tat gtt tcc act ggt    4867
Arg Thr Gly Arg Gly Arg Gln Gly Thr Tyr Arg Tyr Val Ser Thr Gly
1495                1500                1505 gaa cga gcc tca gga atg ttt gac agt gta gtg ctt tgt gag tgc tac    4915
Glu Arg Ala Ser Gly Met Phe Asp Ser Val Val Leu Cys Glu Cys Tyr
1510                1515                1520                1525 gac gca ggg gct gcg tgg tac gat ctc aca cca gcg gag acc acc gtc    4963
Asp Ala Gly Ala Ala Trp Tyr Asp Leu Thr Pro Ala Glu Thr Thr Val
            1530                1535                1540 agg ctt aga gcg tat ttc aac acg ccc ggc cta ccc gtg tgt caa gac    5011
Arg Leu Arg Ala Tyr Phe Asn Thr Pro Gly Leu Pro Val Cys Gln Asp
        1545                1550                1555 cat ctt gaa ttt tgg gag gca gtt ttc acc ggc ctc aca cac ata gac    5059
His Leu Glu Phe Trp Glu Ala Val Phe Thr Gly Leu Thr His Ile Asp
    1560                1565                1570 gcc cac ttc ctc tcc caa aca aag caa gcg ggg gag aac ttc gcg tac    5107
Ala His Phe Leu Ser Gln Thr Lys Gln Ala Gly Glu Asn Phe Ala Tyr
1575                1580                1585
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cta | gta | gcc | tac | caa | gct | acg | gtg | tgc | gcc | aga | gcc | aag | gcc | cct | ccc | 5155 |
| Leu | Val | Ala | Tyr | Gln | Ala | Thr | Val | Cys | Ala | Arg | Ala | Lys | Ala | Pro | Pro |  |
|  | 1590 |  |  |  | 1595 |  |  |  | 1600 |  |  |  | 1605 |  |  |  |

| ccg | tcc | tgg | gac | gcc | atg | tgg | aag | tgc | ctg | gcc | cga | ctc | aag | cct | acg | 5203 |
| --- | --- | --- | --- | --- | --- | --- | --- | --- | --- | --- | --- | --- | --- | --- | --- | --- |
| Pro | Ser | Trp | Asp | Ala | Met | Trp | Lys | Cys | Leu | Ala | Arg | Leu | Lys | Pro | Thr |  |
|  |  | 1610 |  |  |  | 1615 |  |  |  | 1620 |  |  |  |  |  |  |

| ctt | gcg | ggc | ccc | aca | cct | ctc | ctg | tac | cgt | ttg | ggc | cct | att | acc | aat | 5251 |
| --- | --- | --- | --- | --- | --- | --- | --- | --- | --- | --- | --- | --- | --- | --- | --- | --- |
| Leu | Ala | Gly | Pro | Thr | Pro | Leu | Leu | Tyr | Arg | Leu | Gly | Pro | Ile | Thr | Asn |  |
|  | 1625 |  |  |  | 1630 |  |  |  | 1635 |  |  |  |  |  |  |  |

| gag | gtc | acc | ctc | aca | cac | cct | ggg | acg | aag | tac | atc | gcc | aca | tgc | atg | 5299 |
| --- | --- | --- | --- | --- | --- | --- | --- | --- | --- | --- | --- | --- | --- | --- | --- | --- |
| Glu | Val | Thr | Leu | Thr | His | Pro | Gly | Thr | Lys | Tyr | Ile | Ala | Thr | Cys | Met |  |
| 1640 |  |  |  | 1645 |  |  |  | 1650 |  |  |  |  |  |  |  |  |

| caa | gct | gac | ctt | gag | gtc | atg | acc | agc | acg | tgg | gtc | cta | gct | gga | gga | 5347 |
| --- | --- | --- | --- | --- | --- | --- | --- | --- | --- | --- | --- | --- | --- | --- | --- | --- |
| Gln | Ala | Asp | Leu | Glu | Val | Met | Thr | Ser | Thr | Trp | Val | Leu | Ala | Gly | Gly |  |
|  | 1655 |  |  |  | 1660 |  |  |  | 1665 |  |  |  |  |  |  |  |

| gtc | ctg | gca | gcc | gtc | gcc | gca | tat | tgc | ctg | gcg | act | gga | tgc | gtt | tcc | 5395 |
| --- | --- | --- | --- | --- | --- | --- | --- | --- | --- | --- | --- | --- | --- | --- | --- | --- |
| Val | Leu | Ala | Ala | Val | Ala | Ala | Tyr | Cys | Leu | Ala | Thr | Gly | Cys | Val | Ser |  |
| 1670 |  |  |  | 1675 |  |  |  | 1680 |  |  |  | 1685 |  |  |  |  |

| atc | atc | ggc | cgc | ttg | cac | gtc | aac | cag | cga | gtc | gtc | gtt | gcg | ccg | gat | 5443 |
| --- | --- | --- | --- | --- | --- | --- | --- | --- | --- | --- | --- | --- | --- | --- | --- | --- |
| Ile | Ile | Gly | Arg | Leu | His | Val | Asn | Gln | Arg | Val | Val | Val | Ala | Pro | Asp |  |
|  |  | 1690 |  |  |  | 1695 |  |  |  | 1700 |  |  |  |  |  |  |

| aag | gag | gtc | ctg | tat | gag | gct | ttt | gat | gag | atg | gag | gaa | tgc | gcc | tct | 5491 |
| --- | --- | --- | --- | --- | --- | --- | --- | --- | --- | --- | --- | --- | --- | --- | --- | --- |
| Lys | Glu | Val | Leu | Tyr | Glu | Ala | Phe | Asp | Glu | Met | Glu | Glu | Cys | Ala | Ser |  |
|  | 1705 |  |  |  | 1710 |  |  |  | 1715 |  |  |  |  |  |  |  |

| agg | gcg | gct | ctc | atc | gaa | gag | ggg | cag | cgg | ata | gcc | gag | atg | ttg | aag | 5539 |
| --- | --- | --- | --- | --- | --- | --- | --- | --- | --- | --- | --- | --- | --- | --- | --- | --- |
| Arg | Ala | Ala | Leu | Ile | Glu | Glu | Gly | Gln | Arg | Ile | Ala | Glu | Met | Leu | Lys |  |
|  | 1720 |  |  |  | 1725 |  |  |  | 1730 |  |  |  |  |  |  |  |

| tcc | aag | atc | caa | ggc | ttg | ctg | cag | cag | gcc | tct | aag | cag | gcc | cag | gac | 5587 |
| --- | --- | --- | --- | --- | --- | --- | --- | --- | --- | --- | --- | --- | --- | --- | --- | --- |
| Ser | Lys | Ile | Gln | Gly | Leu | Leu | Gln | Gln | Ala | Ser | Lys | Gln | Ala | Gln | Asp |  |
| 1735 |  |  |  | 1740 |  |  |  | 1745 |  |  |  |  |  |  |  |  |

| ata | caa | ccc | gct | atg | cag | gct | tca | tgg | ccc | aaa | gtg | gaa | caa | ttt | tgg | 5635 |
| --- | --- | --- | --- | --- | --- | --- | --- | --- | --- | --- | --- | --- | --- | --- | --- | --- |
| Ile | Gln | Pro | Ala | Met | Gln | Ala | Ser | Trp | Pro | Lys | Val | Glu | Gln | Phe | Trp |  |
| 1750 |  |  |  | 1755 |  |  |  | 1760 |  |  |  | 1765 |  |  |  |  |

| gcc | aga | cac | atg | tgg | aac | ttc | att | agc | ggc | atc | caa | tac | ctc | gca | gga | 5683 |
| --- | --- | --- | --- | --- | --- | --- | --- | --- | --- | --- | --- | --- | --- | --- | --- | --- |
| Ala | Arg | His | Met | Trp | Asn | Phe | Ile | Ser | Gly | Ile | Gln | Tyr | Leu | Ala | Gly |  |
|  | 1770 |  |  |  | 1775 |  |  |  | 1780 |  |  |  |  |  |  |  |

| ttg | tca | aca | ctg | cca | ggg | aac | ccc | gcg | gtg | gct | tcc | atg | atg | gca | ttc | 5731 |
| --- | --- | --- | --- | --- | --- | --- | --- | --- | --- | --- | --- | --- | --- | --- | --- | --- |
| Leu | Ser | Thr | Leu | Pro | Gly | Asn | Pro | Ala | Val | Ala | Ser | Met | Met | Ala | Phe |  |
|  | 1785 |  |  |  | 1790 |  |  |  | 1795 |  |  |  |  |  |  |  |

| agt | gcc | gcc | ctc | acc | agt | ccg | ttg | tcg | acc | agt | acc | acc | atc | ctt | ctc | 5779 |
| --- | --- | --- | --- | --- | --- | --- | --- | --- | --- | --- | --- | --- | --- | --- | --- | --- |
| Ser | Ala | Ala | Leu | Thr | Ser | Pro | Leu | Ser | Thr | Ser | Thr | Thr | Ile | Leu | Leu |  |
|  | 1800 |  |  |  | 1805 |  |  |  | 1810 |  |  |  |  |  |  |  |

| aac | atc | atg | gga | ggc | tgg | tta | gcg | tcc | cag | atc | gca | cca | ccc | gcg | ggg | 5827 |
| --- | --- | --- | --- | --- | --- | --- | --- | --- | --- | --- | --- | --- | --- | --- | --- | --- |
| Asn | Ile | Met | Gly | Gly | Trp | Leu | Ala | Ser | Gln | Ile | Ala | Pro | Pro | Ala | Gly |  |
| 1815 |  |  |  | 1820 |  |  |  | 1825 |  |  |  |  |  |  |  |  |

| gcc | acc | ggc | ttt | gtc | gtc | agt | ggc | ctg | gtg | ggg | gct | gcc | gtg | ggc | agc | 5875 |
| --- | --- | --- | --- | --- | --- | --- | --- | --- | --- | --- | --- | --- | --- | --- | --- | --- |
| Ala | Thr | Gly | Phe | Val | Val | Ser | Gly | Leu | Val | Gly | Ala | Ala | Val | Gly | Ser |  |
| 1830 |  |  |  | 1835 |  |  |  | 1840 |  |  |  | 1845 |  |  |  |  |

| ata | ggc | ctg | ggt | aag | gtg | ctg | gtg | gac | atc | ctg | gca | gga | tat | ggt | gcg | 5923 |
| --- | --- | --- | --- | --- | --- | --- | --- | --- | --- | --- | --- | --- | --- | --- | --- | --- |
| Ile | Gly | Leu | Gly | Lys | Val | Leu | Val | Asp | Ile | Leu | Ala | Gly | Tyr | Gly | Ala |  |
|  | 1850 |  |  |  | 1855 |  |  |  | 1860 |  |  |  |  |  |  |  |

| ggc | att | tcg | ggg | gcc | ctc | gtc | gca | ttc | aag | atc | atg | tct | ggc | gag | aag | 5971 |
| --- | --- | --- | --- | --- | --- | --- | --- | --- | --- | --- | --- | --- | --- | --- | --- | --- |
| Gly | Ile | Ser | Gly | Ala | Leu | Val | Ala | Phe | Lys | Ile | Met | Ser | Gly | Glu | Lys |  |
|  | 1865 |  |  |  | 1870 |  |  |  | 1875 |  |  |  |  |  |  |  |

| ccc | tct | atg | gaa | gat | gtc | atc | aat | cta | ctg | cct | ggg | atc | ctg | tct | ccg | 6019 |
| --- | --- | --- | --- | --- | --- | --- | --- | --- | --- | --- | --- | --- | --- | --- | --- | --- |
| Pro | Ser | Met | Glu | Asp | Val | Ile | Asn | Leu | Leu | Pro | Gly | Ile | Leu | Ser | Pro |  |
| 1880 |  |  |  | 1885 |  |  |  | 1890 |  |  |  |  |  |  |  |  |

| gga | gcc | ctg | gtg | gtg | ggg | gtc | atc | tgc | gcg | gcc | att | ctg | cgc | cgc | cac | 6067 |
| --- | --- | --- | --- | --- | --- | --- | --- | --- | --- | --- | --- | --- | --- | --- | --- | --- |
| Gly | Ala | Leu | Val | Val | Gly | Val | Ile | Cys | Ala | Ala | Ile | Leu | Arg | Arg | His |  |
| 1895 |  |  |  | 1900 |  |  |  | 1905 |  |  |  |  |  |  |  |  |

```
gtg gga ccg ggg gag ggc gcg gtc caa tgg atg aac agg ctt att gcc    6115
Val Gly Pro Gly Glu Gly Ala Val Gln Trp Met Asn Arg Leu Ile Ala
1910                1915                1920                1925 ttt gct tcc aga gga aac cac gtc gcc cct act cac tac gtg acg gag    6163
Phe Ala Ser Arg Gly Asn His Val Ala Pro Thr His Tyr Val Thr Glu
            1930                1935                1940 tcg gat gcg tcg cag cgt gtg acc caa cta ctt ggc tct ctt act ata    6211
Ser Asp Ala Ser Gln Arg Val Thr Gln Leu Leu Gly Ser Leu Thr Ile
        1945                1950                1955 acc agc cta ctc aga aga ctc cac aat tgg ata act gag gac tgc ccc    6259
Thr Ser Leu Leu Arg Arg Leu His Asn Trp Ile Thr Glu Asp Cys Pro
    1960                1965                1970 atc cca tgc tcc gga tcc tgg ctc cgc gac gtg tgg gac tgg gtt tgc    6307
Ile Pro Cys Ser Gly Ser Trp Leu Arg Asp Val Trp Asp Trp Val Cys
1975                1980                1985 acc atc ttg aca gac ttc aaa aat tgg ctg acc tct aaa ttg ttc ccc    6355
Thr Ile Leu Thr Asp Phe Lys Asn Trp Leu Thr Ser Lys Leu Phe Pro
1990                1995                2000                2005 aag ctg ccc ggc ctc ccc ttc atc tct tgt caa aag ggg tac aag ggt    6403
Lys Leu Pro Gly Leu Pro Phe Ile Ser Cys Gln Lys Gly Tyr Lys Gly
            2010                2015                2020 gtg tgg gcc ggc act ggc atc atg acc acg cgc tgc cct tgc ggc gcc    6451
Val Trp Ala Gly Thr Gly Ile Met Thr Thr Arg Cys Pro Cys Gly Ala
        2025                2030                2035 aac atc tct ggc aat gtc cgc ctg ggc tct atg agg atc aca ggg cct    6499
Asn Ile Ser Gly Asn Val Arg Leu Gly Ser Met Arg Ile Thr Gly Pro
    2040                2045                2050 aaa acc tgc atg aac acc tgg cag ggg acc ttt cct atc aat tgc tac    6547
Lys Thr Cys Met Asn Thr Trp Gln Gly Thr Phe Pro Ile Asn Cys Tyr
2055                2060                2065 acg gag ggc cag tgc gcg ccg aaa ccc ccc acg aac tac aag acc gcc    6595
Thr Glu Gly Gln Cys Ala Pro Lys Pro Pro Thr Asn Tyr Lys Thr Ala
2070                2075                2080                2085 atc tgg agg gtg gcg gcc tcg gag tac gcg gag gtg acg cag cat ggg    6643
Ile Trp Arg Val Ala Ala Ser Glu Tyr Ala Glu Val Thr Gln His Gly
            2090                2095                2100 tcg tac tcc tat gta aca gga ctg acc act gac aat ctg aaa att cct    6691
Ser Tyr Ser Tyr Val Thr Gly Leu Thr Thr Asp Asn Leu Lys Ile Pro
        2105                2110                2115 tgc caa cta cct tct cca gag ttt ttc tcc tgg gtg gac ggt gtg cag    6739
Cys Gln Leu Pro Ser Pro Glu Phe Phe Ser Trp Val Asp Gly Val Gln
    2120                2125                2130 atc cat agg ttt gca ccc aca cca aag ccg ttt ttc cgg gat gag gtc    6787
Ile His Arg Phe Ala Pro Thr Pro Lys Pro Phe Phe Arg Asp Glu Val
2135                2140                2145 tcg ttc tgc gtt ggg ctt aat tcc tat gct gtc ggg tcc cag ctt ccc    6835
Ser Phe Cys Val Gly Leu Asn Ser Tyr Ala Val Gly Ser Gln Leu Pro
2150                2155                2160                2165 tgt gaa cct gag ccc gac gca gac gta ttg agg tcc atg cta aca gat    6883
Cys Glu Pro Glu Pro Asp Ala Asp Val Leu Arg Ser Met Leu Thr Asp
            2170                2175                2180 ccg ccc cac atc acg gcg gag act gcg gcg cgg cgc ttg gca cgg gga    6931
Pro Pro His Ile Thr Ala Glu Thr Ala Ala Arg Arg Leu Ala Arg Gly
        2185                2190                2195 tca cct cca tct gag gcg agc tcc tca gtg agc cag cta tca gca ccg    6979
Ser Pro Pro Ser Glu Ala Ser Ser Ser Val Ser Gln Leu Ser Ala Pro
    2200                2205                2210 tcg ctg cgg gcc acc tgc acc acc cac agc aac acc tat gac gtg gac    7027
Ser Leu Arg Ala Thr Cys Thr Thr His Ser Asn Thr Tyr Asp Val Asp
2215                2220                2225
```

```
atg gtc gat gcc aac ctg ctc atg gag ggc ggt gtg gct cag aca gag     7075
Met Val Asp Ala Asn Leu Leu Met Glu Gly Gly Val Ala Gln Thr Glu
2230                2235                2240                2245 cct gag tcc agg gtg ccc gtt ctg gac ttt ctc gag cca atg gcc gag     7123
Pro Glu Ser Arg Val Pro Val Leu Asp Phe Leu Glu Pro Met Ala Glu
            2250                2255                2260 gaa gag agc gac ctt gag ccc tca ata cca tcg gag tgc atg ctc ccc     7171
Glu Glu Ser Asp Leu Glu Pro Ser Ile Pro Ser Glu Cys Met Leu Pro
        2265                2270                2275 agg agc ggg ttt cca cgg gcc tta ccg gct tgg gca cgg cct gac tac     7219
Arg Ser Gly Phe Pro Arg Ala Leu Pro Ala Trp Ala Arg Pro Asp Tyr
    2280                2285                2290 aac ccg ccg ctc gtg gaa tcg tgg agg agg cca gat tac caa ccg ccc     7267
Asn Pro Pro Leu Val Glu Ser Trp Arg Arg Pro Asp Tyr Gln Pro Pro
2295                2300                2305 acc gtt gct ggt tgt gct ctc ccc ccc ccc aag aag gcc ccg acg cct     7315
Thr Val Ala Gly Cys Ala Leu Pro Pro Pro Lys Lys Ala Pro Thr Pro
2310                2315                2320                2325 ccc cca agg aga cgc cgg aca gtg ggt ctg agc gag agc acc ata tca     7363
Pro Pro Arg Arg Arg Arg Thr Val Gly Leu Ser Glu Ser Thr Ile Ser
            2330                2335                2340 gaa gcc ctc cag caa ctg gcc atc aag acc ttt ggc cag ccc ccc tcg     7411
Glu Ala Leu Gln Gln Leu Ala Ile Lys Thr Phe Gly Gln Pro Pro Ser
        2345                2350                2355 agc ggt gat gca ggc tcg tcc acg ggg gcg ggc gcc gcc gaa tcc ggc     7459
Ser Gly Asp Ala Gly Ser Ser Thr Gly Ala Gly Ala Ala Glu Ser Gly
    2360                2365                2370 ggt ccg acg tcc cct ggt gag ccg gcc ccc tca gag aca ggt tcc gcc     7507
Gly Pro Thr Ser Pro Gly Glu Pro Ala Pro Ser Glu Thr Gly Ser Ala
2375                2380                2385 tcc tct atg ccc ccc ctc gag ggg gag cct gga gat ccg gac ctg gag     7555
Ser Ser Met Pro Pro Leu Glu Gly Glu Pro Gly Asp Pro Asp Leu Glu
2390                2395                2400                2405 tct gat cag gta gag ctt caa cct ccc ccc cag ggg ggg ggg gta gct     7603
Ser Asp Gln Val Glu Leu Gln Pro Pro Pro Gln Gly Gly Gly Val Ala
            2410                2415                2420 ccc ggt tcg ggc tcg ggg tct tgg tct act tgc tcc gag gag gac gat     7651
Pro Gly Ser Gly Ser Gly Ser Trp Ser Thr Cys Ser Glu Glu Asp Asp
        2425                2430                2435 acc acc gtg tgc tgc tcc atg tca tac tcc tgg acc ggg gct cta ata     7699
Thr Thr Val Cys Cys Ser Met Ser Tyr Ser Trp Thr Gly Ala Leu Ile
    2440                2445                2450 act ccc tgt agc ccc gaa gag gaa aag ttg cca atc aac cct ttg agt     7747
Thr Pro Cys Ser Pro Glu Glu Glu Lys Leu Pro Ile Asn Pro Leu Ser
2455                2460                2465 aac tcg ctg ttg cga tac cat aac aag gtg tac tgt aca aca tca aag     7795
Asn Ser Leu Leu Arg Tyr His Asn Lys Val Tyr Cys Thr Thr Ser Lys
2470                2475                2480                2485 agc gcc tca cag agg gct aaa aag gta act ttt gac agg acg caa gtg     7843
Ser Ala Ser Gln Arg Ala Lys Lys Val Thr Phe Asp Arg Thr Gln Val
            2490                2495                2500 ctc gac gcc cat tat gac tca gtc tta aag gac atc aag cta gcg gct     7891
Leu Asp Ala His Tyr Asp Ser Val Leu Lys Asp Ile Lys Leu Ala Ala
        2505                2510                2515 tcc aag gtc agc gca agg ctc ctc acc ttg gag gag gcg tgc cag ttg     7939
Ser Lys Val Ser Ala Arg Leu Leu Thr Leu Glu Glu Ala Cys Gln Leu
    2520                2525                2530 act cca ccc cat tct gca aga tcc aag tat gga ttc ggg gcc aag gag     7987
Thr Pro Pro His Ser Ala Arg Ser Lys Tyr Gly Phe Gly Ala Lys Glu
2535                2540                2545
```

```
                                                        -continued gtc cgc agc ttg tcc ggg agg gcc gtt aac cac atc aag tcc gtg tgg      8035
Val Arg Ser Leu Ser Gly Arg Ala Val Asn His Ile Lys Ser Val Trp
2550                2555                2560                2565 aag gac ctc ctg gaa gac cca caa aca cca att ccc aca acc atc atg      8083
Lys Asp Leu Leu Glu Asp Pro Gln Thr Pro Ile Pro Thr Thr Ile Met
        2570                2575                2580 gcc aaa aat gag gtg ttc tgc gtg gac ccc gcc aag ggg ggt aag aaa      8131
Ala Lys Asn Glu Val Phe Cys Val Asp Pro Ala Lys Gly Gly Lys Lys
            2585                2590                2595 cca gct cgc ctc atc gtt tac cct gac ctc ggc gtc cgg gtc tgc gag      8179
Pro Ala Arg Leu Ile Val Tyr Pro Asp Leu Gly Val Arg Val Cys Glu
2600                2605                2610 aaa atg gcc ctc tat gac att aca caa aag ctt cct cag gcg gta atg      8227
Lys Met Ala Leu Tyr Asp Ile Thr Gln Lys Leu Pro Gln Ala Val Met
        2615                2620                2625 gga gct tcc tat ggc ttc cag tac tcc cct gcc caa cgg gtg gag tat      8275
Gly Ala Ser Tyr Gly Phe Gln Tyr Ser Pro Ala Gln Arg Val Glu Tyr
            2630                2635                2640                2645 ctc ttg aaa gca tgg gcg gaa aag aag gac ccc atg ggt ttt tcg tat      8323
Leu Leu Lys Ala Trp Ala Glu Lys Lys Asp Pro Met Gly Phe Ser Tyr
2650                2655                2660 gat acc cga tgc ttc gac tca acc gtc act gag aga gac atc agg acc      8371
Asp Thr Arg Cys Phe Asp Ser Thr Val Thr Glu Arg Asp Ile Arg Thr
        2665                2670                2675 gag gag tcc ata tac cag gcc tgc tcc ctg ccc gag gag gcc cgc act      8419
Glu Glu Ser Ile Tyr Gln Ala Cys Ser Leu Pro Glu Glu Ala Arg Thr
            2680                2685                2690 gcc ata cac tcg ctg act gag aga ctt tac gta gga ggg ccc atg ttc      8467
Ala Ile His Ser Leu Thr Glu Arg Leu Tyr Val Gly Gly Pro Met Phe
2695                2700                2705 aac agc aag ggt caa acc tgc ggt tac aga cgt tgc cgc gcc agc ggg      8515
Asn Ser Lys Gly Gln Thr Cys Gly Tyr Arg Arg Cys Arg Ala Ser Gly
        2710                2715                2720                2725 gtg cta acc act agc atg ggt aac acc atc aca tgc tat gtg aaa gcc      8563
Val Leu Thr Thr Ser Met Gly Asn Thr Ile Thr Cys Tyr Val Lys Ala
            2730                2735                2740 cta gcg gcc tgc aag gct gcg ggg ata gtt gcg ccc aca atg ctg gta      8611
Leu Ala Ala Cys Lys Ala Ala Gly Ile Val Ala Pro Thr Met Leu Val
2745                2750                2755 tgc ggc gat gac cta gta gtc atc tca gaa agc cag ggg act gag gag      8659
Cys Gly Asp Asp Leu Val Val Ile Ser Glu Ser Gln Gly Thr Glu Glu
        2760                2765                2770 gac gag cgg aac ctg aga gcc ttc acg gag gcc atg acc agg tac tct      8707
Asp Glu Arg Asn Leu Arg Ala Phe Thr Glu Ala Met Thr Arg Tyr Ser
            2775                2780                2785 gcc cct cct ggt gat ccc ccc aga ccg gaa tat gac ctg gag cta ata      8755
Ala Pro Pro Gly Asp Pro Pro Arg Pro Glu Tyr Asp Leu Glu Leu Ile
2790                2795                2800                2805 aca tcc tgt tcc tca aat gtg tct gtg gcg ttg ggc ccg cgg ggc cgc      8803
Thr Ser Cys Ser Ser Asn Val Ser Val Ala Leu Gly Pro Arg Gly Arg
        2810                2815                2820 cgc aga tac tac ctg acc aga gac cca acc act cca ctc gcc cgg gct      8851
Arg Arg Tyr Tyr Leu Thr Arg Asp Pro Thr Thr Pro Leu Ala Arg Ala
            2825                2830                2835 gcc tgg gaa aca gtt aga cac tcc cct atc aat tca tgg ctg gga aac      8899
Ala Trp Glu Thr Val Arg His Ser Pro Ile Asn Ser Trp Leu Gly Asn
2840                2845                2850 atc atc cag tat gct cca acc ata tgg gtt cgc atg gtc cta atg aca      8947
Ile Ile Gln Tyr Ala Pro Thr Ile Trp Val Arg Met Val Leu Met Thr
        2855                2860                2865
```

| | | | | | | | | | | | | | | | |
|---|---|---|---|---|---|---|---|---|---|---|---|---|---|---|---|
| cac | ttc | ttc | tcc | att | ctc | atg | gtc | caa | gac | acc | ctg | gac | cag | aac | ctc | 8995
| His | Phe | Phe | Ser | Ile | Leu | Met | Val | Gln | Asp | Thr | Leu | Asp | Gln | Asn | Leu |
| 2870 | | | | | 2875 | | | | | 2880 | | | | | 2885 |

```
cac ttc ttc tcc att ctc atg gtc caa gac acc ctg gac cag aac ctc     8995
His Phe Phe Ser Ile Leu Met Val Gln Asp Thr Leu Asp Gln Asn Leu
2870            2875            2880            2885 aac ttt gag atg tat gga tca gta tac tcc gtg aat cct ttg gac ctt     9043
Asn Phe Glu Met Tyr Gly Ser Val Tyr Ser Val Asn Pro Leu Asp Leu
            2890            2895            2900 cca gcc ata att gag agg tta cac ggg ctt gac gcc ttt tct atg cac     9091
Pro Ala Ile Ile Glu Arg Leu His Gly Leu Asp Ala Phe Ser Met His
        2905            2910            2915 aca tac tct cac cac gaa ctg acg cgg gtg gct tca gcc ctc aga aaa     9139
Thr Tyr Ser His His Glu Leu Thr Arg Val Ala Ser Ala Leu Arg Lys
    2920            2925            2930 ctt ggg gcg cca ccc ctc agg gtg tgg aag agt cgg gct cgc gca gtc     9187
Leu Gly Ala Pro Pro Leu Arg Val Trp Lys Ser Arg Ala Arg Ala Val
2935            2940            2945 agg gcg tcc ctc atc tcc cgt gga ggg aaa gcg gcc gtt tgc ggc cga     9235
Arg Ala Ser Leu Ile Ser Arg Gly Gly Lys Ala Ala Val Cys Gly Arg
2950            2955            2960            2965 tat ctc ttc aat tgg gcg gtg aag acc aag ctc aaa ctc act cca ttg     9283
Tyr Leu Phe Asn Trp Ala Val Lys Thr Lys Leu Lys Leu Thr Pro Leu
            2970            2975            2980 ccg gag gcg cgc cta ctg gac tta tcc agt tgg ttc acc gtc ggc gcc     9331
Pro Glu Ala Arg Leu Leu Asp Leu Ser Ser Trp Phe Thr Val Gly Ala
        2985            2990            2995 ggc ggg ggc gac att ttt cac agc gtg tcg cgc gcc cga ccc cgc tca     9379
Gly Gly Gly Asp Ile Phe His Ser Val Ser Arg Ala Arg Pro Arg Ser
    3000            3005            3010 tta ctc ttc ggc cta ctc cta ctt ttc gta ggg gta ggc ctc ttc cta     9427
Leu Leu Phe Gly Leu Leu Leu Leu Phe Val Gly Val Gly Leu Phe Leu
3015            3020            3025 ctc ccc gct cgg tag agcggcacac actaggtaca ctccatagct aactgttcct     9482
Leu Pro Ala Arg
3030 tttttttttt tttttttttt tttttttttt tttttttttt ttctttttttt tttttttccc     9542 tctttcttcc cttctcatct tattctactt tctttcttgg tggctccatc ttagccctag     9602 tcacggctag ctgtgaaagg tccgtgagcc gcatgactgc agagagtgcc gtaactggtc     9662 tctctgcaga tcatgt                                                     9678
```

<210> SEQ ID NO 4
<211> LENGTH: 3033
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro

-continued

```
                100                 105                 110
Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
            130                 135                 140

Ser Gly Ala Ala Arg Ala Val Ala His Gly Val Arg Val Leu Glu Asp
145                 150                 155                 160

Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
            180                 185                 190

Gln Val Lys Asn Thr Ser Ser Tyr Met Val Thr Asn Asp Cys Ser
            195                 200                 205

Asn Asp Ser Ile Thr Trp Gln Leu Glu Ala Ala Val Leu His Val Pro
210                 215                 220

Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
                245                 250                 255

Gly Leu Arg Thr His Ile Asp Met Val Val Met Ser Ala Thr Phe Cys
            260                 265                 270

Ser Ala Leu Tyr Val Gly Asp Leu Cys Gly Val Met Leu Ala Ala
            275                 280                 285

Gln Val Phe Ile Val Ser Pro Gln Tyr His Trp Phe Val Gln Glu Cys
            290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
            340                 345                 350

Trp Gly Val Met Phe Gly Leu Ala Tyr Phe Ser Met Gln Gly Ala Trp
            355                 360                 365

Ala Lys Val Ile Val Ile Leu Leu Leu Ala Ala Gly Val Asp Ala Gly
            370                 375                 380

Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Thr Asn Arg Phe Asn
            435                 440                 445

Ser Ser Gly Cys Pro Gly Arg Leu Ser Ala Cys Arg Asn Ile Glu Ala
            450                 455                 460

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Pro Lys Pro Cys
                485                 490                 495

Gly Val Val Pro Ala Arg Ser Val Cys Gly Pro Val Tyr Cys Phe Thr
            500                 505                 510

Pro Ser Pro Val Val Val Gly Thr Thr Asp Arg Arg Gly Val Pro Thr
            515                 520                 525
```

```
Tyr Thr Trp Gly Glu Asn Glu Thr Asp Val Phe Leu Leu Asn Ser Thr
530                 535                 540

Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Ala Thr Tyr Ile Lys Cys Gly Ser Gly Pro Trp Leu Thr
                595                 600                 605

Pro Lys Cys Leu Val His Tyr Pro Tyr Arg Leu Trp His Tyr Pro Cys
610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asp Leu Glu Asp Arg Asp Arg Ser Gln Leu Ser Pro Leu Leu His Ser
                660                 665                 670

Thr Thr Glu Trp Ala Ile Leu Pro Cys Thr Tyr Ser Asp Leu Pro Ala
                675                 680                 685

Leu Ser Thr Gly Leu Leu His Leu His Gln Asn Ile Val Asp Val Gln
690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Val Leu His Ala Ala Ser Ala Ala Asn Cys His Gly
                755                 760                 765

Leu Leu Tyr Phe Ala Ile Phe Phe Val Ala Ala Trp His Ile Arg Gly
770                 775                 780

Arg Val Val Pro Leu Thr Thr Tyr Cys Leu Thr Gly Leu Trp Pro Phe
785                 790                 795                 800

Cys Leu Leu Leu Met Ala Leu Pro Arg Gln Ala Tyr Ala Tyr Asp Ala
                805                 810                 815

Pro Val His Gly Gln Ile Gly Val Gly Leu Leu Ile Leu Ile Thr Leu
                820                 825                 830

Phe Thr Leu Thr Pro Gly Tyr Lys Thr Leu Leu Gly Gln Cys Leu Trp
                835                 840                 845

Trp Leu Cys Tyr Leu Leu Thr Leu Gly Glu Ala Met Ile Gln Glu Trp
850                 855                 860

Val Pro Pro Met Gln Val Arg Gly Gly Arg Asp Gly Ile Ala Trp Ala
865                 870                 875                 880

Val Thr Ile Phe Cys Pro Gly Val Val Phe Asp Ile Thr Lys Trp Leu
                885                 890                 895

Leu Ala Leu Leu Gly Pro Ala Tyr Leu Leu Arg Ala Ala Leu Thr His
                900                 905                 910

Val Pro Tyr Phe Val Arg Ala His Ala Leu Ile Arg Val Cys Ala Leu
                915                 920                 925

Val Lys Gln Leu Ala Gly Gly Arg Tyr Val Gln Val Ala Leu Leu Ala
                930                 935                 940

Leu Gly Arg Trp Thr Gly Thr Tyr Ile Tyr Asp His Leu Thr Pro Met
945                 950                 955                 960
```

```
Ser Asp Trp Ala Ala Ser Gly Leu Arg Asp Leu Ala Val Ala Val Glu
            965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
            995                1000                1005

Arg Leu Gly Gln Glu Ile Leu Leu Gly Pro Ala Asp Gly Tyr Thr Ser
           1010                1015                1020

Lys Gly Trp Lys Leu Leu Ala Pro Ile Thr Ala Tyr Ala Gln Gln Thr
1025                1030                1035                1040

Arg Gly Leu Leu Gly Ala Ile Val Val Ser Met Thr Gly Arg Asp Arg
           1045                1050                1055

Thr Glu Gln Ala Gly Glu Val Gln Ile Leu Ser Thr Val Ser Gln Ser
           1060                1065                1070

Phe Leu Gly Thr Thr Ile Ser Gly Val Leu Trp Thr Val Tyr His Gly
           1075                1080                1085

Ala Gly Asn Lys Thr Leu Ala Gly Leu Arg Gly Pro Val Thr Gln Met
           1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Lys Cys Gly Ala Val Asp Leu Tyr Leu
           1125                1130                1135

Val Thr Arg Asn Ala Asp Val Ile Pro Ala Arg Arg Arg Gly Asp Lys
           1140                1145                1150

Arg Gly Ala Leu Leu Ser Pro Arg Pro Ile Ser Thr Leu Lys Gly Ser
           1155                1160                1165

Ser Gly Gly Pro Val Leu Cys Pro Arg Gly His Val Val Gly Leu Phe
           1170                1175                1180

Arg Ala Ala Val Cys Ser Arg Gly Val Ala Lys Ser Ile Asp Phe Ile
1185                1190                1195                1200

Pro Val Glu Thr Leu Asp Val Val Thr Arg Ser Pro Thr Phe Ser Asp
           1205                1210                1215

Asn Ser Thr Pro Pro Ala Val Pro Gln Thr Tyr Gln Val Gly Tyr Leu
           1220                1225                1230

His Ala Pro Thr Gly Ser Gly Lys Ser Thr Lys Val Pro Val Ala Tyr
           1235                1240                1245

Ala Ala Gln Gly Tyr Lys Val Leu Val Leu Asn Pro Ser Val Ala Ala
           1250                1255                1260

Thr Leu Gly Phe Gly Ala Tyr Leu Ser Lys Ala His Gly Ile Asn Pro
1265                1270                1275                1280

Asn Ile Arg Thr Gly Val Arg Thr Val Met Thr Gly Glu Ala Ile Thr
           1285                1290                1295

Tyr Ser Thr Tyr Gly Lys Phe Leu Ala Asp Gly Gly Cys Ala Ser Gly
           1300                1305                1310

Ala Tyr Asp Ile Ile Ile Cys Asp Glu Cys His Ala Val Asp Ala Thr
           1315                1320                1325

Ser Ile Leu Gly Ile Gly Thr Val Leu Asp Gln Ala Glu Thr Ala Gly
           1330                1335                1340

Val Arg Leu Thr Val Leu Ala Thr Ala Thr Pro Pro Gly Ser Val Thr
1345                1350                1355                1360

Thr Pro His Pro Asp Ile Glu Glu Val Gly Leu Gly Arg Glu Gly Glu
           1365                1370                1375

Ile Pro Phe Tyr Gly Arg Ala Ile Pro Leu Ser Cys Ile Lys Gly Gly
```

-continued

```
            1380                1385                1390
Arg His Leu Ile Phe Cys His Ser Lys Lys Cys Asp Glu Leu Ala
        1395                1400                1405
Ala Ala Leu Arg Gly Met Gly Leu Asn Ala Val Ala Tyr Tyr Arg Gly
    1410                1415                1420
Leu Asp Val Ser Ile Ile Pro Ala Gln Gly Asp Val Val Val Ala
1425                1430                1435                1440
Thr Asp Ala Leu Met Thr Gly Tyr Thr Gly Asp Phe Asp Ser Val Ile
            1445                1450                1455
Asp Cys Asn Val Ala Val Thr Gln Ala Val Asp Phe Ser Leu Asp Pro
        1460                1465                1470
Thr Phe Thr Ile Thr Thr Gln Thr Val Pro Gln Asp Ala Val Ser Arg
    1475                1480                1485
Ser Gln Arg Arg Gly Arg Thr Gly Arg Gly Arg Gln Gly Thr Tyr Arg
    1490                1495                1500
Tyr Val Ser Thr Gly Glu Arg Ala Ser Gly Met Phe Asp Ser Val Val
1505                1510                1515                1520
Leu Cys Glu Cys Tyr Asp Ala Gly Ala Ala Trp Tyr Asp Leu Thr Pro
        1525                1530                1535
Ala Glu Thr Thr Val Arg Leu Arg Ala Tyr Phe Asn Thr Pro Gly Leu
            1540                1545                1550
Pro Val Cys Gln Asp His Leu Glu Phe Trp Glu Ala Val Phe Thr Gly
        1555                1560                1565
Leu Thr His Ile Asp Ala His Phe Leu Ser Gln Thr Lys Gln Ala Gly
        1570                1575                1580
Glu Asn Phe Ala Tyr Leu Val Ala Tyr Gln Ala Thr Val Cys Ala Arg
1585                1590                1595                1600
Ala Lys Ala Pro Pro Pro Ser Trp Asp Ala Met Trp Lys Cys Leu Ala
            1605                1610                1615
Arg Leu Lys Pro Thr Leu Ala Gly Pro Thr Pro Leu Leu Tyr Arg Leu
        1620                1625                1630
Gly Pro Ile Thr Asn Glu Val Thr Leu Thr His Pro Gly Thr Lys Tyr
        1635                1640                1645
Ile Ala Thr Cys Met Gln Ala Asp Leu Glu Val Met Thr Ser Thr Trp
        1650                1655                1660
Val Leu Ala Gly Gly Val Leu Ala Ala Val Ala Ala Tyr Cys Leu Ala
1665                1670                1675                1680
Thr Gly Cys Val Ser Ile Ile Gly Arg Leu His Val Asn Gln Arg Val
            1685                1690                1695
Val Val Ala Pro Asp Lys Glu Val Leu Tyr Glu Ala Phe Asp Glu Met
            1700                1705                1710
Glu Glu Cys Ala Ser Arg Ala Ala Leu Ile Glu Glu Gly Gln Arg Ile
        1715                1720                1725
Ala Glu Met Leu Lys Ser Lys Ile Gln Gly Leu Leu Gln Gln Ala Ser
        1730                1735                1740
Lys Gln Ala Gln Asp Ile Gln Pro Ala Met Gln Ala Ser Trp Pro Lys
1745                1750                1755                1760
Val Glu Gln Phe Trp Ala Arg His Met Trp Asn Phe Ile Ser Gly Ile
            1765                1770                1775
Gln Tyr Leu Ala Gly Leu Ser Thr Leu Pro Gly Asn Pro Ala Val Ala
        1780                1785                1790
Ser Met Met Ala Phe Ser Ala Ala Leu Thr Ser Pro Leu Ser Thr Ser
        1795                1800                1805
```

-continued

Thr Thr Ile Leu Leu Asn Ile Met Gly Gly Trp Leu Ala Ser Gln Ile
    1810                1815                1820

Ala Pro Pro Ala Gly Ala Thr Gly Phe Val Val Ser Gly Leu Val Gly
1825                1830                1835                1840

Ala Ala Val Gly Ser Ile Gly Leu Gly Lys Val Leu Val Asp Ile Leu
            1845                1850                1855

Ala Gly Tyr Gly Ala Gly Ile Ser Gly Ala Leu Val Ala Phe Lys Ile
        1860                1865                1870

Met Ser Gly Glu Lys Pro Ser Met Glu Asp Val Ile Asn Leu Leu Pro
    1875                1880                1885

Gly Ile Leu Ser Pro Gly Ala Leu Val Val Gly Val Ile Cys Ala Ala
    1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ala Pro Thr
            1925                1930                1935

His Tyr Val Thr Glu Ser Asp Ala Ser Gln Arg Val Thr Gln Leu Leu
            1940                1945                1950

Gly Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp Val
    1970                1975                1980

Trp Asp Trp Val Cys Thr Ile Leu Thr Asp Phe Lys Asn Trp Leu Thr
1985                1990                1995                2000

Ser Lys Leu Phe Pro Lys Leu Pro Gly Leu Pro Phe Ile Ser Cys Gln
        2005                2010                2015

Lys Gly Tyr Lys Gly Val Trp Ala Gly Thr Gly Ile Met Thr Thr Arg
        2020                2025                2030

Cys Pro Cys Gly Ala Asn Ile Ser Gly Asn Val Arg Leu Gly Ser Met
    2035                2040                2045

Arg Ile Thr Gly Pro Lys Thr Cys Met Asn Thr Trp Gln Gly Thr Phe
    2050                2055                2060

Pro Ile Asn Cys Tyr Thr Glu Gly Gln Cys Ala Pro Lys Pro Pro Thr
2065                2070                2075                2080

Asn Tyr Lys Thr Ala Ile Trp Arg Val Ala Ala Ser Glu Tyr Ala Glu
        2085                2090                2095

Val Thr Gln His Gly Ser Tyr Ser Tyr Val Thr Gly Leu Thr Thr Asp
        2100                2105                2110

Asn Leu Lys Ile Pro Cys Gln Leu Pro Ser Pro Glu Phe Phe Ser Trp
    2115                2120                2125

Val Asp Gly Val Gln Ile His Arg Phe Ala Pro Thr Pro Lys Pro Phe
    2130                2135                2140

Phe Arg Asp Glu Val Ser Phe Cys Val Gly Leu Asn Ser Tyr Ala Val
2145                2150                2155                2160

Gly Ser Gln Leu Pro Cys Glu Pro Glu Pro Asp Ala Asp Val Leu Arg
            2165                2170                2175

Ser Met Leu Thr Asp Pro Pro His Ile Thr Ala Glu Thr Ala Ala Arg
        2180                2185                2190

Arg Leu Ala Arg Gly Ser Pro Pro Ser Glu Ala Ser Ser Ser Val Ser
        2195                2200                2205

Gln Leu Ser Ala Pro Ser Leu Arg Ala Thr Cys Thr Thr His Ser Asn
    2210                2215                2220

Thr Tyr Asp Val Asp Met Val Asp Ala Asn Leu Leu Met Glu Gly Gly
2225                2230                2235                2240

-continued

Val Ala Gln Thr Glu Pro Glu Ser Arg Val Pro Val Leu Asp Phe Leu
        2245                2250                2255

Glu Pro Met Ala Glu Glu Ser Asp Leu Glu Pro Ser Ile Pro Ser
        2260                2265                2270

Glu Cys Met Leu Pro Arg Ser Gly Phe Pro Arg Ala Leu Pro Ala Trp
        2275                2280                2285

Ala Arg Pro Asp Tyr Asn Pro Pro Leu Val Glu Ser Trp Arg Arg Pro
    2290                2295                2300

Asp Tyr Gln Pro Pro Thr Val Ala Gly Cys Ala Leu Pro Pro Lys
2305                2310                2315                2320

Lys Ala Pro Thr Pro Pro Pro Arg Arg Arg Arg Thr Val Gly Leu Ser
        2325                2330                2335

Glu Ser Thr Ile Ser Glu Ala Leu Gln Gln Leu Ala Ile Lys Thr Phe
        2340                2345                2350

Gly Gln Pro Pro Ser Ser Gly Asp Ala Gly Ser Ser Thr Gly Ala Gly
        2355                2360                2365

Ala Ala Glu Ser Gly Gly Pro Thr Ser Pro Gly Glu Pro Ala Pro Ser
    2370                2375                2380

Glu Thr Gly Ser Ala Ser Ser Met Pro Pro Leu Glu Gly Glu Pro Gly
2385                2390                2395                2400

Asp Pro Asp Leu Glu Ser Asp Gln Val Glu Leu Gln Pro Pro Pro Gln
        2405                2410                2415

Gly Gly Gly Val Ala Pro Gly Ser Gly Ser Gly Ser Trp Ser Thr Cys
        2420                2425                2430

Ser Glu Glu Asp Asp Thr Thr Val Cys Cys Ser Met Ser Tyr Ser Trp
    2435                2440                2445

Thr Gly Ala Leu Ile Thr Pro Cys Ser Pro Glu Glu Lys Leu Pro
        2450                2455                2460

Ile Asn Pro Leu Ser Asn Ser Leu Leu Arg Tyr His Asn Lys Val Tyr
2465                2470                2475                2480

Cys Thr Thr Ser Lys Ser Ala Ser Gln Arg Ala Lys Lys Val Thr Phe
        2485                2490                2495

Asp Arg Thr Gln Val Leu Asp Ala His Tyr Asp Ser Val Leu Lys Asp
        2500                2505                2510

Ile Lys Leu Ala Ala Ser Lys Val Ser Ala Arg Leu Leu Thr Leu Glu
    2515                2520                2525

Glu Ala Cys Gln Leu Thr Pro Pro His Ser Ala Arg Ser Lys Tyr Gly
    2530                2535                2540

Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Pro Gln Thr Pro Ile
        2565                2570                2575

Pro Thr Thr Ile Met Ala Lys Asn Glu Val Phe Cys Val Asp Pro Ala
        2580                2585                2590

Lys Gly Gly Lys Lys Pro Ala Arg Leu Ile Val Tyr Pro Asp Leu Gly
    2595                2600                2605

Val Arg Val Cys Glu Lys Met Ala Leu Tyr Asp Ile Thr Gln Lys Leu
    2610                2615                2620

Pro Gln Ala Val Met Gly Ala Ser Tyr Gly Phe Gln Tyr Ser Pro Ala
2625                2630                2635                2640

Gln Arg Val Glu Tyr Leu Leu Lys Ala Trp Ala Glu Lys Lys Asp Pro
        2645                2650                2655

Met Gly Phe Ser Tyr Asp Thr Arg Cys Phe Asp Ser Thr Val Thr Glu 2660                2665                2670
Arg Asp Ile Arg Thr Glu Glu Ser Ile Tyr Gln Ala Cys Ser Leu Pro
        2675                2680                2685

Glu Glu Ala Arg Thr Ala Ile His Ser Leu Thr Glu Arg Leu Tyr Val
    2690                2695                2700

Gly Gly Pro Met Phe Asn Ser Lys Gly Gln Thr Cys Gly Tyr Arg Arg
2705                2710                2715                2720

Cys Arg Ala Ser Gly Val Leu Thr Thr Ser Met Gly Asn Thr Ile Thr
            2725                2730                2735

Cys Tyr Val Lys Ala Leu Ala Ala Cys Lys Ala Ala Gly Ile Val Ala
        2740                2745                2750

Pro Thr Met Leu Val Cys Gly Asp Asp Leu Val Val Ile Ser Glu Ser
    2755                2760                2765

Gln Gly Thr Glu Glu Asp Glu Arg Asn Leu Arg Ala Phe Thr Glu Ala
2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
            2805                2810                2815

Gly Pro Arg Gly Arg Arg Arg Tyr Tyr Leu Thr Arg Asp Pro Thr Thr
        2820                2825                2830

Pro Leu Ala Arg Ala Ala Trp Glu Thr Val Arg His Ser Pro Ile Asn
    2835                2840                2845

Ser Trp Leu Gly Asn Ile Ile Gln Tyr Ala Pro Thr Ile Trp Val Arg
2850                2855                2860

Met Val Leu Met Thr His Phe Phe Ser Ile Leu Met Val Gln Asp Thr
2865                2870                2875                2880

Leu Asp Gln Asn Leu Asn Phe Glu Met Tyr Gly Ser Val Tyr Ser Val
            2885                2890                2895

Asn Pro Leu Asp Leu Pro Ala Ile Ile Glu Arg Leu His Gly Leu Asp
        2900                2905                2910

Ala Phe Ser Met His Thr Tyr Ser His His Glu Leu Thr Arg Val Ala
    2915                2920                2925

Ser Ala Leu Arg Lys Leu Gly Ala Pro Pro Leu Arg Val Trp Lys Ser
2930                2935                2940

Arg Ala Arg Ala Val Arg Ala Ser Leu Ile Ser Arg Gly Gly Lys Ala
2945                2950                2955                2960

Ala Val Cys Gly Arg Tyr Leu Phe Asn Trp Ala Val Lys Thr Lys Leu
            2965                2970                2975

Lys Leu Thr Pro Leu Pro Glu Ala Arg Leu Leu Asp Leu Ser Ser Trp
        2980                2985                2990

Phe Thr Val Gly Ala Gly Gly Gly Asp Ile Phe His Ser Val Ser Arg
    2995                3000                3005

Ala Arg Pro Arg Ser Leu Leu Phe Gly Leu Leu Leu Leu Phe Val Gly
        3010                3015                3020

Val Gly Leu Phe Leu Leu Pro Ala Arg
3025                3030

<210> SEQ ID NO 5
<211> LENGTH: 9674
<212> TYPE: DNA
<213> ORGANISM: Hepatitis C virus
<220> FEATURE:
<221> NAME/KEY: CDS
<222> LOCATION: (341)..(9442)

<400> SEQUENCE: 5

```
acccgcccct aatagggggcg acactccgcc atgaatcact cccctgtgag gaactactgt      60
cttcacgcag aaagcgtcta gccatggcgt tagtatgagt gtcgtacagc ctccaggccc     120
ccccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
tgcttgcgag tgccccggga ggtctcgtag accgtgcacc atg agc aca aat ccc       355
                                              Met Ser Thr Asn Pro
                                              1               5
```

| | | | | | | | | | | | | | | | | |
|---|---|---|---|---|---|---|---|---|---|---|---|---|---|---|---|---|
| aaa | cct | caa | aga | aaa | acc | aaa | aga | aac | act | aac | cgt | cgc | cca | caa | gac | 403 |
| Lys | Pro | Gln | Arg | Lys | Thr | Lys | Arg | Asn | Thr | Asn | Arg | Arg | Pro | Gln | Asp | |
| | | | 10 | | | | 15 | | | | | 20 | | | | |

| | | | | | | | | | | | | | | | | |
|---|---|---|---|---|---|---|---|---|---|---|---|---|---|---|---|---|
| gtt | aag | ttt | ccg | ggc | ggc | ggc | cag | atc | gtt | ggc | gga | gta | tac | ttg | ttg | 451 |
| Val | Lys | Phe | Pro | Gly | Gly | Gly | Gln | Ile | Val | Gly | Gly | Val | Tyr | Leu | Leu | |
| | | | 25 | | | | 30 | | | | | 35 | | | | |

| | | | | | | | | | | | | | | | | |
|---|---|---|---|---|---|---|---|---|---|---|---|---|---|---|---|---|
| ccg | cgc | agg | ggc | ccc | agg | ttg | ggt | gtg | cgc | gcg | aca | agg | aag | gct | tcg | 499 |
| Pro | Arg | Arg | Gly | Pro | Arg | Leu | Gly | Val | Arg | Ala | Thr | Arg | Lys | Ala | Ser | |
| | | | 40 | | | | 45 | | | | | 50 | | | | |

| | | | | | | | | | | | | | | | | |
|---|---|---|---|---|---|---|---|---|---|---|---|---|---|---|---|---|
| gag | cgg | tcc | cag | cca | cgt | ggg | agg | cgc | cag | ccc | atc | ccc | aaa | cat | cgg | 547 |
| Glu | Arg | Ser | Gln | Pro | Arg | Gly | Arg | Arg | Gln | Pro | Ile | Pro | Lys | His | Arg | |
| | 55 | | | | 60 | | | | 65 | | | | | | | |

| | | | | | | | | | | | | | | | | |
|---|---|---|---|---|---|---|---|---|---|---|---|---|---|---|---|---|
| cgc | tcc | act | ggc | aag | tcc | tgg | ggg | aag | cca | gga | tac | ccc | tgg | ccc | ctg | 595 |
| Arg | Ser | Thr | Gly | Lys | Ser | Trp | Gly | Lys | Pro | Gly | Tyr | Pro | Trp | Pro | Leu | |
| 70 | | | | 75 | | | | 80 | | | | | | | 85 | |

| | | | | | | | | | | | | | | | | |
|---|---|---|---|---|---|---|---|---|---|---|---|---|---|---|---|---|
| tat | ggg | aat | gag | ggg | ctc | ggt | tgg | gca | gga | tgg | ctc | ctg | tcc | cct | cga | 643 |
| Tyr | Gly | Asn | Glu | Gly | Leu | Gly | Trp | Ala | Gly | Trp | Leu | Leu | Ser | Pro | Arg | |
| | | | 90 | | | | 95 | | | | | 100 | | | | |

| | | | | | | | | | | | | | | | | |
|---|---|---|---|---|---|---|---|---|---|---|---|---|---|---|---|---|
| ggt | tcc | cgt | ccc | tca | tgg | ggc | ccc | aat | gac | ccc | cgg | cat | agg | tcg | cgc | 691 |
| Gly | Ser | Arg | Pro | Ser | Trp | Gly | Pro | Asn | Asp | Pro | Arg | His | Arg | Ser | Arg | |
| | | | 105 | | | | 110 | | | | | 115 | | | | |

| | | | | | | | | | | | | | | | | |
|---|---|---|---|---|---|---|---|---|---|---|---|---|---|---|---|---|
| aat | gtg | ggt | aag | gtc | atc | gat | acc | cta | acg | tgc | ggc | ttt | gcc | gac | ctc | 739 |
| Asn | Val | Gly | Lys | Val | Ile | Asp | Thr | Leu | Thr | Cys | Gly | Phe | Ala | Asp | Leu | |
| | | | 120 | | | | 125 | | | | | 130 | | | | |

| | | | | | | | | | | | | | | | | |
|---|---|---|---|---|---|---|---|---|---|---|---|---|---|---|---|---|
| ttg | ggg | tac | gtc | ccc | gtc | gta | ggc | gcc | ccg | ctt | agt | ggc | gtt | gcc | agt | 787 |
| Leu | Gly | Tyr | Val | Pro | Val | Val | Gly | Ala | Pro | Leu | Ser | Gly | Val | Ala | Ser | |
| 135 | | | | 140 | | | | | | | 145 | | | | | |

| | | | | | | | | | | | | | | | | |
|---|---|---|---|---|---|---|---|---|---|---|---|---|---|---|---|---|
| gct | ctc | gcg | cac | ggc | gtg | aga | gtc | ctg | gag | gac | ggg | gtt | aat | ttt | gca | 835 |
| Ala | Leu | Ala | His | Gly | Val | Arg | Val | Leu | Glu | Asp | Gly | Val | Asn | Phe | Ala | |
| 150 | | | | 155 | | | | | | | 160 | | | | 165 | |

| | | | | | | | | | | | | | | | | |
|---|---|---|---|---|---|---|---|---|---|---|---|---|---|---|---|---|
| aca | ggg | aac | tta | cct | ggt | tgc | tcc | ttt | tct | atc | ttc | ttg | ctg | gcc | cta | 883 |
| Thr | Gly | Asn | Leu | Pro | Gly | Cys | Ser | Phe | Ser | Ile | Phe | Leu | Leu | Ala | Leu | |
| | | | 170 | | | | 175 | | | | | 180 | | | | |

| | | | | | | | | | | | | | | | | |
|---|---|---|---|---|---|---|---|---|---|---|---|---|---|---|---|---|
| ctg | tcc | tgc | atc | act | act | ccg | gtc | tct | gct | gtc | caa | gtg | aag | aac | acc | 931 |
| Leu | Ser | Cys | Ile | Thr | Thr | Pro | Val | Ser | Ala | Val | Gln | Val | Lys | Asn | Thr | |
| | | | 185 | | | | 190 | | | | | 195 | | | | |

| | | | | | | | | | | | | | | | | |
|---|---|---|---|---|---|---|---|---|---|---|---|---|---|---|---|---|
| agc | aac | gcc | tat | atg | gcg | act | aac | gac | tgt | tcc | aat | gac | agc | atc | act | 979 |
| Ser | Asn | Ala | Tyr | Met | Ala | Thr | Asn | Asp | Cys | Ser | Asn | Asp | Ser | Ile | Thr | |
| | | 200 | | | | | 205 | | | | | 210 | | | | |

| | | | | | | | | | | | | | | | | |
|---|---|---|---|---|---|---|---|---|---|---|---|---|---|---|---|---|
| tgg | cag | ctt | gag | gcc | gca | gtc | ctc | cat | gtc | ccc | ggg | tgc | gtc | ccg | tgc | 1027 |
| Trp | Gln | Leu | Glu | Ala | Ala | Val | Leu | His | Val | Pro | Gly | Cys | Val | Pro | Cys | |
| | 215 | | | | 220 | | | | | 225 | | | | | | |

| | | | | | | | | | | | | | | | | |
|---|---|---|---|---|---|---|---|---|---|---|---|---|---|---|---|---|
| gag | aaa | atg | ggg | aac | aca | tca | cgg | tgc | tgg | ata | cca | gtc | tca | cca | aac | 1075 |
| Glu | Lys | Met | Gly | Asn | Thr | Ser | Arg | Cys | Trp | Ile | Pro | Val | Ser | Pro | Asn | |
| 230 | | | | 235 | | | | | | | 240 | | | | 245 | |

| | | | | | | | | | | | | | | | | |
|---|---|---|---|---|---|---|---|---|---|---|---|---|---|---|---|---|
| gtg | gct | gtg | cgg | cag | cct | ggc | gcc | ctc | acg | cgg | ggc | ttg | cgg | acg | cac | 1123 |
| Val | Ala | Val | Arg | Gln | Pro | Gly | Ala | Leu | Thr | Arg | Gly | Leu | Arg | Thr | His | |
| | | | 250 | | | | 255 | | | | | 260 | | | | |

```
                                                                -continued
atc gac atg gtc gtg ttg tcc gcc acg ctc tgc tcc gct ctc tac gtg   1171
Ile Asp Met Val Val Leu Ser Ala Thr Leu Cys Ser Ala Leu Tyr Val
            265                 270                 275 ggg gac ctc tgt ggc ggg gtg atg ctc gcg tcc cag atg ttc att gtc   1219
Gly Asp Leu Cys Gly Gly Val Met Leu Ala Ser Gln Met Phe Ile Val
        280                 285                 290 tcg ccg cag cac cac tgg ttc gtg cag gaa tgc aat tgc tcc atc tac   1267
Ser Pro Gln His His Trp Phe Val Gln Glu Cys Asn Cys Ser Ile Tyr
    295                 300                 305 cct ggc gcc atc act ggg cac cgt atg gca tgg gac atg atg atg aac   1315
Pro Gly Ala Ile Thr Gly His Arg Met Ala Trp Asp Met Met Met Asn
310                 315                 320                 325 tgg tcg ccc acg acc acc atg atc ctg gcg tac gtg atg cgc gtt ccc   1363
Trp Ser Pro Thr Thr Thr Met Ile Leu Ala Tyr Val Met Arg Val Pro
            330                 335                 340 gag gtc atc ata gac atc att agc gga gct cac tgg ggc gtc atg ttt   1411
Glu Val Ile Ile Asp Ile Ile Ser Gly Ala His Trp Gly Val Met Phe
        345                 350                 355 ggc ctg gcc tac ttc tct atg cag gga gcg tgg gcg aag gtc gtt gtc   1459
Gly Leu Ala Tyr Phe Ser Met Gln Gly Ala Trp Ala Lys Val Val Val
    360                 365                 370 atc ctc ctg ctg gcc tct ggg gtg gac gcg tac acc acc acg act ggg   1507
Ile Leu Leu Leu Ala Ser Gly Val Asp Ala Tyr Thr Thr Thr Thr Gly
375                 380                 385 agc gct gct ggg cgc act acc agt agc ctg gcc agc gcc ttc tcc cct   1555
Ser Ala Ala Gly Arg Thr Thr Ser Ser Leu Ala Ser Ala Phe Ser Pro
390                 395                 400                 405 ggc gct cgg cag aac att cag ctc att aat acc aat ggt agc tgg cac   1603
Gly Ala Arg Gln Asn Ile Gln Leu Ile Asn Thr Asn Gly Ser Trp His
            410                 415                 420 atc aac cgc acc gcc ctg aat tgc aac gat tcc ttg cac acc ggc ttc   1651
Ile Asn Arg Thr Ala Leu Asn Cys Asn Asp Ser Leu His Thr Gly Phe
        425                 430                 435 ttc acg gcc ctg ttc tac atc cat aag ttc aac tcg tcg gga tgt ccc   1699
Phe Thr Ala Leu Phe Tyr Ile His Lys Phe Asn Ser Ser Gly Cys Pro
    440                 445                 450 gag cgc ctg tcc gcc tgt cgc aac atc gag gac ttc cgg ata gga tgg   1747
Glu Arg Leu Ser Ala Cys Arg Asn Ile Glu Asp Phe Arg Ile Gly Trp
455                 460                 465 ggc gcc ctg caa tac gac gac aat gtc acc aat cca gaa gat atg agg   1795
Gly Ala Leu Gln Tyr Asp Asp Asn Val Thr Asn Pro Glu Asp Met Arg
            470                 475                 480                 485 cca tat tgc tgg cac tac cca cca aaa cag tgt ggc gta gtc ccc gca   1843
Pro Tyr Cys Trp His Tyr Pro Pro Lys Gln Cys Gly Val Val Pro Ala
        490                 495                 500 ggg acc gtg tgc ggc cca gtg tac tgt ttc acc cct agc ccg gtg gta   1891
Gly Thr Val Cys Gly Pro Val Tyr Cys Phe Thr Pro Ser Pro Val Val
    505                 510                 515 gtg ggc acg acc gat aga ctt gga gtg cct act tac acg tgg gga gag   1939
Val Gly Thr Thr Asp Arg Leu Gly Val Pro Thr Tyr Thr Trp Gly Glu
520                 525                 530 aat gag aca gat gtc ttc cta ttg aac agc acc cga cca ccg tcg ggg   1987
Asn Glu Thr Asp Val Phe Leu Leu Asn Ser Thr Arg Pro Pro Ser Gly
            535                 540                 545 tca tgg ttt ggc tgc acg tgg atg aac tcc act ggc ttc acc aag acc   2035
Ser Trp Phe Gly Cys Thr Trp Met Asn Ser Thr Gly Phe Thr Lys Thr
550                 555                 560                 565 tgc ggc gca cca ccc tgc cgc act aga gct gac ttc aat acc agc aca   2083
Cys Gly Ala Pro Pro Cys Arg Thr Arg Ala Asp Phe Asn Thr Ser Thr
        570                 575                 580
```

```
                                                       -continued gat ctg ttg tgc ccc acg gac tgt ttt aga aaa cat cct gaa gcc act       2131
Asp Leu Leu Cys Pro Thr Asp Cys Phe Arg Lys His Pro Glu Ala Thr
            585                 590                 595 tac atc aaa tgt ggt tcc ggg cct tgg ctc acg cca aag tgt ctg gtt       2179
Tyr Ile Lys Cys Gly Ser Gly Pro Trp Leu Thr Pro Lys Cys Leu Val
            600                 605                 610 gac tac ccc tac agg ctc tgg cat tac cct tgc aca gtc aat tac tcc       2227
Asp Tyr Pro Tyr Arg Leu Trp His Tyr Pro Cys Thr Val Asn Tyr Ser
            615                 620                 625 acc ttc aag atc agg atg tat gtg ggg gga gtt gag cac agg ctc atg       2275
Thr Phe Lys Ile Arg Met Tyr Val Gly Gly Val Glu His Arg Leu Met
630                 635                 640                 645 gcc gcg tgc aat ttc act cgt ggg gat cgc tgc aac ttg gag gat agg       2323
Ala Ala Cys Asn Phe Thr Arg Gly Asp Arg Cys Asn Leu Glu Asp Arg
                650                 655                 660 gac aga agt caa cag act cct ctg ttg cac tcc acc acg gaa tgg gcc       2371
Asp Arg Ser Gln Gln Thr Pro Leu Leu His Ser Thr Thr Glu Trp Ala
                665                 670                 675 att ttg ccc tgc tct ttc tca gac ttg ccc gct ttg tcg act ggt ctt       2419
Ile Leu Pro Cys Ser Phe Ser Asp Leu Pro Ala Leu Ser Thr Gly Leu
                680                 685                 690 ctc cac ctc cac caa aat atc gtg gac gta caa tat atg tat ggc ctg       2467
Leu His Leu His Gln Asn Ile Val Asp Val Gln Tyr Met Tyr Gly Leu
            695                 700                 705 tca cct gcc ctc aca caa tat atc gtt cga tgg gag tgg gta gta ctc       2515
Ser Pro Ala Leu Thr Gln Tyr Ile Val Arg Trp Glu Trp Val Val Leu
710                 715                 720                 725 tta ttc ctg ctc cta gcg gac gcc agg gtc tgc gcc tgc ttg tgg atg       2563
Leu Phe Leu Leu Leu Ala Asp Ala Arg Val Cys Ala Cys Leu Trp Met
                730                 735                 740 ctc atc ttg ctg ggc caa gcc gaa gca gca ctg gag aag ctg gtc gtc       2611
Leu Ile Leu Leu Gly Gln Ala Glu Ala Ala Leu Glu Lys Leu Val Val
                745                 750                 755 ttg cac gct gcg agc gca gct agc tgc aat ggc ttc ctg tat ttt gtc       2659
Leu His Ala Ala Ser Ala Ala Ser Cys Asn Gly Phe Leu Tyr Phe Val
            760                 765                 770 atc ttt ctc gtg gct gct tgg cac atc aag ggt agg gtg gtc ccc ttg       2707
Ile Phe Leu Val Ala Ala Trp His Ile Lys Gly Arg Val Val Pro Leu
775                 780                 785 gct gct tat tcc ctt act ggc ctg tgg ccg ttc tgc cta ctg ctc cta       2755
Ala Ala Tyr Ser Leu Thr Gly Leu Trp Pro Phe Cys Leu Leu Leu Leu
790                 795                 800                 805 gca ctg ccc cag cag gct tac gcc tat gat gca tct gtg cac gga cag       2803
Ala Leu Pro Gln Gln Ala Tyr Ala Tyr Asp Ala Ser Val His Gly Gln
                810                 815                 820 gtg ggc gcg gct ttg cta gta ctg att acc ctc ttt aca ctc acc ccg       2851
Val Gly Ala Ala Leu Leu Val Leu Ile Thr Leu Phe Thr Leu Thr Pro
            825                 830                 835 ggg tat aag acc ctt ctc agc cag tcc ctg tgg tgg ttg tgc tat ctc       2899
Gly Tyr Lys Thr Leu Leu Ser Gln Ser Leu Trp Trp Leu Cys Tyr Leu
            840                 845                 850 ctg acc ctg gcg gaa acc atg gtc cag gag tgg gca cca tcc atg cag       2947
Leu Thr Leu Ala Glu Thr Met Val Gln Glu Trp Ala Pro Ser Met Gln
855                 860                 865 gcg cgc ggc ggc cgt gat ggc atc ata tgg gcc gcc acc ata ttt tgc       2995
Ala Arg Gly Gly Arg Asp Gly Ile Ile Trp Ala Ala Thr Ile Phe Cys
870                 875                 880                 885 ccg ggc gta gtg ttt gac ata acc aag tgg ctc tta gcg gtg ctt ggg       3043
Pro Gly Val Val Phe Asp Ile Thr Lys Trp Leu Leu Ala Val Leu Gly
                890                 895                 900
```

```
cct ggt tac ctc cta aga ggt gct ttg acg cgc gtg cca tat ttc gtc    3091
Pro Gly Tyr Leu Leu Arg Gly Ala Leu Thr Arg Val Pro Tyr Phe Val
        905                 910                 915 aga gcc cac gct ctg ctg aga atg tgc act atg gtg agg cac ctc gcg    3139
Arg Ala His Ala Leu Leu Arg Met Cys Thr Met Val Arg His Leu Ala
    920                 925                 930 ggg ggt agg tac gtc cag atg gcg cta tta gcc ctt ggc agg tgg act    3187
Gly Gly Arg Tyr Val Gln Met Ala Leu Leu Ala Leu Gly Arg Trp Thr
935                 940                 945 ggc act tac atc tat gac cac ctc acc cct atg tcg gat tgg gct gct    3235
Gly Thr Tyr Ile Tyr Asp His Leu Thr Pro Met Ser Asp Trp Ala Ala
950                 955                 960                 965 agc ggc ctg cgg gac ttg gcg gtc gct gtg gag cct atc atc ttc agt    3283
Ser Gly Leu Arg Asp Leu Ala Val Ala Val Glu Pro Ile Ile Phe Ser
            970                 975                 980 ccg atg gag aag aaa gtc atc gtt tgg gga gcg gag acg gct gcg tgc    3331
Pro Met Glu Lys Lys Val Ile Val Trp Gly Ala Glu Thr Ala Ala Cys
                985                 990                 995 ggg gac atc ttg cac gga ctt ccc gtg tcc gcc cga ctc ggt cgg gag    3379
Gly Asp Ile Leu His Gly Leu Pro Val Ser Ala Arg Leu Gly Arg Glu
        1000                1005                1010 atc ctc ctt ggc cca gct gat ggc tac acc tcc aag ggg tgg aag ctt    3427
Ile Leu Leu Gly Pro Ala Asp Gly Tyr Thr Ser Lys Gly Trp Lys Leu
    1015                1020                1025 ctc gcc ccc atc acc gct tac gcc cag cag aca cga ggt ctc ttg ggc    3475
Leu Ala Pro Ile Thr Ala Tyr Ala Gln Gln Thr Arg Gly Leu Leu Gly
1030                1035                1040                1045 tct ata gtg gtg agc atg acg ggg cgt gac aag aca gaa cag gcc ggg    3523
Ser Ile Val Val Ser Met Thr Gly Arg Asp Lys Thr Glu Gln Ala Gly
            1050                1055                1060 gag gtc caa gtc ctg tcc aca gtc act cag tcc ttc ctc gga aca tcc    3571
Glu Val Gln Val Leu Ser Thr Val Thr Gln Ser Phe Leu Gly Thr Ser
                1065                1070                1075 att tcg ggg gtc tta tgg act gtt tac cac gga gct ggc aac aag aca    3619
Ile Ser Gly Val Leu Trp Thr Val Tyr His Gly Ala Gly Asn Lys Thr
        1080                1085                1090 cta gcc ggc tcg cgg ggc ccg gtc acg cag atg tac tcg agc gcc gag    3667
Leu Ala Gly Ser Arg Gly Pro Val Thr Gln Met Tyr Ser Ser Ala Glu
    1095                1100                1105 ggg gac ttg gtc ggg tgg ccc agc cct cct ggg acc aaa tct ttg gag    3715
Gly Asp Leu Val Gly Trp Pro Ser Pro Pro Gly Thr Lys Ser Leu Glu
1110                1115                1120                1125 ccg tgt acg tgt gga gcg gtc gac ctg tat ttg gtc acg cgg aac gct    3763
Pro Cys Thr Cys Gly Ala Val Asp Leu Tyr Leu Val Thr Arg Asn Ala
            1130                1135                1140 gat gtc atc ccg gct cga aga cgc ggg gac aag cgg gga gcg ctg ctc    3811
Asp Val Ile Pro Ala Arg Arg Arg Gly Asp Lys Arg Gly Ala Leu Leu
                1145                1150                1155 tcc cca aga ccc ctt tcg acc ttg aag ggg tcc tcg ggg gga cct gtg    3859
Ser Pro Arg Pro Leu Ser Thr Leu Lys Gly Ser Ser Gly Gly Pro Val
        1160                1165                1170 ctt tgc cct agg ggc cac gct gtc gga atc ttc cgg gca gct gtg tgc    3907
Leu Cys Pro Arg Gly His Ala Val Gly Ile Phe Arg Ala Ala Val Cys
    1175                1180                1185 tct cgg ggt gtg gct aag tcc ata gat ttc atc ccc gtt gag acg ctc    3955
Ser Arg Gly Val Ala Lys Ser Ile Asp Phe Ile Pro Val Glu Thr Leu
1190                1195                1200                1205 gac atc gtc acg cgg tct ccc acc ttt agt gac aac agc aca cca cca    4003
Asp Ile Val Thr Arg Ser Pro Thr Phe Ser Asp Asn Ser Thr Pro Pro
            1210                1215                1220
```

```
gct gtg ccc cag acc tat cag gtg ggg tac ttg cac gcc ccc act ggc      4051
Ala Val Pro Gln Thr Tyr Gln Val Gly Tyr Leu His Ala Pro Thr Gly
        1225                1230                1235 agt gga aaa agc acc aag gtc ccc gtc gcg tac gcc gcc cag ggg tat      4099
Ser Gly Lys Ser Thr Lys Val Pro Val Ala Tyr Ala Ala Gln Gly Tyr
    1240                1245                1250 aaa gtg ctg gtg ctc aat ccc tcg gtg gct gcc acc ctg gga ttt ggg      4147
Lys Val Leu Val Leu Asn Pro Ser Val Ala Ala Thr Leu Gly Phe Gly
1255                1260                1265 gcg tac ttg tcc aag gca cat ggc atc aac ccc aac att agg act gga      4195
Ala Tyr Leu Ser Lys Ala His Gly Ile Asn Pro Asn Ile Arg Thr Gly
1270                1275                1280                1285 gtc aga act gtg acg acc ggg gag ccc att aca tac tcc acg tat ggt      4243
Val Arg Thr Val Thr Thr Gly Glu Pro Ile Thr Tyr Ser Thr Tyr Gly
        1290                1295                1300 aaa ttc ctc gcc gat ggg ggc tgc gca ggc ggc gcc tat gac atc atc      4291
Lys Phe Leu Ala Asp Gly Gly Cys Ala Gly Gly Ala Tyr Asp Ile Ile
    1305                1310                1315 ata tgc gat gaa tgc cac tct gtg gat gct acc act att ctc ggc atc      4339
Ile Cys Asp Glu Cys His Ser Val Asp Ala Thr Thr Ile Leu Gly Ile
1320                1325                1330 ggg aca gtc ctt gac caa gca gag aca gcc ggg gtc agg cta act gta      4387
Gly Thr Val Leu Asp Gln Ala Glu Thr Ala Gly Val Arg Leu Thr Val
1335                1340                1345 ctg gcc acg gcc acg ccc ccc ggg tcg gtg aca acc ccc cat ccc aat      4435
Leu Ala Thr Ala Thr Pro Pro Gly Ser Val Thr Thr Pro His Pro Asn
1350                1355                1360                1365 ata gag gag gta gcc ctc gga cag gag ggt gag atc ccc ttc tat ggg      4483
Ile Glu Glu Val Ala Leu Gly Gln Glu Gly Glu Ile Pro Phe Tyr Gly
        1370                1375                1380 agg gcg ttt ccc ctg tct tac atc aag gga ggg agg cac ttg att ttc      4531
Arg Ala Phe Pro Leu Ser Tyr Ile Lys Gly Gly Arg His Leu Ile Phe
    1385                1390                1395 tgc cac tca aag aaa aag tgt gac gag ctc gca acg gcc ctt cgg ggc      4579
Cys His Ser Lys Lys Lys Cys Asp Glu Leu Ala Thr Ala Leu Arg Gly
1400                1405                1410 atg ggc ttg aac gct gtg gca tat tac aga ggg ttg gac gtc tcc ata      4627
Met Gly Leu Asn Ala Val Ala Tyr Tyr Arg Gly Leu Asp Val Ser Ile
1415                1420                1425 ata cca act caa gga gat gtg gtg gtc gtt gcc acc gac gcc ctc atg      4675
Ile Pro Thr Gln Gly Asp Val Val Val Val Ala Thr Asp Ala Leu Met
1430                1435                1440                1445 acg ggg tat act gga gac ttt gac tcc gtg atc gac tgc aac gta gcg      4723
Thr Gly Tyr Thr Gly Asp Phe Asp Ser Val Ile Asp Cys Asn Val Ala
        1450                1455                1460 gtc acc cag gcc gta gac ttc agc ctg gac ccc acc ttc act ata acc      4771
Val Thr Gln Ala Val Asp Phe Ser Leu Asp Pro Thr Phe Thr Ile Thr
    1465                1470                1475 aca cag act gtc ccg caa gac gct gtc tca cgt agt cag cgc cga ggg      4819
Thr Gln Thr Val Pro Gln Asp Ala Val Ser Arg Ser Gln Arg Arg Gly
1480                1485                1490 cgc acg ggt aga gga aga ctg ggc att tat agg tat gtt tcc act ggt      4867
Arg Thr Gly Arg Gly Arg Leu Gly Ile Tyr Arg Tyr Val Ser Thr Gly
1495                1500                1505 gag cga gcc tca gga atg ttt gac agt gta gta ctc tgt gag tgc tac      4915
Glu Arg Ala Ser Gly Met Phe Asp Ser Val Val Leu Cys Glu Cys Tyr
1510                1515                1520                1525 gac gca gga gct gct tgg tat gag ctc tca cca gtg gag acg acc gtc      4963
Asp Ala Gly Ala Ala Trp Tyr Glu Leu Ser Pro Val Glu Thr Thr Val
        1530                1535                1540
```

```
agg ctc agg gcg tat ttc aac acg cct ggc ttg cct gtg tgc cag gac    5011
Arg Leu Arg Ala Tyr Phe Asn Thr Pro Gly Leu Pro Val Cys Gln Asp
        1545                1550                1555 cac ctt gag ttt tgg gag gca gtt ttc acc ggc ctc aca cac ata gac    5059
His Leu Glu Phe Trp Glu Ala Val Phe Thr Gly Leu Thr His Ile Asp
        1560                1565                1570 gct cat ttc ctt tcc cag aca aag cag tcg ggg gaa aat ttc gca tac    5107
Ala His Phe Leu Ser Gln Thr Lys Gln Ser Gly Glu Asn Phe Ala Tyr
        1575                1580                1585 tta gta gcc tat cag gcc aca gtg tgc gcc agg gcc aaa gcg ccc ccc    5155
Leu Val Ala Tyr Gln Ala Thr Val Cys Ala Arg Ala Lys Ala Pro Pro
1590                1595                1600                1605 ccg tcc tgg gac gtc atg tgg aag tgc ttg act cga ctc aag ccc acg    5203
Pro Ser Trp Asp Val Met Trp Lys Cys Leu Thr Arg Leu Lys Pro Thr
            1610                1615                1620 ctt gtg ggc cct aca cct ctc ctg tac cgt ttg ggc tct gtt acc aac    5251
Leu Val Gly Pro Thr Pro Leu Leu Tyr Arg Leu Gly Ser Val Thr Asn
            1625                1630                1635 gag gtc acc ctt aca cac ccc gtg aca aaa tac atc gcc aca tgc atg    5299
Glu Val Thr Leu Thr His Pro Val Thr Lys Tyr Ile Ala Thr Cys Met
        1640                1645                1650 caa gct gac ctc gag gtc atg acc agc acg tgg gtc ctg gct ggg gga    5347
Gln Ala Asp Leu Glu Val Met Thr Ser Thr Trp Val Leu Ala Gly Gly
        1655                1660                1665 gtc tta gca gcc gtc gcc gcg tat tgc tta gcg acc ggg tgt gtt tcc    5395
Val Leu Ala Ala Val Ala Ala Tyr Cys Leu Ala Thr Gly Cys Val Ser
1670                1675                1680                1685 atc att ggc cgt tta cac atc aac cag cga gct gtc gtc gct ccg gac    5443
Ile Ile Gly Arg Leu His Ile Asn Gln Arg Ala Val Val Ala Pro Asp
            1690                1695                1700 aag gag gtc ctc tat gag gct ttt gat gag atg gag gaa tgt gcc tcc    5491
Lys Glu Val Leu Tyr Glu Ala Phe Asp Glu Met Glu Glu Cys Ala Ser
            1705                1710                1715 aga gcg gct ctc ctt gaa gag ggg cag cgg ata gcc gag atg ctg aag    5539
Arg Ala Ala Leu Leu Glu Glu Gly Gln Arg Ile Ala Glu Met Leu Lys
        1720                1725                1730 tcc aag atc caa ggc tta ttg cag caa gcc tct aaa cag gcc cag gac    5587
Ser Lys Ile Gln Gly Leu Leu Gln Gln Ala Ser Lys Gln Ala Gln Asp
        1735                1740                1745 ata caa ccc gct gtg caa gct tcg tgg ccc aag atg gag caa ttc tgg    5635
Ile Gln Pro Ala Val Gln Ala Ser Trp Pro Lys Met Glu Gln Phe Trp
1750                1755                1760                1765 gcc aaa cat atg tgg aac ttc ata agc ggc att cag tac ctc gca gga    5683
Ala Lys His Met Trp Asn Phe Ile Ser Gly Ile Gln Tyr Leu Ala Gly
            1770                1775                1780 ctg tca aca ctg cca ggg aac cct gct gtg gct tcc atg atg gca ttc    5731
Leu Ser Thr Leu Pro Gly Asn Pro Ala Val Ala Ser Met Met Ala Phe
            1785                1790                1795 agc gcc gcc ctc acc agt ccg ttg tca act agc acc acc atc ctt ctt    5779
Ser Ala Ala Leu Thr Ser Pro Leu Ser Thr Ser Thr Thr Ile Leu Leu
        1800                1805                1810 aac att ctg ggg ggc tgg ctg gcg tcc caa att gcg cca ccc gcg ggg    5827
Asn Ile Leu Gly Gly Trp Leu Ala Ser Gln Ile Ala Pro Pro Ala Gly
        1815                1820                1825 gcc act ggc ttt gtt gtc agt ggc ctg gtg gga gct gct gtt ggc agc    5875
Ala Thr Gly Phe Val Val Ser Gly Leu Val Gly Ala Ala Val Gly Ser
1830                1835                1840                1845 ata ggc ttg ggt aaa gtg ctg gtg gac atc ctg gca ggg tat ggt gcg    5923
Ile Gly Leu Gly Lys Val Leu Val Asp Ile Leu Ala Gly Tyr Gly Ala
            1850                1855                1860
```

```
ggc att tcg ggg gcc ctc gtc gcg ttt aag atc atg tct ggc gag aag    5971
Gly Ile Ser Gly Ala Leu Val Ala Phe Lys Ile Met Ser Gly Glu Lys
        1865                1870                1875 ccc tcc atg gag gat gtc atc aac ttg ctg cct ggg att ctg tct cca    6019
Pro Ser Met Glu Asp Val Ile Asn Leu Leu Pro Gly Ile Leu Ser Pro
    1880                1885                1890 ggt gct ctg gtg gtg gga gtc atc tgc gcg gcc att ctg cgc cgc cat    6067
Gly Ala Leu Val Val Gly Val Ile Cys Ala Ala Ile Leu Arg Arg His
1895                1900                1905 gtg gga ccg ggg gaa ggc gcg gtc caa tgg atg aac agg ctt atc gcc    6115
Val Gly Pro Gly Glu Gly Ala Val Gln Trp Met Asn Arg Leu Ile Ala
1910                1915                1920                1925 ttc gct tcc aga gga aac cac gtc gcc cct act cac tac gtg acg gag    6163
Phe Ala Ser Arg Gly Asn His Val Ala Pro Thr His Tyr Val Thr Glu
        1930                1935                1940 tcg gat gcg tcg cag cgt gtc acc caa ctg ctt ggc tct ctc act ata    6211
Ser Asp Ala Ser Gln Arg Val Thr Gln Leu Leu Gly Ser Leu Thr Ile
            1945                1950                1955 act agt cta ctc agg aga ctt cac aac tgg atc act gag gat tgc ccc    6259
Thr Ser Leu Leu Arg Arg Leu His Asn Trp Ile Thr Glu Asp Cys Pro
        1960                1965                1970 atc cca tgc gcc ggc tcg tgg ctc cgc gat gtg tgg gac tgg gtc tgt    6307
Ile Pro Cys Ala Gly Ser Trp Leu Arg Asp Val Trp Asp Trp Val Cys
    1975                1980                1985 acc atc cta aca gac ttt aag aac tgg ctg acc tcc aag ctg ttc cca    6355
Thr Ile Leu Thr Asp Phe Lys Asn Trp Leu Thr Ser Lys Leu Phe Pro
1990                1995                2000                2005 aag atg cct ggc ctc ccc ttt atc tct tgc caa aag ggg tac aag ggc    6403
Lys Met Pro Gly Leu Pro Phe Ile Ser Cys Gln Lys Gly Tyr Lys Gly
        2010                2015                2020 gtg tgg gcc ggc act ggc atc atg acc aca cga tgc ccc tgc ggc gcc    6451
Val Trp Ala Gly Thr Gly Ile Met Thr Thr Arg Cys Pro Cys Gly Ala
            2025                2030                2035 aac atc tct ggc aac gtc cgc ttg ggc tct atg aga atc aca gga ccc    6499
Asn Ile Ser Gly Asn Val Arg Leu Gly Ser Met Arg Ile Thr Gly Pro
        2040                2045                2050 aaa acc tgc atg aac acc tgg cag ggg acc ttt cct atc aat tgt tat    6547
Lys Thr Cys Met Asn Thr Trp Gln Gly Thr Phe Pro Ile Asn Cys Tyr
    2055                2060                2065 aca gaa ggc cag tgc ttg ccg aaa ccc gcg tta aac ttc aag acc gcc    6595
Thr Glu Gly Gln Cys Leu Pro Lys Pro Ala Leu Asn Phe Lys Thr Ala
2070                2075                2080                2085 atc tgg aga gtg gcg gcc tca gag tac gcg gaa gtg acg cag cac gga    6643
Ile Trp Arg Val Ala Ala Ser Glu Tyr Ala Glu Val Thr Gln His Gly
        2090                2095                2100 tca tat gcc tat ata aca ggg ctg acc act gac aac tta aaa gtc cct    6691
Ser Tyr Ala Tyr Ile Thr Gly Leu Thr Thr Asp Asn Leu Lys Val Pro
            2105                2110                2115 tgc caa ctc ccc tct cca gag ttt ttc tct tgg gtg gac gga gta caa    6739
Cys Gln Leu Pro Ser Pro Glu Phe Phe Ser Trp Val Asp Gly Val Gln
        2120                2125                2130 atc cat agg tcc gcc ccc aca cca aag ccg ttt ttc cgg gat gag gtc    6787
Ile His Arg Ser Ala Pro Thr Pro Lys Pro Phe Phe Arg Asp Glu Val
    2135                2140                2145 tcg ttc agc gtt ggg ctc aat tca ttt gtc gtc ggg tct cag ctt ccc    6835
Ser Phe Ser Val Gly Leu Asn Ser Phe Val Val Gly Ser Gln Leu Pro
2150                2155                2160                2165 tgt gac cct gag ccc gac act gag gta gtg atg tcc atg cta aca gac    6883
Cys Asp Pro Glu Pro Asp Thr Glu Val Val Met Ser Met Leu Thr Asp
        2170                2175                2180
```

```
cca tcc cat atc acg gcg gag gct gca gcg cgg cgt tta gcg cgg ggg    6931
Pro Ser His Ile Thr Ala Glu Ala Ala Ala Arg Arg Leu Ala Arg Gly
            2185                2190                2195 tca ccc cca tct gag gca agc tcc tca gcg agc cag ctg tcg gcg cca    6979
Ser Pro Pro Ser Glu Ala Ser Ser Ser Ala Ser Gln Leu Ser Ala Pro
        2200                2205                2210 tcg ctg cga gcc acc tgc acc acc cac ggt agg acc tat gat gtg gac    7027
Ser Leu Arg Ala Thr Cys Thr Thr His Gly Arg Thr Tyr Asp Val Asp
    2215                2220                2225 atg gtg gat gcc aac ctg ttc atg ggg ggc ggc gtg att cgg ata gag    7075
Met Val Asp Ala Asn Leu Phe Met Gly Gly Gly Val Ile Arg Ile Glu
2230                2235                2240                2245 tct gag tcc aaa gtg gtc gtt ctg gac tcc ctc gac tca atg acc gag    7123
Ser Glu Ser Lys Val Val Val Leu Asp Ser Leu Asp Ser Met Thr Glu
            2250                2255                2260 gaa gag ggc gac ctt gag cct tca gta cca tcg gag tat atg ctc ccc    7171
Glu Glu Gly Asp Leu Glu Pro Ser Val Pro Ser Glu Tyr Met Leu Pro
        2265                2270                2275 agg aag agg ttc cca ccg gcc tta ccg gct tgg gcg cgg cct gat tac    7219
Arg Lys Arg Phe Pro Pro Ala Leu Pro Ala Trp Ala Arg Pro Asp Tyr
    2280                2285                2290 aac cca ccg ctt gtg gaa tcg tgg aag agg cca gat tac caa cca ccc    7267
Asn Pro Pro Leu Val Glu Ser Trp Lys Arg Pro Asp Tyr Gln Pro Pro
2295                2300                2305 act gtt gcg ggc tgt gct ctc ccc ccc ccc aaa aag acc ccg acg cct    7315
Thr Val Ala Gly Cys Ala Leu Pro Pro Pro Lys Lys Thr Pro Thr Pro
2310                2315                2320                2325 cct cca agg aga cgc cgg aca gtg ggt ctg agc gag agc acc ata gga    7363
Pro Pro Arg Arg Arg Arg Thr Val Gly Leu Ser Glu Ser Thr Ile Gly
        2330                2335                2340 gat gcc ctc caa cag ctg gcc atc aag tcc ttt ggc cag ccc ccc cca    7411
Asp Ala Leu Gln Gln Leu Ala Ile Lys Ser Phe Gly Gln Pro Pro Pro
    2345                2350                2355 agc ggc gat tca ggc ctt tcc acg ggg gcg gac gcc gcc gac tcc ggc    7459
Ser Gly Asp Ser Gly Leu Ser Thr Gly Ala Asp Ala Ala Asp Ser Gly
2360                2365                2370 gat cgg aca ccc cct gac gag ttg gct ctt tcg gag aca ggt tct acc    7507
Asp Arg Thr Pro Pro Asp Glu Leu Ala Leu Ser Glu Thr Gly Ser Thr
2375                2380                2385 tcc tcc atg ccc ccc ctc gag ggg gag cct ggg gac cca gac ctg gag    7555
Ser Ser Met Pro Pro Leu Glu Gly Glu Pro Gly Asp Pro Asp Leu Glu
2390                2395                2400                2405 cct gag cag gta gag ctt caa cct cct ccc cag ggg ggg gag gca gct    7603
Pro Glu Gln Val Glu Leu Gln Pro Pro Pro Gln Gly Gly Glu Ala Ala
            2410                2415                2420 ccc ggc tcg gac tcg ggg tcc tgg tct act tgc tcc gag gag gat gac    7651
Pro Gly Ser Asp Ser Gly Ser Trp Ser Thr Cys Ser Glu Glu Asp Asp
        2425                2430                2435 tcc gtc gtg tgc tgc tcc atg tca tat tcc tgg acc ggg gct cta ata    7699
Ser Val Val Cys Cys Ser Met Ser Tyr Ser Trp Thr Gly Ala Leu Ile
    2440                2445                2450 act cct tgt agc ccc gaa gag gaa aag ttg cca att aac tcc ttg agc    7747
Thr Pro Cys Ser Pro Glu Glu Glu Lys Leu Pro Ile Asn Ser Leu Ser
2455                2460                2465 aac tcg ctg ttg cga tac cat aac aag gta tac tgt act aca tca aag    7795
Asn Ser Leu Leu Arg Tyr His Asn Lys Val Tyr Cys Thr Thr Ser Lys
2470                2475                2480                2485 agt gcc tca cta agg gct aaa aag gta act ttt gat agg atg caa gtg    7843
Ser Ala Ser Leu Arg Ala Lys Lys Val Thr Phe Asp Arg Met Gln Val
            2490                2495                2500
```

```
ctc gac gcc tat tat gat tca gtc tta aag gac atc aag cta gcg gcc    7891
Leu Asp Ala Tyr Tyr Asp Ser Val Leu Lys Asp Ile Lys Leu Ala Ala
            2505                2510                2515 tcc aag gtc agc gca agg ctc ctc acc tta gag gag gcg tgc caa ttg    7939
Ser Lys Val Ser Ala Arg Leu Leu Thr Leu Glu Glu Ala Cys Gln Leu
        2520                2525                2530 acc cca ccc cac tct gca aga tcc aag tat ggg ttt ggg gct aag gag    7987
Thr Pro Pro His Ser Ala Arg Ser Lys Tyr Gly Phe Gly Ala Lys Glu
    2535                2540                2545 gtc cgc agc ttg tcc ggg agg gcc gtc aac cac atc aag tcc gtg tgg    8035
Val Arg Ser Leu Ser Gly Arg Ala Val Asn His Ile Lys Ser Val Trp
2550                2555                2560                2565 aag gac ctc ttg gaa gac tca caa aca cca att cct aca acc atc atg    8083
Lys Asp Leu Leu Glu Asp Ser Gln Thr Pro Ile Pro Thr Thr Ile Met
            2570                2575                2580 gcc aaa aat gag gtg ttc tgc gtg gac ccc gcc aag ggg ggt aaa aaa    8131
Ala Lys Asn Glu Val Phe Cys Val Asp Pro Ala Lys Gly Gly Lys Lys
        2585                2590                2595 cca gct cgc ctt atc gtt tac cct gac ctc ggc gtc agg gtc tgc gag    8179
Pro Ala Arg Leu Ile Val Tyr Pro Asp Leu Gly Val Arg Val Cys Glu
    2600                2605                2610 aag atg gcc ctt tat gat gtc aca caa aag ctt cct cag gcg gtg atg    8227
Lys Met Ala Leu Tyr Asp Val Thr Gln Lys Leu Pro Gln Ala Val Met
    2615                2620                2625 ggg gct tct tat ggc ttc cag tac tcc ccc gct cag cgg gtg gag ttt    8275
Gly Ala Ser Tyr Gly Phe Gln Tyr Ser Pro Ala Gln Arg Val Glu Phe
2630                2635                2640                2645 ctc ttg aag gca tgg gcg gaa aag aga gac cct atg ggt ttt tcg tat    8323
Leu Leu Lys Ala Trp Ala Glu Lys Arg Asp Pro Met Gly Phe Ser Tyr
            2650                2655                2660 gat acc cga tgc ttt gac tca acc gtc act gag aga gac atc agg act    8371
Asp Thr Arg Cys Phe Asp Ser Thr Val Thr Glu Arg Asp Ile Arg Thr
        2665                2670                2675 gag gag tcc ata tac cag gcc tgc tcc tta ccc gag gag gcc cga act    8419
Glu Glu Ser Ile Tyr Gln Ala Cys Ser Leu Pro Glu Glu Ala Arg Thr
    2680                2685                2690 gcc ata cac tcg ctg act gag aga ctc tat gtg gga ggg ccc atg ttc    8467
Ala Ile His Ser Leu Thr Glu Arg Leu Tyr Val Gly Gly Pro Met Phe
    2695                2700                2705 aac agc aag ggc cag tcc tgc ggg tac agg cgt tgc cgc gcc agc ggg    8515
Asn Ser Lys Gly Gln Ser Cys Gly Tyr Arg Arg Cys Arg Ala Ser Gly
2710                2715                2720                2725 gtg ctt acc act agt atg ggg aac acc atc aca tgc tat gta aaa gcc    8563
Val Leu Thr Thr Ser Met Gly Asn Thr Ile Thr Cys Tyr Val Lys Ala
            2730                2735                2740 cta gcg gct tgc aag gct gcg ggg ata att gcg ccc acg atg ctg gta    8611
Leu Ala Ala Cys Lys Ala Ala Gly Ile Ile Ala Pro Thr Met Leu Val
        2745                2750                2755 tgc ggc gac gac ttg gtc gtc atc tca gaa agc cag ggg act gag gag    8659
Cys Gly Asp Asp Leu Val Val Ile Ser Glu Ser Gln Gly Thr Glu Glu
    2760                2765                2770 gac gag cgg aac ctg aga gcc ttc acg gag gct atg acc agg tat tct    8707
Asp Glu Arg Asn Leu Arg Ala Phe Thr Glu Ala Met Thr Arg Tyr Ser
    2775                2780                2785 gcc cct cct ggt gac ccc ccc aga ccg gaa tat gac ctg gag cta ata    8755
Ala Pro Pro Gly Asp Pro Pro Arg Pro Glu Tyr Asp Leu Glu Leu Ile
2790                2795                2800                2805 aca tct tgt tcc tca aac gtg tct gtg gca ctt ggc cca cag ggc cgc    8803
Thr Ser Cys Ser Ser Asn Val Ser Val Ala Leu Gly Pro Gln Gly Arg
            2810                2815                2820
```

```
cgc aga tac tac ctg acc aga gac ccc acc act tca att gcc cgg gct        8851
Arg Arg Tyr Tyr Leu Thr Arg Asp Pro Thr Thr Ser Ile Ala Arg Ala
        2825                2830                2835 gcc tgg gaa aca gtt aga cac tcc cct gtc aat tca tgg ctg gga aac        8899
Ala Trp Glu Thr Val Arg His Ser Pro Val Asn Ser Trp Leu Gly Asn
    2840                2845                2850 atc atc cag tac gct cca acc ata tgg gtt cgc atg gtc ctg atg aca        8947
Ile Ile Gln Tyr Ala Pro Thr Ile Trp Val Arg Met Val Leu Met Thr
2855                2860                2865 cac ttc ttc tcc att ctc atg gcc cag gac acc cta gac cag aac ctt        8995
His Phe Phe Ser Ile Leu Met Ala Gln Asp Thr Leu Asp Gln Asn Leu
2870                2875                2880                2885 aac ttt gaa atg tac gga tcg gtg tac tcc gtg agt cct ctg gac ctc        9043
Asn Phe Glu Met Tyr Gly Ser Val Tyr Ser Val Ser Pro Leu Asp Leu
        2890                2895                2900 cca gcc ata att gaa agg tta cac ggg ctt gac gcc ttc tct ctg cac        9091
Pro Ala Ile Ile Glu Arg Leu His Gly Leu Asp Ala Phe Ser Leu His
    2905                2910                2915 aca tac act ccc cac gaa ctg acg cgg gtg gct tca gcc ctc aga aaa        9139
Thr Tyr Thr Pro His Glu Leu Thr Arg Val Ala Ser Ala Leu Arg Lys
        2920                2925                2930 ctt ggg gcg cca ccc ctc aga gcg tgg aag agt cgg gcg cgt gca gtt        9187
Leu Gly Ala Pro Pro Leu Arg Ala Trp Lys Ser Arg Ala Arg Ala Val
    2935                2940                2945 agg gcg tcc ctc atc tcc cgt ggg ggg agg gcg gcc gtt tgc ggt cgg        9235
Arg Ala Ser Leu Ile Ser Arg Gly Gly Arg Ala Ala Val Cys Gly Arg
2950                2955                2960                2965 tac ctc ttc aac tgg gcg gtg aag acc aag ctc aaa ctc act cct ttg        9283
Tyr Leu Phe Asn Trp Ala Val Lys Thr Lys Leu Lys Leu Thr Pro Leu
        2970                2975                2980 ccg gag gca cgc ctc ctg gat ttg tcc agt tgg ttt acc gtc ggc gcc        9331
Pro Glu Ala Arg Leu Leu Asp Leu Ser Ser Trp Phe Thr Val Gly Ala
    2985                2990                2995 ggc ggg ggc gac att tat cac agc gtg tcg cgt gcc cga ccc cgc cta        9379
Gly Gly Gly Asp Ile Tyr His Ser Val Ser Arg Ala Arg Pro Arg Leu
3000                3005                3010 tta ctc ctt agc cta ctc cta ctt tct gta ggg gta ggc ctc ttc cta        9427
Leu Leu Leu Ser Leu Leu Leu Leu Ser Val Gly Val Gly Leu Phe Leu
    3015                3020                3025 ctc ccc gct cga tag agcggcacac attagctaca ctccatagct aactgttcct        9482
Leu Pro Ala Arg
3030 tttttttttt tttttttttt tttttttttt tttttttctt tttttttttt tttccctctt        9542 tcttcccttc tcatcttatt ctactttctt tcttggtggc tccatcttag ccctggtcac        9602 ggctagctgt gaaaggtccg tgagccgcat gactgcagag agtgccgtaa ctggtctctc        9662 tgcagatcat gt                                                            9674

<210> SEQ ID NO 6
<211> LENGTH: 3033
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

```
Thr Arg Lys Ala Ser Glu Arg Ser Gln Pro Arg Gly Arg Gln Pro
 50                  55                  60
Ile Pro Lys His Arg Arg Ser Thr Gly Lys Ser Trp Gly Lys Pro Gly
 65                  70                  75                  80
Tyr Pro Trp Pro Leu Tyr Gly Asn Glu Gly Leu Gly Trp Ala Gly Trp
                 85                  90                  95
Leu Leu Ser Pro Arg Gly Ser Arg Pro Ser Trp Gly Pro Asn Asp Pro
                100                 105                 110
Arg His Arg Ser Arg Asn Val Gly Lys Val Ile Asp Thr Leu Thr Cys
                115                 120                 125
Gly Phe Ala Asp Leu Leu Gly Tyr Val Pro Val Val Gly Ala Pro Leu
            130                 135                 140
Ser Gly Val Ala Ser Ala Leu Ala His Gly Val Arg Val Leu Glu Asp
145                 150                 155                 160
Gly Val Asn Phe Ala Thr Gly Asn Leu Pro Gly Cys Ser Phe Ser Ile
                165                 170                 175
Phe Leu Leu Ala Leu Leu Ser Cys Ile Thr Thr Pro Val Ser Ala Val
            180                 185                 190
Gln Val Lys Asn Thr Ser Asn Ala Tyr Met Ala Thr Asn Asp Cys Ser
            195                 200                 205
Asn Asp Ser Ile Thr Trp Gln Leu Glu Ala Ala Val Leu His Val Pro
210                 215                 220
Gly Cys Val Pro Cys Glu Lys Met Gly Asn Thr Ser Arg Cys Trp Ile
225                 230                 235                 240
Pro Val Ser Pro Asn Val Ala Val Arg Gln Pro Gly Ala Leu Thr Arg
                245                 250                 255
Gly Leu Arg Thr His Ile Asp Met Val Val Leu Ser Ala Thr Leu Cys
            260                 265                 270
Ser Ala Leu Tyr Val Gly Asp Leu Cys Gly Gly Val Met Leu Ala Ser
            275                 280                 285
Gln Met Phe Ile Val Ser Pro Gln His His Trp Phe Val Gln Glu Cys
290                 295                 300
Asn Cys Ser Ile Tyr Pro Gly Ala Ile Thr Gly His Arg Met Ala Trp
305                 310                 315                 320
Asp Met Met Met Asn Trp Ser Pro Thr Thr Thr Met Ile Leu Ala Tyr
                325                 330                 335
Val Met Arg Val Pro Glu Val Ile Ile Asp Ile Ile Ser Gly Ala His
                340                 345                 350
Trp Gly Val Met Phe Gly Leu Ala Tyr Phe Ser Met Gln Gly Ala Trp
            355                 360                 365
Ala Lys Val Val Val Ile Leu Leu Leu Ala Ser Gly Val Asp Ala Tyr
            370                 375                 380
Thr Thr Thr Thr Gly Ser Ala Ala Gly Arg Thr Thr Ser Ser Leu Ala
385                 390                 395                 400
Ser Ala Phe Ser Pro Gly Ala Arg Gln Asn Ile Gln Leu Ile Asn Thr
                405                 410                 415
Asn Gly Ser Trp His Ile Asn Arg Thr Ala Leu Asn Cys Asn Asp Ser
                420                 425                 430
Leu His Thr Gly Phe Phe Thr Ala Leu Phe Tyr Ile His Lys Phe Asn
            435                 440                 445
Ser Ser Gly Cys Pro Glu Arg Leu Ser Ala Cys Arg Asn Ile Glu Asp
450                 455                 460
Phe Arg Ile Gly Trp Gly Ala Leu Gln Tyr Asp Asp Asn Val Thr Asn
```

```
                    465                 470                 475                 480

Pro Glu Asp Met Arg Pro Tyr Cys Trp His Tyr Pro Pro Lys Gln Cys
                    485                 490                 495

Gly Val Val Pro Ala Gly Thr Val Cys Gly Pro Val Tyr Cys Phe Thr
                500                 505                 510

Pro Ser Pro Val Val Gly Thr Thr Asp Arg Leu Gly Val Pro Thr
            515                 520                 525

Tyr Thr Trp Gly Glu Asn Glu Thr Asp Val Phe Leu Leu Asn Ser Thr
            530                 535                 540

Arg Pro Pro Ser Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Thr Ser Thr Asp Leu Leu Cys Pro Thr Asp Cys Phe Arg Lys
                580                 585                 590

His Pro Glu Ala Thr Tyr Ile Lys Cys Gly Ser Gly Pro Trp Leu Thr
                595                 600                 605

Pro Lys Cys Leu Val Asp Tyr Pro Tyr Arg Leu Trp His Tyr Pro Cys
            610                 615                 620

Thr Val Asn Tyr Ser Thr Phe Lys Ile Arg Met Tyr Val Gly Gly Val
625                 630                 635                 640

Glu His Arg Leu Met Ala Ala Cys Asn Phe Thr Arg Gly Asp Arg Cys
                645                 650                 655

Asn Leu Glu Asp Arg Asp Arg Ser Gln Gln Thr Pro Leu Leu His Ser
                660                 665                 670

Thr Thr Glu Trp Ala Ile Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Met Tyr Gly Leu Ser Pro Ala Leu Thr Gln Tyr Ile Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Val Leu His Ala Ala Ser Ala Ala Ser Cys Asn Gly
            755                 760                 765

Phe Leu Tyr Phe Val Ile Phe Leu Val Ala Ala Trp His Ile Lys Gly
            770                 775                 780

Arg Val Val Pro Leu Ala Ala Tyr Ser Leu Thr Gly Leu Trp Pro Phe
785                 790                 795                 800

Cys Leu Leu Leu Leu Ala Leu Pro Gln Gln Ala Tyr Ala Tyr Asp Ala
                805                 810                 815

Ser Val His Gly Gln Val Gly Ala Ala Leu Leu Val Leu Ile Thr Leu
            820                 825                 830

Phe Thr Leu Thr Pro Gly Tyr Lys Thr Leu Leu Ser Gln Ser Leu Trp
            835                 840                 845

Trp Leu Cys Tyr Leu Leu Thr Leu Ala Glu Thr Met Val Gln Glu Trp
850                 855                 860

Ala Pro Ser Met Gln Ala Arg Gly Gly Arg Asp Gly Ile Ile Trp Ala
865                 870                 875                 880

Ala Thr Ile Phe Cys Pro Gly Val Val Phe Asp Ile Thr Lys Trp Leu
                885                 890                 895
```

```
                    -continued

Leu Ala Val Leu Gly Pro Gly Tyr Leu Leu Arg Gly Ala Leu Thr Arg
                900             905                 910

Val Pro Tyr Phe Val Arg Ala His Ala Leu Leu Arg Met Cys Thr Met
            915                 920                 925

Val Arg His Leu Ala Gly Gly Arg Tyr Val Gln Met Ala Leu Leu Ala
        930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
        995                 1000                1005

Arg Leu Gly Arg Glu Ile Leu Leu Gly Pro Ala Asp Gly Tyr Thr Ser
    1010                1015                1020

Lys Gly Trp Lys Leu Leu Ala Pro Ile Thr Ala Tyr Ala Gln Gln Thr
1025                1030                1035                1040

Arg Gly Leu Leu Gly Ser Ile Val Val Ser Met Thr Gly Arg Asp Lys
            1045                1050                1055

Thr Glu Gln Ala Gly Glu Val Gln Val Leu Ser Thr Val Thr Gln Ser
        1060                1065                1070

Phe Leu Gly Thr Ser Ile Ser Gly Val Leu Trp Thr Val Tyr His Gly
    1075                1080                1085

Ala Gly Asn Lys Thr Leu Ala Gly Ser Arg Gly Pro Val Thr Gln Met
    1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Thr Cys Gly Ala Val Asp Leu Tyr Leu
            1125                1130                1135

Val Thr Arg Asn Ala Asp Val Ile Pro Ala Arg Arg Arg Gly Asp Lys
        1140                1145                1150

Arg Gly Ala Leu Leu Ser Pro Arg Pro Leu Ser Thr Leu Lys Gly Ser
1155                1160                1165

Ser Gly Gly Pro Val Leu Cys Pro Arg Gly His Ala Val Gly Ile Phe
    1170                1175                1180

Arg Ala Ala Val Cys Ser Arg Gly Val Ala Lys Ser Ile Asp Phe Ile
1185                1190                1195                1200

Pro Val Glu Thr Leu Asp Ile Val Thr Arg Ser Pro Thr Phe Ser Asp
            1205                1210                1215

Asn Ser Thr Pro Pro Ala Val Pro Gln Thr Tyr Gln Val Gly Tyr Leu
        1220                1225                1230

His Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala Ala
    1250                1255                1260

Thr Leu Gly Phe Gly Ala Tyr Leu Ser Lys Ala His Gly Ile Asn Pro
1265                1270                1275                1280

Asn Ile Arg Thr Gly Val Arg Thr Val Thr Thr Gly Glu Pro Ile Thr
            1285                1290                1295

Tyr Ser Thr Tyr Gly Lys Phe Leu Ala Asp Gly Gly Cys Ala Gly Gly
        1300                1305                1310

Ala Tyr Asp Ile Ile Ile Cys Asp Glu Cys His Ser Val Asp Ala Thr
    1315                1320                1325
```

```
Thr Ile Leu Gly Ile Gly Thr Val Leu Asp Gln Ala Glu Thr Ala Gly
    1330                1335                1340

Val Arg Leu Thr Val Leu Ala Thr Ala Thr Pro Pro Gly Ser Val Thr
1345                1350                1355                1360

Thr Pro His Pro Asn Ile Glu Glu Val Ala Leu Gly Gln Glu Gly Glu
            1365                1370                1375

Ile Pro Phe Tyr Gly Arg Ala Phe Pro Leu Ser Tyr Ile Lys Gly Gly
        1380                1385                1390

Arg His Leu Ile Phe Cys His Ser Lys Lys Lys Cys Asp Glu Leu Ala
    1395                1400                1405

Thr Ala Leu Arg Gly Met Gly Leu Asn Ala Val Ala Tyr Tyr Arg Gly
    1410                1415                1420

Leu Asp Val Ser Ile Ile Pro Thr Gln Gly Asp Val Val Val Val Ala
1425                1430                1435                1440

Thr Asp Ala Leu Met Thr Gly Tyr Thr Gly Asp Phe Asp Ser Val Ile
            1445                1450                1455

Asp Cys Asn Val Ala Val Thr Gln Ala Val Asp Phe Ser Leu Asp Pro
        1460                1465                1470

Thr Phe Thr Ile Thr Thr Gln Thr Val Pro Gln Asp Ala Val Ser Arg
    1475                1480                1485

Ser Gln Arg Arg Gly Arg Thr Gly Arg Gly Arg Leu Gly Ile Tyr Arg
    1490                1495                1500

Tyr Val Ser Thr Gly Glu Arg Ala Ser Gly Met Phe Asp Ser Val Val
1505                1510                1515                1520

Leu Cys Glu Cys Tyr Asp Ala Gly Ala Ala Trp Tyr Glu Leu Ser Pro
            1525                1530                1535

Val Glu Thr Thr Val Arg Leu Arg Ala Tyr Phe Asn Thr Pro Gly Leu
        1540                1545                1550

Pro Val Cys Gln Asp His Leu Glu Phe Trp Glu Ala Val Phe Thr Gly
    1555                1560                1565

Leu Thr His Ile Asp Ala His Phe Leu Ser Gln Thr Lys Gln Ser Gly
    1570                1575                1580

Glu Asn Phe Ala Tyr Leu Val Ala Tyr Gln Ala Thr Val Cys Ala Arg
1585                1590                1595                1600

Ala Lys Ala Pro Pro Pro Ser Trp Asp Val Met Trp Lys Cys Leu Thr
            1605                1610                1615

Arg Leu Lys Pro Thr Leu Val Gly Pro Thr Pro Leu Leu Tyr Arg Leu
        1620                1625                1630

Gly Ser Val Thr Asn Glu Val Thr Leu Thr His Pro Val Thr Lys Tyr
    1635                1640                1645

Ile Ala Thr Cys Met Gln Ala Asp Leu Glu Val Met Thr Ser Thr Trp
    1650                1655                1660

Val Leu Ala Gly Gly Val Leu Ala Ala Val Ala Ala Tyr Cys Leu Ala
1665                1670                1675                1680

Thr Gly Cys Val Ser Ile Ile Gly Arg Leu His Ile Asn Gln Arg Ala
            1685                1690                1695

Val Val Ala Pro Asp Lys Glu Val Leu Tyr Glu Ala Phe Asp Glu Met
        1700                1705                1710

Glu Glu Cys Ala Ser Arg Ala Ala Leu Leu Glu Glu Gly Gln Arg Ile
    1715                1720                1725

Ala Glu Met Leu Lys Ser Lys Ile Gln Gly Leu Leu Gln Gln Ala Ser
    1730                1735                1740

Lys Gln Ala Gln Asp Ile Gln Pro Ala Val Gln Ala Ser Trp Pro Lys
```

-continued

```
            1745                1750                1755                1760
Met Glu Gln Phe Trp Ala Lys His Met Trp Asn Phe Ile Ser Gly Ile
                1765                1770                1775
Gln Tyr Leu Ala Gly Leu Ser Thr Leu Pro Gly Asn Pro Ala Val Ala
            1780                1785                1790
Ser Met Met Ala Phe Ser Ala Ala Leu Thr Ser Pro Leu Ser Thr Ser
        1795                1800                1805
Thr Thr Ile Leu Leu Asn Ile Leu Gly Gly Trp Leu Ala Ser Gln Ile
    1810                1815                1820
Ala Pro Pro Ala Gly Ala Thr Gly Phe Val Val Ser Gly Leu Val Gly
1825                1830                1835                1840
Ala Ala Val Gly Ser Ile Gly Leu Gly Lys Val Leu Val Asp Ile Leu
                1845                1850                1855
Ala Gly Tyr Gly Ala Gly Ile Ser Gly Ala Leu Val Ala Phe Lys Ile
            1860                1865                1870
Met Ser Gly Glu Lys Pro Ser Met Glu Asp Val Ile Asn Leu Leu Pro
        1875                1880                1885
Gly Ile Leu Ser Pro Gly Ala Leu Val Val Gly Val Ile Cys Ala Ala
    1890                1895                1900
Ile Leu Arg Arg His Val Gly Pro Gly Glu Gly Ala Val Gln Trp Met
1905                1910                1915                1920
Asn Arg Leu Ile Ala Phe Ala Ser Arg Gly Asn His Val Ala Pro Thr
                1925                1930                1935
His Tyr Val Thr Glu Ser Asp Ala Ser Gln Arg Val Thr Gln Leu Leu
            1940                1945                1950
Gly Ser Leu Thr Ile Thr Ser Leu Leu Arg Arg Leu His Asn Trp Ile
        1955                1960                1965
Thr Glu Asp Cys Pro Ile Pro Cys Ala Gly Ser Trp Leu Arg Asp Val
    1970                1975                1980
Trp Asp Trp Val Cys Thr Ile Leu Thr Asp Phe Lys Asn Trp Leu Thr
1985                1990                1995                2000
Ser Lys Leu Phe Pro Lys Met Pro Gly Leu Pro Phe Ile Ser Cys Gln
                2005                2010                2015
Lys Gly Tyr Lys Gly Val Trp Ala Gly Thr Gly Ile Met Thr Thr Arg
            2020                2025                2030
Cys Pro Cys Gly Ala Asn Ile Ser Gly Asn Val Arg Leu Gly Ser Met
        2035                2040                2045
Arg Ile Thr Gly Pro Lys Thr Cys Met Asn Thr Trp Gln Gly Thr Phe
    2050                2055                2060
Pro Ile Asn Cys Tyr Thr Glu Gly Gln Cys Leu Pro Lys Pro Ala Leu
2065                2070                2075                2080
Asn Phe Lys Thr Ala Ile Trp Arg Val Ala Ala Ser Glu Tyr Ala Glu
                2085                2090                2095
Val Thr Gln His Gly Ser Tyr Ala Tyr Ile Thr Gly Leu Thr Thr Asp
            2100                2105                2110
Asn Leu Lys Val Pro Cys Gln Leu Pro Ser Pro Glu Phe Phe Ser Trp
        2115                2120                2125
Val Asp Gly Val Gln Ile His Arg Ser Ala Pro Thr Pro Lys Pro Phe
    2130                2135                2140
Phe Arg Asp Glu Val Ser Phe Ser Val Gly Leu Asn Ser Phe Val Val
2145                2150                2155                2160
Gly Ser Gln Leu Pro Cys Asp Pro Glu Pro Asp Thr Glu Val Val Met
                2165                2170                2175
```

```
Ser Met Leu Thr Asp Pro Ser His Ile Thr Ala Glu Ala Ala Ala Arg
        2180                2185                2190

Arg Leu Ala Arg Gly Ser Pro Pro Ser Glu Ala Ser Ser Ser Ala Ser
        2195                2200                2205

Gln Leu Ser Ala Pro Ser Leu Arg Ala Thr Cys Thr Thr His Gly Arg
        2210                2215                2220

Thr Tyr Asp Val Asp Met Val Asp Ala Asn Leu Phe Met Gly Gly Gly
2225                2230                2235                2240

Val Ile Arg Ile Glu Ser Glu Ser Lys Val Val Leu Asp Ser Leu
                2245                2250                2255

Asp Ser Met Thr Glu Glu Glu Gly Asp Leu Glu Pro Ser Val Pro Ser
        2260                2265                2270

Glu Tyr Met Leu Pro Arg Lys Arg Phe Pro Pro Ala Leu Pro Ala Trp
        2275                2280                2285

Ala Arg Pro Asp Tyr Asn Pro Pro Leu Val Glu Ser Trp Lys Arg Pro
        2290                2295                2300

Asp Tyr Gln Pro Pro Thr Val Ala Gly Cys Ala Leu Pro Pro Pro Lys
2305                2310                2315                2320

Lys Thr Pro Thr Pro Pro Pro Arg Arg Arg Arg Thr Val Gly Leu Ser
                2325                2330                2335

Glu Ser Thr Ile Gly Asp Ala Leu Gln Gln Leu Ala Ile Lys Ser Phe
                2340                2345                2350

Gly Gln Pro Pro Pro Ser Gly Asp Ser Gly Leu Ser Thr Gly Ala Asp
                2355                2360                2365

Ala Ala Asp Ser Gly Asp Arg Thr Pro Pro Asp Glu Leu Ala Leu Ser
        2370                2375                2380

Glu Thr Gly Ser Thr Ser Ser Met Pro Pro Leu Glu Gly Glu Pro Gly
2385                2390                2395                2400

Asp Pro Asp Leu Glu Pro Glu Gln Val Glu Leu Gln Pro Pro Pro Gln
                2405                2410                2415

Gly Gly Glu Ala Ala Pro Gly Ser Asp Ser Gly Ser Trp Ser Thr Cys
                2420                2425                2430

Ser Glu Glu Asp Asp Ser Val Val Cys Cys Ser Met Ser Tyr Ser Trp
                2435                2440                2445

Thr Gly Ala Leu Ile Thr Pro Cys Ser Pro Glu Glu Glu Lys Leu Pro
        2450                2455                2460

Ile Asn Ser Leu Ser Asn Ser Leu Leu Arg Tyr His Asn Lys Val Tyr
2465                2470                2475                2480

Cys Thr Thr Ser Lys Ser Ala Ser Leu Arg Ala Lys Lys Val Thr Phe
                2485                2490                2495

Asp Arg Met Gln Val Leu Asp Ala Tyr Tyr Asp Ser Val Leu Lys Asp
                2500                2505                2510

Ile Lys Leu Ala Ala Ser Lys Val Ser Ala Arg Leu Leu Thr Leu Glu
        2515                2520                2525

Glu Ala Cys Gln Leu Thr Pro Pro His Ser Ala Arg Ser Lys Tyr Gly
        2530                2535                2540

Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Ser Gln Thr Pro Ile
                2565                2570                2575

Pro Thr Thr Ile Met Ala Lys Asn Glu Val Phe Cys Val Asp Pro Ala
        2580                2585                2590

Lys Gly Gly Lys Lys Pro Ala Arg Leu Ile Val Tyr Pro Asp Leu Gly
        2595                2600                2605
```

```
Val Arg Val Cys Glu Lys Met Ala Leu Tyr Asp Val Thr Gln Lys Leu
    2610                2615                2620

Pro Gln Ala Val Met Gly Ala Ser Tyr Gly Phe Gln Tyr Ser Pro Ala
2625                2630                2635                2640

Gln Arg Val Glu Phe Leu Leu Lys Ala Trp Ala Glu Lys Arg Asp Pro
    2645                2650                2655

Met Gly Phe Ser Tyr Asp Thr Arg Cys Phe Asp Ser Thr Val Thr Glu
        2660                2665                2670

Arg Asp Ile Arg Thr Glu Glu Ser Ile Tyr Gln Ala Cys Ser Leu Pro
    2675                2680                2685

Glu Glu Ala Arg Thr Ala Ile His Ser Leu Thr Glu Arg Leu Tyr Val
    2690                2695                2700

Gly Gly Pro Met Phe Asn Ser Lys Gly Gln Ser Cys Gly Tyr Arg Arg
2705                2710                2715                2720

Cys Arg Ala Ser Gly Val Leu Thr Thr Ser Met Gly Asn Thr Ile Thr
        2725                2730                2735

Cys Tyr Val Lys Ala Leu Ala Ala Cys Lys Ala Ala Gly Ile Ile Ala
        2740                2745                2750

Pro Thr Met Leu Val Cys Gly Asp Asp Leu Val Val Ile Ser Glu Ser
    2755                2760                2765

Gln Gly Thr Glu Glu Asp Glu Arg Asn Leu Arg Ala Phe Thr Glu Ala
    2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
        2805                2810                2815

Gly Pro Gln Gly Arg Arg Arg Tyr Tyr Leu Thr Arg Asp Pro Thr Thr
        2820                2825                2830

Ser Ile Ala Arg Ala Ala Trp Glu Thr Val Arg His Ser Pro Val Asn
    2835                2840                2845

Ser Trp Leu Gly Asn Ile Ile Gln Tyr Ala Pro Thr Ile Trp Val Arg
    2850                2855                2860

Met Val Leu Met Thr His Phe Phe Ser Ile Leu Met Ala Gln Asp Thr
2865                2870                2875                2880

Leu Asp Gln Asn Leu Asn Phe Glu Met Tyr Gly Ser Val Tyr Ser Val
        2885                2890                2895

Ser Pro Leu Asp Leu Pro Ala Ile Ile Glu Arg Leu His Gly Leu Asp
        2900                2905                2910

Ala Phe Ser Leu His Thr Tyr Thr Pro His Glu Leu Thr Arg Val Ala
    2915                2920                2925

Ser Ala Leu Arg Lys Leu Gly Ala Pro Pro Leu Arg Ala Trp Lys Ser
    2930                2935                2940

Arg Ala Arg Ala Val Arg Ala Ser Leu Ile Ser Arg Gly Gly Arg Ala
2945                2950                2955                2960

Ala Val Cys Gly Arg Tyr Leu Phe Asn Trp Ala Val Lys Thr Lys Leu
        2965                2970                2975

Lys Leu Thr Pro Leu Pro Glu Ala Arg Leu Leu Asp Leu Ser Ser Trp
        2980                2985                2990

Phe Thr Val Gly Ala Gly Gly Gly Asp Ile Tyr His Ser Val Ser Arg
        2995                3000                3005

Ala Arg Pro Arg Leu Leu Leu Leu Ser Leu Leu Leu Leu Ser Val Gly
    3010                3015                3020

Val Gly Leu Phe Leu Leu Pro Ala Arg
```

-continued

<210> SEQ ID NO 7
<211> LENGTH: 8024
<212> TYPE: RNA
<213> ORGANISM: Artificial Sequence
<220> FEATURE:
<223> OTHER INFORMATION: HCV-derived synthetically created replicon RNA rSGREP-JFH1/GND

<400> SEQUENCE: 7

| | | | | | |
|---|---|---|---|---|---|
| accugcccu | aauagggcg | acacuccgcc | augaaucacu | ccccugugag | gaacuacugu | 60 |
| cuucacgcag | aaagcgccua | gccauggcgu | uaguaugagu | gucguacagc | cuccaggccc | 120 |
| ccccucccg | ggagagccau | aguggucugc | ggaaccggug | aguacaccgg | aauugccggg | 180 |
| aagacugggu | ccuuucuugg | auaaacccac | ucuaugcccg | gccauuuggg | cgugcccccg | 240 |
| caagacugcu | agccgaguag | cguuggguug | cgaaaggccu | uggguacug | ccugauaggg | 300 |
| cgcuugcgag | ugccccggga | ggucucuag | accgugcacc | augagcacaa | auccuaaacc | 360 |
| ucaaagaaaa | accaaaagaa | acaccaaccg | ucgcccaaug | uugaacaag | auggauugca | 420 |
| cgcagguucu | ccggccgcuu | ggguggagag | gcuauucggc | uaugacuggg | cacaacagac | 480 |
| aaucggcugc | ucugaugccg | ccguguuccg | gcugucagcg | caggggcgcc | cgguucuuuu | 540 |
| ugucaagacc | gaccgucg | gugcccgaa | ugaacgcag | gacgaggcag | cgcggcuauc | 600 |
| guggcuggcc | acgacgggcg | uuccuugcgc | agcugugcuc | gacguuguca | cugaagcggg | 660 |
| aagggacugg | cugcuauugg | gcgaagugcc | ggggcaggau | cuccugucau | cucaccuugc | 720 |
| uccugccgag | aaaguaucca | ucauggcuga | ugcaaugcgg | cggcugcaua | cgcuugaucc | 780 |
| ggcuaccugc | ccauucgacc | accaagcgaa | acaucgcauc | gagcgagcac | guacucggau | 840 |
| ggaagccggu | cuugucgauc | aggaugaucu | ggacgaagag | caucaggggc | ucgcgccagc | 900 |
| cgaacuguuc | gccaggcuca | aggcgcgcau | gcccgacggc | gaggaucucg | ucgugaccca | 960 |
| uggcgaugcc | ugcuugccga | auaucauggu | ggaaaauggc | cgcuuuucug | gauucaucga | 1020 |
| cuguggccgg | cugggugugg | cggaccgcua | ucaggacaua | gcguuggcua | cccgugauau | 1080 |
| ugcugaagag | cuuggcggcg | aaugggcuga | ccgcuuccuc | gugcuuuacg | guaucgccgc | 1140 |
| ucccgauucg | cagcgcaucg | ccuucuaucg | ccuucuugac | gaguucuucu | gaguuuaaac | 1200 |
| ccucuccuc | ccccccccu | aacguuacug | gccgaagccg | cuuggaauaa | ggccggugug | 1260 |
| cguuugucua | uauguuauuu | uccaccauau | ugccgucuuu | uggcaaugug | agggcccgga | 1320 |
| aaccuggccc | ugucuucuug | acgagcauuc | cuaggggucu | uuccccucuc | gccaaaggaa | 1380 |
| ugcaaggucu | guugaaugguc | gugaaggaag | caguuccucu | ggaagcuucu | ugaagacaaa | 1440 |
| caacgucugu | agcgacccuu | ugcaggcagc | ggaaccccc | accuggcgac | aggugccucu | 1500 |
| gcggccaaaa | gccacgugua | uaagauacac | cugcaaaggc | ggcacaaccc | cagugccacg | 1560 |
| uugugaguug | gauaguugug | gaaagaguca | aauggcucuc | cucaagcgua | uucaacaagg | 1620 |
| ggcugaagga | ugcccagaag | guaccccau | uguagggauc | ugaucggggc | cucggugca | 1680 |
| caugcuuuac | auguguuuag | ucgagguuaa | aaaaacgucu | aggcccccg | aaccacgggg | 1740 |
| acguggguuu | ccuuugaaaa | acacgaugau | accauggcuc | ccaucacugc | uuaugcccag | 1800 |
| caaacacgag | gccuccuggg | cgccauagug | gugaguauga | cggggcguga | caggacgaaa | 1860 |
| caggccgggg | aaguccaaau | ccugccaca | gucucucagu | ccuuccucgg | aacaaccauc | 1920 |
| ucgggguuu | ugguggacugu | uuaccacgga | gcuggcaaca | agacucuagc | cggcuuacgg | 1980 |
| gguccgguca | cgcagaugua | cucgagugcu | gaggggggacu | ugguaggcug | gcccagcccc | 2040 |

```
ccugggacca agucuuugga gccgugcaag uguggagccg ucgaccuaua ucggucacg    2100
cggaacgcug augucauccc ggcucggaga cgcggggaca agcggggagc auugcuccc    2160
ccgagacccu uuucgaccuu gaaggggucc ucgggggggc cggugcucug cccuagggc    2220
cacgucguug ggcucuuccg agcagcugug ugcucucggg gcguggccaa auccaucgau   2280
uucauccccg uugagacacu cgacguuguu acaaggucuc ccacuuucag ugacaacagc   2340
acgccaccgg cugugcccca gaccuaucag gucggguacu ugcaugcucc aacuggcagu   2400
ggaaagagca ccaaggcccc ugucgcguau gccgcccagg gguacaaagu acuagugcuu   2460
aaccccucgg uagcugccac ccugggguuu ggggcguacc uauccaaggc acauggcauc   2520
aaucccaaca uuaggacugg agucaggacc gugaugaccg ggaggccau cacguacucc     2580
acauauggca aauuucucgc cgaugggggc ugcgcuagcg gcgccauga caucaucaua    2640
ugcgaugaau gccacgcugu ggaugcuacc uccauucucg gcaucggaac gguccuugau   2700
caagcagaga cagccggggu cagacuaacu gugcuggcua cggccacacc ccccgggucc   2760
gugacaaccc cccaucccga uauagaaaag guaggccucg gcgggaggg ugagauccccc    2820
uucuauggga gggcgauucc ccuauccugc aucaagggag ggagacaccu gauuuucugc   2880
cacucaaaga aaagguguga cgagcucgcg gcggcccuuc ggggcauggg cuugaaugcc   2940
guggcauacu auagagggu ggacgucucc auaauaccag cucagggaga guggugguc    3000
gucgccaccg acgcccucau gacggggguac acuggagacu ugacuccgu gaucgacugc   3060
aauguagcgg ucacccaagc ugucgacuuc agccuggacc ccaccuucac uauaaccaca   3120
cagacugucc cacaagacgc ugucucacgc agucagcgcc gcgggcgcac agguagagga   3180
agacagggca cuuauaggua guuuccacu ggugaacgag ccucaggaau guuugacagu    3240
guagugcuuu gugagugcua cgacgcaggg gcugcguggu acgaucucac accagcggag   3300
accaccguca ggcuuagagc guauuucaac acgcccggcc uacccgugug ucaagaccau   3360
cuugaauuuu gggaggcagu uuucaccggc cucacacaca uagacgccca cuuccucucc   3420
caaacaaagc aagcggggga gaacuucgcg uaccuaguag ccuaccaagc uacgguguge   3480
gccagagcca aggcccuccc cccguccugg gacgccaugu ggaagugccu ggcccgacuc   3540
aagccuacgc uugcgggccc cacaccucuc cuguaccguu ugggcccuau uaccaaugag   3600
gucacccuca cacacccugg gacgaaguac aucgccacau gcaugcaagc ugaccuugag   3660
gucaugacca gcacgugggu ccuagcugga ggaguccugg cagccgucgc cgcauauugc   3720
cuggcgacug gaugcguuuc caucaucggc cgcuugcacg ucaaccagcg agucgucguu   3780
gcgccggaua aggagguccu guaugaggcu uuugaugaga uggaggaaug cgccucuagg   3840
gcggcucuca ucgaagaggg gcagcggaua gccgagaugu ugaaguccaa gauccaaggc   3900
uugcugcagc aggccucuaa gcaggcccag gacauacaac ccgcuaugca ggcuucaugg   3960
cccaaagugg aacauuuug ggccagacac augguggaacu cauuagcgg cauccaauac    4020
cucgcaggau ugucaacacu gccagggaac cccgcggugg cuccaugau ggcauucagu   4080
gccgcccuca ccagucccguu gucgaccagu accaccaucu uucucaacau cauggagagac   4140
ugguuagcgu cccagaucgc accaccccgcg ggggccaccg gcuuugcgu caguggccug   4200
guggggcug ccguggcag cauaggccug gguaaggugc uguggacau ccggcagga     4260
uauggugcgg gcauuccggg gccccucguc gcauucaaga ucaugucugg cgagaagccc   4320
ucuauggaag augucaucaa ucuacugccu gggauccugu ccgggagc ccuggugug       4380
ggggucaucu gcgcggccau ucugcgccgc cacgugggac cggggagggg cgcgguccaa   4440
```

```
uggaugaaca ggcuuauugc cuuugcuucc agaggaaacc acgucgcccc uacucacuac    4500
gugacggagu cggaugcguc gcagcgugug acccaacuac uuggcucucu acuauaacc     4560 agccuacuca gaagacucca caauuggaua acugaggacu gccccauccc augcuccgga    4620
uccuggcucc gcgacgugug ggacuggguu ugcaccaucu gacagacuu caaaaauugg     4680 cugaccucua aauuguuccc caagcugccc ggccuccccu ucaucucuug ucaaaagggg    4740
uacaagggug ugugggccgg cacuggcauc augaccacgc gcugcccuug cggcgccaac    4800
aucucuggca auguccgccu gggcucuaug aggaucacag gccuaaaac cugcaugaac     4860 accuggcagg ggaccuuucc uaucaauugc uacacggagg ccagugcgc gccgaaaccc     4920 cccacgaacu acaagaccgc caucggagg guggcggccu cggaguacgc ggaggugacg    4980
cagcaugggu cguacuccua guaacagga cugaccacug acaaucugaa aauuccuugc     5040
caacuaccuu uccagaguu uuucccugg guggacggug ugcagaucca uagguuugca     5100
cccacaccaa agccguuuuu ccgggaugag gucucguucu gcguugggcu uaauuccuau    5160
gcugucgggu cccagcuucc cugugaaccu gagcccgacg cagacguauu gagguccaug    5220
cuaacagauc cgccccacau cacgcgcgag acugcggcgc ggcgcuuggc acggggauca    5280
ccuccaucug aggcgagcuc ucagugagc cagcuaucag caccgucgcu gcgggccacc     5340
ugcaccaccc acagcaacac cuaugacgug gacauggucg augccaaccu gcucauggag    5400
ggcggugugg cucagacaga gccugagucc aggugcccg uucuggacuu ucucgagcca    5460
auggccgagg aagagagcga ccuugagccc ucaauaccau cggagugcau gcuccccagg    5520
agcggguuuc cacgggccuu accggcuugg gcacggccug acuacaaccc gccgcucgug    5580
gaaucgugga ggaggccaga uuaccaaccg cccaccguug cugguugugc ucuccccccc    5640
cccaagaagg cccgacgcc uccccaagg agacgccgga caguggucu gagcgagagc      5700 accauaucag aagcccucca gcaacuggcc aucaagaccu uggccagcc ccccucgagc    5760 ggugaugcag gcucguccac gggggcgggc gccgccgaau ccggcggucc gacgucccu     5820 ggugagccgg cccccucaga gacagguucc gccuccucua ugcccccccu cgaggggag    5880 ccuggagauc cggaccugga gucugaucag guagagcuuc aaccucccc ccagggggg    5940 ggggguagcuc ccgguucggg cucggggucu uggucuacuu gcccgagga ggacgauacc   6000 accgugugcu gcuccaugu auacuccugg accggggcuc uaauaaccc cuguagcccc     6060 gaagaggaaa aguugccaau caacccuuug aguaacucgc uguugcgaua ccauaacaag    6120
guguacugua caacaucaaa gagcgccuca cagagggcua aaaagguaac uuuugacagg    6180
acgcaagugc ucgacgccca uuaugacuca gucuuaaagg acaucaagcu agcggcuucc    6240
aaggucagcg caaggcuccu caccuuggag gaggcgugcc aguugacucc accccauucu    6300
gcaagaucca aguauggauu cggggccaag gagguccgca gcuugccgg gagggccguu    6360 aaccacauca agccggugug gaagagaccc cuggaagacc cacaaacacc aauucccaca    6420
accaucaugg ccaaaaauga ggguuucugc guggaccccg ccaagggggg uaagaaacca    6480
gcucgccuca ucguuuaccc ugaccucggc guccggggucu gcgagaaaau ggcccucuau    6540
gacauuacac aaaagcuucc ucaggcggua auggagcuu ccauaggcuu ccaguacucc    6600
ccugcccaac ggguggagua ucucuugaaa gcaugggcgg aaaagaagga ccccaugggu    6660
uuuucguaug auacccgaug cuucgacuca accgucacug agagacau caggaccgag     6720 gaguccauau accaggccug cucccugccc gaggaggccc gcacugccau acacucgcug    6780
acugagagac uuuacguagg aggccccaug uucaacagca agggucaaac cugcggguuac   6840
```

| | | | | |
|---|---|---|---|---|
| agacguugcc | gcgccagcgg | ggugcuaacc | acuagcaugg | guaacaccau cacaugcuau | 6900 |
| gugaaagccc | uagcggccug | caaggcugcg | gggauaguug | cgcccacaau gcugguaugc | 6960 |
| ggcaaugacc | uaguagucau | cucagaaagc | caggggacug | aggaggacga gcggaaccug | 7020 |
| agagccuuca | cggaggccau | gaccagguac | ucugccccuc | cuggugaucc ccccagaccg | 7080 |
| gaauaugacc | uggagcuaau | aacauccugu | uccucaaaug | ugucuggggc guugggcccg | 7140 |
| cggggccgcc | gcagauacua | ccugaccaga | gacccaacca | uccacucgc ccgggcugcc | 7200 |
| ugggaaacag | uuagacacuc | cccuaucaau | ucauggcugg | gaaacaucau ccaguaugcu | 7260 |
| ccaaccauau | ggguucgcau | gguccuaaug | acacacuucu | ucccauucu cauggccaa | 7320 |
| gacacccugg | accagaaccu | caacuuugag | auguauggau | caguauacuc cgugaauccu | 7380 |
| uuggaccuuc | cagccauaau | ugagagguua | cacgggcuug | acgccuuuuc uaugcacaca | 7440 |
| uacucucacc | acgaacugac | gcggguggcu | ucagcccuca | gaaaacuugg ggcgccaccc | 7500 |
| cucagggugu | ggaagagucg | ggcucgcgca | gucaggggcgu | cccucaucuc ccguggaggg | 7560 |
| aaagcggccg | uugcggccg | auaucucuuc | aauugggcgg | ugaagaccaa gcucaaacuc | 7620 |
| acccauugc | cggaggcgcg | ccuacuggac | uuauccaguu | gguuccacgu cggcgccggc | 7680 |
| gggggcgaca | uuuuucacag | cgugucgcgc | gcccgacccc | gcucauuacu cuucggccua | 7740 |
| cuccuacuuu | ucguaggggu | aggcucuuc | cuacucccg | cucgguagag cggcacacac | 7800 |
| uagguacacu | ccauagcuaa | cuguuccuuu | uuuuuuuuu | uuuuuuuuu uuuuuuuuu | 7860 |
| uuuuuuuuu | cuuuuuuuu | uuuuucccuc | uuucuucccu | ucaucuua uucuacuuc | 7920 |
| uuucuugguog | gcuccaucuu | agcccuaguc | acggcuagcu | ugaaaagguc cgugagccgc | 7980 |
| augacugcag | agagugccgu | aacuggucuc | ucugcagauc | augu | 8024 |

<210> SEQ ID NO 8
<211> LENGTH: 7994
<212> TYPE: RNA
<213> ORGANISM: Artificial Sequence
<220> FEATURE:
<223> OTHER INFORMATION: HCV-derived synthetically created replicon RNA
      rSGREP-JFH1/dGDD

<400> SEQUENCE: 8

| | | | | |
|---|---|---|---|---|
| accugcccu | aauagggcg | acacuccgcc | augaaucacu | ccccugugag gaacuacugu | 60 |
| cuucacgcag | aaagcgccua | gccauggcgu | uaguaugagu | gucguacagc cuccaggccc | 120 |
| cccccucccg | ggagagccau | aguggucugc | ggaaccggug | aguacaccgg aauugccggg | 180 |
| aagacugggu | ccuuucuugg | auaaacccac | ucuaugcccg | gccauuuggg cgugccccg | 240 |
| caagacugcu | agccgaguag | cguuggguug | cgaaaggccu | ugugguacug ccugauaggg | 300 |
| cgcuugcgag | ugccccggga | ggucucguag | accgugcacc | augagcacaa auccuaaacc | 360 |
| ucaaagaaaa | accaaaagaa | acaccaaccg | ucgcccaaug | auugaacaag auggauugca | 420 |
| cgcagguucu | ccggccgcuu | ggguggagag | gcuauucggc | uaugacuggg cacaacagac | 480 |
| aaucggcugc | ucugaugccg | ccguguuccg | gcugucagcg | caggggcgcc cgguucuuuu | 540 |
| ugucaagacc | gaccugucg | gugcccugaa | ugaacugcag | gacgaggcag cgcggcuauc | 600 |
| guggcuggcc | acgacgggcg | uuccuugcgc | agcugugcuc | gacguugca cugaagcggg | 660 |
| aagggacugg | cugcuauugg | gcgaagugcc | ggggcaggau | cuccugucau cucaccuugc | 720 |
| uccugccgag | aaaguaucca | ucauggcuga | ugcaaugcgg | cggcugcaua cgcuugaucc | 780 |
| ggcuaccugc | ccauucgacc | accaagcgaa | acaucgcauc | gagcgagcac guacucggau | 840 |

-continued

```
ggaagccggu cuugucgauc aggaugaucu ggacgaagag caucaggggc ucgcgccagc    900
cgaacuguuc gccaggcuca aggcgcgcau gcccgacggc gaggaucucg ucgugaccca    960
uggcgaugcc ugcuugccga auaucauggu ggaaaauggc cgcuuuucug gauucaucga   1020
cuguggccgg cugggugugg cggaccgcua ucaggacaua gcguuggcua cccgugauau   1080
ugcugaagag cuuggcggcg aaugggcuga ccgcuuccuc gugcuuuacg guaucgccgc   1140
ucccgauucg cagcgcaucg ccuucuaucg ccuucuugac gaguucuucu gaguuuaaac   1200
ccucucccuc cccccccccu aacguuacug gccgaagccg cuuggaauaa ggccggugug   1260
cguuugucua uauguuauuu uccaccauau gccgucuuu uggcaugug agggcccgga    1320 aaccuggccc ugucuucuug acgagcauuc cuaggggucu uccccucuc gccaaaggaa    1380 ugcaaggucu guugaauguc gugaaggaag caguuccucu ggaagcuucu gaagacaaa    1440 caacgucugu agcgacccuu ugcaggcagc ggaaccccc accuggcgac aggugccucu    1500
gcggccaaaa gccacgugua aagauacac cugcaaaggc ggcacaaccc cagugccacg    1560
uugugaguug auaguugug gaaagaguca aauggcucuc cucaagcgua uucaacaagg    1620
ggcugaagga ugcccagaag guaccccauu guaugggauc ugaucugggg ccucggugca    1680
caugcuuuac auguguuuag ucgagguuaa aaaaacgucu aggccccccg aaccacgggg    1740
acgugguuuu ccuuugaaaa acacgaugau accauggcuc ccaucacugc uuaugcccag    1800
caaacacgag gccuccuggg cgccauagug ugaguauga cggggcguga caggacagaa    1860
caggccgggg aaguccaaau ccugccaca gucucucagu ccuucccugg aacaaccauc    1920
ucggggguuu uguggacugu uuaccacgga gcuggcaaca agacucuagc cggcuuacgg    1980
gguccgguca cgcagaugua cucgagugcu gagggggacu ugguaggcug gcccagcccc    2040
ccugggacca agucuuugga gccgugcaag uguggagccg ucgaccuaua ucggucacg    2100 cggaacgcug augucauccc ggcucggaga cgcggggaca agcggggagc auugcucucc    2160
ccgagaccca uuucgaccuu gaaggggucc ucggggggc cggugcucug cccuagggc    2220 cacgucguug ggcucuuccg agcagcugug ugcucucggg gcguggccaa auccaucgau    2280
uucauccccg uugagacacu cgacguuguu acaaggucuc ccacuuucag ugacaacagc    2340
acgccaccgg cugugcccca gaccuaucag gucgggauacu ugcaugcucc aacuggcagu    2400
ggaaagagca ccaaggucc ugucgcguau gccgcccagg gguacaaagu acuagugcuu    2460
aaccccucgg uagcugccac ccuggggguuu ggggcguacc uauccaaggc acauggcauc    2520
aaucccaaca uuaggacugg agucaggacc gugaugaccg gggaggccau cacguacucc    2580
acauauggca aauuucucgc cgauggggc ugcgcuagcg gcgccuauga caucaucaua    2640
ugcgaugaau gccacgcugu ggaugcuacc uccauucucg gcaucggaac gguccuugau    2700
caagcagaga cagccggggu cagacuaacu gugcuggcua cggccacacc ccccggguca    2760
gugacaaccc cccaucccga uauagaagag guaggccucg ggcggagggg ugaucccc    2820 uucuauggga gggcgauucc ccuauccugc aucaaggagg ggagacaccu gauuuucugc    2880
cacucaaaga aaagugugga cgagcucgcg gggcccuuc ggggcauggg cuugaaugcc    2940
guggcauacu auagagggu ggacgucucc auaauaccag cucagggaga guggugguc    3000 gucgccaccg acgcccucau gacggggguac acuggagacu uugacuccgu gaucgacugc    3060
aauguagcgg ucacccaagc ugucgacuuc agccuggacc ccaccuucac uauaaccaca    3120
cagacugucc cacaagacgc ugucucacgc agucagcgcc gcgggcgcac agguagagga    3180
agacagggca cuuauaggua uguuccacu ggugaacgag cccucaggaau guuugacagu    3240
```

| | |
|---|---|
| guagugcuuu gugagugcua cgacgcaggg gcugcguggu acgaucucac accagcggag | 3300 |
| accaccguca ggcuuagagc guauuucaac acgcccggcc uaccgugug ucaagaccau | 3360 |
| cuugaauuuu gggaggcagu uuucaccggc cucacacaca uagacgccca cuccucucc | 3420 |
| caaacaaagc aagcggggga gaacuucgcg uaccuaguag ccuaccaagc uacggugugc | 3480 |
| gccagagcca aggcccucc cccguccugg gacgccaugu ggaagugccu ggcccgacuc | 3540 |
| aagccuacgc uugcgggccc cacaccucuc cguuaccguu ugggcccuau uaccaaugag | 3600 |
| gucacccuca cacacccugg gacgaaguac aucgccacau gcaugcaagc ugaccuugag | 3660 |
| gucaugacca gcacguggu ccuagcugga ggaguccugg cagccgucgc cgcauauugc | 3720 |
| cuggcgacug gaugcguuuc caucaucggc cgcuugcacg ucaaccagcg agucgucguu | 3780 |
| gcgccggaua aggagguccu guaugaggcu uuugaugaga uggaggaaug cgccucuagg | 3840 |
| gcggcucuca ucgaagaggg gcagcggaua gccgagaugu ugaaguccaa gauccaaggc | 3900 |
| uugcugcagc aggccucuaa gcaggccag gacauacaac ccgcuaugca ggcuucaugg | 3960 |
| cccaaagugg aacaauuuug gccagacac auguggaacu cauuagcgg cauccaauac | 4020 |
| cucgcaggau ugucaacacu gccagggaac cccgcggugg cuuccaugau ggcauucagu | 4080 |
| gccgcccuca ccaguccguu gucgaccagu accaccaucc uucucaacau caugggaggc | 4140 |
| ugguuagcgu cccagaucgc accacccgcg ggggccaccg gcuuugucgu cagugggccug | 4200 |
| gugggggcug ccgugggcag cauaggccug gguaaggugc ugguggacau ccuggcagga | 4260 |
| uauggugcgg gcauucgggg ggcccucguc gcauucaaga ucaugucugg cgagaagccc | 4320 |
| ucuauggaag augucaucaa ucuacugccu gggauccugu cccgggagc ccuggugug | 4380 |
| gggucaucu gcgcggccau ucugcgccgc cacgugggac cggggagg gcgcgguccaa | 4440 |
| uggaugaaca ggcuuauugc cuugcuucc agaggaaacc acgucgcccc uacucacuac | 4500 |
| gugacgagu cggaugcguc gcagcgugug acccaacuac uuggcucucu uacuauaacc | 4560 |
| agccuacuca gaagacucca caauuggaua acugaggacu gccccauccc augucccgga | 4620 |
| uccuggcucc gcgacgugug ggacuggguu ugcacauc ugacagacuu caaaaauugg | 4680 |
| cugaccucua aauuguccc caagcugccc ggccuccccu ucauccuug ucaaaagggg | 4740 |
| uacaagggug ugugggccgg cacuggcauc augaccacgc gcugcccuug cggcgccaac | 4800 |
| aucucuggca augucggccu gggcucuaug aggaucacag ggccuaaaac cugcaugaac | 4860 |
| accuggcagg ggaccuuucc uaucaauugc uacacggagg ccagugcgc gccgaaaccc | 4920 |
| cccacgaacu acaagaccgc caucuggagg ugggcggccu cggagucagc ggaggugacg | 4980 |
| cagcaugggu cguacuccua uuaacagga cugaccacug acaaucugaa aauuccuugc | 5040 |
| caacuaccuu cuccagaguu uuucuccugg ugacggug ugcagauccca uagguuugca | 5100 |
| cccacaccaa agccguuuuu ccgggaugag gucucguucu gcguugggcu uaauuccuau | 5160 |
| gcugucgggu cccagcuucc cugugaaccu gagcccgacg cagacguauu gaggccaug | 5220 |
| cuaacagauc cgccccacau cacggcggag acugcggcgc ggcgcuuggc acggggauca | 5280 |
| ccuccaucug aggcgagcuc cucagugagc cagcuaucag caccgucgcu gcgggccacc | 5340 |
| ugcaccacc acagcaacac cuaugacgug gacauggucg augccaaccu gcucauggag | 5400 |
| ggcgugugg cucagacaga gccugagucc agggugcccg uucugacuu ucucgagcca | 5460 |
| auggccgagg aagagagcga ccuugagccc ucaauaccau cggagugcau gcuccccagg | 5520 |
| agcggguuuc cacgggccuu accgcuuugg gcacggccug acuacaaccc gccgucugug | 5580 |
| gaaucgugga ggaggccaga uuaccaaccg cccaccguug cugguugugc ucccccccc | 5640 |

```
cccaagaagg ccccgacgcc uccccccaagg agacgccgga cagugggucu gagcgagagc    5700
accauaucag aagcccucca gcaacuggcc aucaagaccu uuggccagcc ccccucgagc    5760
ggugaugcag gcucguccac gggggcgggc gccgccgaau ccggcggucc gacguccccu    5820
ggugagccgg cccccucaga gacagguucc gccuccucua ugccccccu cgaggggag     5880
ccuggagauc cggaccugga gucugaucag guagagcuuc aaccuccccc caggggggg    5940
gggguagcuc ccguucgggg cucgggucu uggucuacuu gcccgagga ggacgauacc     6000
accgugugcu gcuccaugc auacuccugg accggggcuc uaauaaccc cuguagcccc    6060
gaagaggaaa aguugccaau caaccccuuug aguaacucgc guugcgaua ccauaacaag    6120
guguacugua caacaucaaa gagcgccuca cagagggcua aaaagguaac uuuugacagg    6180
acgcaagugc ucgacgccca uuaugacuca gucuuaaagg acaucaagcu agcggcuucc    6240
aaggucagcg caaggcuccu caccuuggag gaggcgugcc aguugacucc accccauucu    6300
gcaagaucca aguauggauu cggggccaag gaggguccgca gcuuguccgg gagggccguu    6360
aaccacauca aguccgugug gaaggaccuc cuggaagacc cacaaacacc aauucccaca    6420
accaucaugg ccaaaaauga ggguuucgc guggaccccg ccaagggggg uaagaaacca    6480
gcucgcccuca ucguuuaccc ugaccucggc guccgggucu gcgagaaaau ggcccucuau    6540
gacauuacac aaaagcuucc ucaggcggua auggagcuu ccuauggcuu ccaguacucc    6600
ccugcccaac ggguggagua ucucuugaaa gcaugggcgg aaaagaagga ccccaugggu    6660
uuuucguaug uacccgaug cuucgacuca accgucacug agagagacau caggaccgag    6720
gaguccauau accaggccug cucccugccc gaggaggccc gcacugccau acacucgcug    6780
acugagagac uuuacguagg agggcccaug uucaacagca agggucaaac cugcgguuac    6840
agacguugcc gcgccagcgg ggugcuaacc acuagcaugg guaacaccau cacaugcuau    6900
gugaaagccc uagcgccug caaggcgcg gggauaguug cgcccacaau ucagaaagc     6960
caggggacug aggaggacga gcggaaccug agagccuuca cggaggccau gaccagguac    7020
ucugcccccuc cugugaucc ccccagaccg gaauaugacc uggagcuaau aacauccugu    7080
uccucaaaug ugucuguggc guugggcccg cggggccgcc gcagauacua ccugaccaga    7140
gacccaacca cuccacucgc ccgggcugcc ugggaaacag uuagacacuc cccuaucaau    7200
ucauggcugg gaaacaucau ccaguaugcu ccaaccauau ggguucgcau gguccuaaug    7260
acacacuucu ucuccauucu caugguccaa gacacccugg accagaaccu caacuuugag    7320
auguauggau caguauacuc cgugaauccu uggaccuuc cagccauaau ugagagguua    7380
cacgggcuug acgccuuuuc uaugcacaca uacucucacc acgaacugac gcgguggcu    7440
ucagcccuca gaaaacuugg ggcgccaccc cucaggugu ggaagagcg ggcucgcgca    7500
gucagggcgu cccucaucuc ccguggaggg aaagcggccg uuugcggccg auaucucuuc    7560
aauugggcgg ugaagaccaa gcucaaacuc acuccauugc cggaggcgcg ccuacuggac    7620
uuaccaguu gguucaccgu cggcgccggc ggggcgaca uuuucacag cgugucgcgc    7680
gcccgacccc gcucauuacu cuucggccua uccuacuuu ucguaggggu aggcucuuc    7740
cuacuccccg cucgguagag cggcacacac uaggacacu ccauagcuaa cuguuccuuu    7800
uuuuuuuuu uuuuuuuuuu uuuuuuuuu uuuuuuuuu cuuuuuuuu uuuuucccuc     7860
uuucuucccu ucucaucuua uucuacuuuc uucuuggug gcuccaucuu agcccuaguc    7920
acggcuagcu gugaaaggu cgugagccgc augacugcag agagugccgu aacuggucuc    7980
ucugcagauc augu                                                      7994
```

<210> SEQ ID NO 9
<211> LENGTH: 340
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 9
accugccccu aauagggcg acacuccgcc augaaucacu ccccugugag gaacuacugu      60
cuucacgcag aaagcgccua gccauggcgu uaguaugagu gucguacagc cuccaggccc    120 ccccucccg ggagagccau aguggucugc ggaaccggug aguacaccgg aauugccggg     180
aagacugggu ccuuucuugg auaaaccac ucuaugcccg gccauuggg cgugccccg       240 caagacugcu agccgaguag cguugggnuug cgaaaggccu gugguacug ccugauaggg    300 cgcuugcgag ugccccggga ggucucguag accgugcacc                          340

<210> SEQ ID NO 10
<211> LENGTH: 340
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 10
acccgccccu aauagggcg acacuccgcc augaaucacu ccccugugag gaacuacugu      60
cuucacgcag aaagcgucua gccauggcgu uaguaugagu gucguacagc cuccaggccc    120 ccccucccg ggagagccau aguggucugc ggaaccggug aguacaccgg aauugccggg     180
aagacugggu ccuuucuugg auaaaccac ucuaugcccg gccauuggg cgugccccg       240 caagacugcu agccgaguag cguuggguug cgaaaggccu guggguacug ccugauaggg    300
ugcuugcgag ugccccggga ggucucguag accgugcacc                          340

<210> SEQ ID NO 11
<211> LENGTH: 236
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 11
agcggcacac acuagguaca cuccauagcu aacuguuccu uuuuuuuuu uuuuuuuuu       60 uuuuuuuuu uuuuuuuuu uucuuuuuu uuuuuuccc ucuuucuucc cuucucaucu        120
uauucuacuu ucuuucuugg uggcuccauc uuagcccuag ucacggcuag cugugaaagg    180
uccgugagcc gcaugacugc agagagugcc guaacgguc ucucugcaga ucaugu         236

<210> SEQ ID NO 12
<211> LENGTH: 232
<212> TYPE: RNA
<213> ORGANISM: Artificial Sequence
<220> FEATURE:
<223> OTHER INFORMATION: Description of Artificial Sequence: synthetic
      RNA

<400> SEQUENCE: 12
agcggcacac auuagcuaca cuccauagcu aacuguuccu uuuuuuuuu uuuuuuuuu       60 uuuuuuuuuu uuuuucuu uuuuuuuuuu uucccucuu ucuucccuuc ucaucuuauu      120

```
cuacuuucuu ucuugguggc uccaucuuag cccuggucac ggcuagcugu gaaagguccg        180
ugagccgcau gacugcagag agugccguaa cuggucucuc ugcagaucau gu               232
```

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13

```
cgggagagcc atagtgg                                                       17
```

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14

```
agtaccacaa ggcctttcg                                                     19
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15

```
ctgcggaacc ggtgagtaca c                                                  21
```

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16

```
aacaagatgg attgcacgca                                                    20
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17

```
cgtcaagaag gcgatagaag                                                    20
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
gcactctctg cagtcatgcg gctcacggac                                    30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
cccctgtgag gaactactgt cttcacgc                                      28

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
ccgggagagc catagtggtc tgcg                                          24

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
ccactcaaag aaaaagtgtg acgagctcgc                                    30

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
ggcttgggca cggcctga                                                 18

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
gcggtgaaga ccaagctcaa actcactcca                                    30

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 24
agaacctgcg tgcaatccat c                                             21

```
<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
cccgtcatga gggcgtcggt ggc                                              23

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
accagcaacg gtgggcggtt ggtaatc                                          27

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
ggcacgcgac acgctgtg                                                    18

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
agctagccgt gactagggct aagatggagc                                       30

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: synthetic
      DNA(primer)

<400> SEQUENCE: 29
aacaagatgg attgcacgca                                                  20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: synthetic
      DNA(primer)

<400> SEQUENCE: 30
cgtcaagaag gcgatagaag                                                  20

<210> SEQ ID NO 31
```

```
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
gcactctctg cagtcatgcg gctcacggac                                    30

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
cccctgtgag gaactactgt cttcacgc                                      28

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
ccgggagagc catagtggtc tgcg                                          24

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
ccactcaaag aaaaagtgtg acgagctcgc                                    30

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: synthetic
      DNA(primer)

<400> SEQUENCE: 35
ggcttgggca cggcctga                                                 18

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
gcggtgaaga ccaagctcaa actcactcca                                    30

<210> SEQ ID NO 37
<211> LENGTH: 21
<212> TYPE: DNA
```

-continued

```
<213> ORGANISM: Artificial Sequence
<220> FEATURE:
<223> OTHER INFORMATION: Description of Artificial Sequence: synthetic
      DNA

<400> SEQUENCE: 37
agaacctgcg tgcaatccat c                                                    21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 38
cccgtcatga gggcgtcggt ggc                                                  23

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 39
accagcaacg gtgggcggtt ggtaatc                                              27

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 40
ggaacgcgac acgctgtg                                                        18

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 41
agctagccgt gactagggct aagatggagc                                           30
```